United States Patent
Oota et al.

(10) Patent No.: US 8,354,208 B2
(45) Date of Patent: *Jan. 15, 2013

(54) COLORED CURABLE COMPOSITION, METHOD FOR PRODUCING COLOR FILTER, COLOR FILTER, SOLID-STATE IMAGE PICKUP DEVICE, AND LIQUID CRYSTAL DISPLAY DEVICE

(75) Inventors: Kazuya Oota, Shizuoka-ken (JP); Shinichi Kanna, Shizuoka-ken (JP); Yoshihiko Fujie, Shizuoka-ken (JP); Junichi Ito, Shizuoka-ken (JP); Yosuke Murakami, Shizuoka-ken (JP); Shigekazu Suzuki, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 115 days.

This patent is subject to a terminal disclaimer.

(21) Appl. No.: 12/943,959

(22) Filed: Nov. 11, 2010

(65) Prior Publication Data

US 2011/0051058 A1  Mar. 3, 2011

Related U.S. Application Data

(63) Continuation-in-part of application No. 12/749,533, filed on Mar. 30, 2010.

(30) Foreign Application Priority Data

| Mar. 31, 2009 | (JP) | 2009-087654 |
| May 14, 2009 | (JP) | 2009-117911 |
| Jun. 5, 2009 | (JP) | 2009-136012 |
| Jan. 22, 2010 | (JP) | 2010-011840 |
| Mar. 25, 2010 | (JP) | 2010-070850 |

(51) Int. Cl.
*G02B 5/20* (2006.01)
*G02F 1/1335* (2006.01)

(52) U.S. Cl. ....... 430/7; 430/270.1; 349/106; 257/440

(58) Field of Classification Search ............ None
See application file for complete search history.

(56) References Cited

U.S. PATENT DOCUMENTS

| 2008/0076044 A1 | 3/2008 | Mizukawa et al. |
| 2008/0171271 A1 | 7/2008 | Kim et al. |

FOREIGN PATENT DOCUMENTS

| JP | 2001-033616 A | 2/2001 |
| JP | 2006-065121 A | 3/2006 |
| JP | 2007-033579 A | 2/2007 |
| JP | 2008-292970 A | 12/2008 |
| JP | 2009-031713 A | 2/2009 |

*Primary Examiner* — John A. McPherson
(74) *Attorney, Agent, or Firm* — SOLARIS Intellectual Property Group, PLLC

(57) ABSTRACT

A colored curable composition including at least (A-1) a complex including a compound represented by the following formula (I) and a metal atom or a metal compound, (A-2) a phthalocyanine pigment, (B) a dispersing agent, (C) a polymerizable compound, (D) a photopolymerization initiator, and (E) an organic solvent:

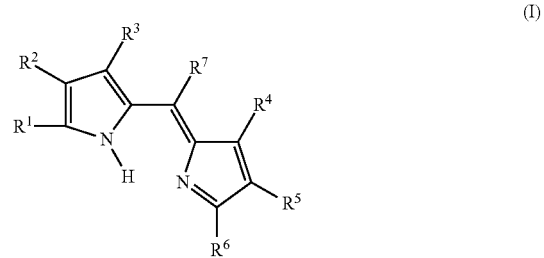

(I)

wherein $R^1$ to $R^6$ each independently represent a hydrogen atom or a substituent, but $R^1$ and $R^6$ do not bond to each other to form a ring structure; and $R^7$ represents a hydrogen atom, a halogen atom, an alkyl group, an aryl group or a heterocyclic group.

11 Claims, No Drawings

COLORED CURABLE COMPOSITION, METHOD FOR PRODUCING COLOR FILTER, COLOR FILTER, SOLID-STATE IMAGE PICKUP DEVICE, AND LIQUID CRYSTAL DISPLAY DEVICE

CROSS-REFERENCE TO RELATED APPLICATION

This application is a continuation-in-part of U.S. patent application Ser. No. 12/749,533 filed on Mar. 30, 2010, the disclosure of which is incorporated by reference herein.

This application claims priority under 35 USC 119 from Japanese Patent Application No. 2009-087654 filed on Mar. 31, 2009, Japanese Patent Application No. 2009-117911 filed on May 14, 2009, Japanese Patent Application No. 2009-136012 filed on Jun. 5, 2009, Japanese Patent Application No. 2010-011840 filed on Jan. 22, 2010, and Japanese Patent Application No. 2010-070850 filed on Mar. 25, 2010, the disclosures of which are incorporated by reference herein.

BACKGROUND OF THE INVENTION

1. Field of the Invention

The present invention relates to a colored curable composition, a method for producing a color filter, a color filter, and a solid-state image pickup device and a liquid crystal display device including the color filter.

2. Description of the Related Art

As a method for preparing a color filter to be used for a liquid crystal display device (such as a LCD) and a solid-state image pickup device (such as a CCD or a CMOS), a pigment dispersing method has been widely known.

The pigment dispersing method is a method for preparing a color filter by a photolithographic method using colored photosensitive compositions in which pigments are dispersed in various photosensitive compositions. Since patterning is performed by a photolithographic method, this method is considered to be a preferable method for preparing a color filter having high positional accuracy, a large area and high definition. When a color filter is prepared by the pigment dispersing method, a coating is formed by applying a photosensitive composition on a glass substrate using a spin coater, a roll coater or the like, colored pixels are formed by pattern-exposing and developing the coating, and a color filter is obtained by repeating these operations for each color.

As an example of a colored photosensitive composition using a pigment, a blue-colored composition for a color filter including a phthalocyanine pigment as described in Japanese Patent Application Laid-Open (JP-A) No. 2001-33616 has been known.

When a display device such as a liquid crystal display device or a solid-state image pickup device is prepared by providing a color filter using a pigment, a pigment having a finer particle size is required in view of improvement of contrast. This is due to a factor that a polarization axis is rotated by scattering, birefringence and the like of light by a pigment. When refinement of a pigment is insufficient, light is scattered and absorbed by the pigment, whereby light transmittance is decreased, contrast is decreased, and curing sensitivity during pattern exposing is decreased.

In particular, higher definition has been recently desired for a color filter for a solid-state image pickup device, but further improvement of resolution is difficult in a conventionally-used pigment dispersion system under the present circumstances. Namely, there are problems in that unevenness of color is caused by the effect of coarse particles in the pigment, and the like. Therefore, the pigment dispersion system is not suitable for applications in which a fine pattern having a pixel size of 1.5 to 3.0 µm-square is required such as a solid-state image pickup device.

In response to such circumstances, a technique using a dye instead of a pigment has conventionally been suggested. However, dyes have been known to be generally inferior to pigments in light resistance and heat resistance, and sometimes problematic in view of performance of a color filter. Furthermore, dyes have problems in that they have low solubility in a photosensitive composition, and in that they have low stability over time and precipitate in the state of a liquid preparation or a coating film.

In response to these problems, a colored curable composition using a dye including a dipyrromethene compound and a phthalocyanine dye in combination, which has excellent storage stability and is capable of forming a color filter having high light resistance, has been suggested (see, for example, JP-A No. 2008-292970).

Furthermore, a colored curable composition including a dye and a pigment in combination has also been known (see, for example, US Patent Application Publication No. 2008/0171271).

As mentioned above, with respect to a colored curable composition including a dye, it has been known that an effect that a color filter having excellent storage stability and high light resistance may be formed is obtained by selecting a dye to be used. However, under the present circumstances, further improvement of this effect is desired for higher definition and improved performance of a color filter.

SUMMARY OF THE INVENTION

According to an aspect of the invention, there is provided a colored curable composition comprising at least (A-1) a complex comprising a compound represented by the following formula (I) and a metal atom or a metal compound, (A-2) a phthalocyanine pigment, (B) a dispersing agent, (C) a polymerizable compound, (D) a photopolymerization initiator, and (E) an organic solvent:

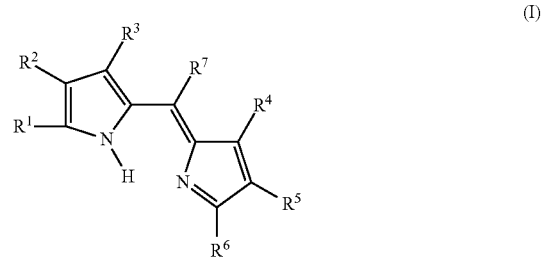

wherein $R^1$ to $R^6$ each independently represent a hydrogen atom or a substituent, but $R^1$ and $R^6$ do not bond to each other to form a ring structure; and $R^7$ represents a hydrogen atom, a halogen atom, an alkyl group, an aryl group or a heterocyclic group.

DETAILED DESCRIPTION OF THE INVENTION

Colored Curable Composition

First, the colored curable composition of the present invention is explained.

The colored curable composition of the invention is a colored curable composition including at least (A-1) a complex including a compound represented by the formula (I) and a metal atom or a metal compound, (A-2) a phthalocyanine pigment, (B) a dispersing agent, (C) a polymerizable compound, (D) a photopolymerization initiator, and (E) an organic solvent.

The components (A-1), (A-2), (B), (C), (D) and (E) are explained below.

[(A-1) A Complex Including a Compound Represented by the Formula (I) and a Metal Atom or a Metal Compound]

The colored curable composition of the invention includes (A-1) a complex including a compound represented by the formula (I) and a metal atom or a metal compound (hereinafter suitably referred to as "specific complex") as one of colorants. The specific complex usually includes a compound represented by the formula (I) in deprotonated form.

—Dipyrromethene Compound—

First, the compound represented by the formula (I) which is included in the specific complex is explained.

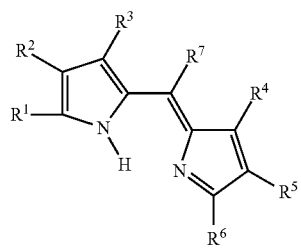

(I)

In the formula (I), $R^1$ to $R^6$ each independently represent a hydrogen atom or a substituent, but $R^1$ and $R^6$ do not bond to each other to form a ring structure, and $R^7$ represents a hydrogen atom, a halogen atom, an alkyl group, an aryl group or a heterocyclic group.

Examples of the substituent represented by $R^1$ to $R^6$ in the formula (I) include the monovalent groups as shown below (hereinafter the group of the listed monovalent groups is sometimes collectively referred to as "Substituent R").

Namely, the examples include a halogen atom (e.g., a fluorine atom, a chlorine atom, a bromine atom), an alkyl group (a straight chain, branched chain or cyclic alkyl group having preferably 1 to 48, more preferably 1 to 24 carbon atoms, such as a methyl group, an ethyl group, a propyl group, an isopropyl group, a butyl group, a t-butyl group, a pentyl group, a hexyl group, a heptyl group, an octyl group, a 2-ethylhexyl group, a dodecyl group, a hexadecyl group, a cyclopropyl group, a cyclopentyl group, a cyclohexyl group, a 1-norbornyl group and a 1-adamantyl group), an alkenyl group (an alkenyl group having preferably 2 to 48, more preferably 2 to 18 carbon atoms, such as a vinyl group, an allyl group and a 3-buten-1-yl group), an aryl group (an aryl group having preferably 6 to 48, more preferably 6 to 24 carbon atoms, such as a phenyl group and a naphthyl group), a heterocyclic group (a heterocyclic group having preferably 1 to 32, more preferably 1 to 18 carbon atoms, such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group and a benzotriazol-1-yl group), a silyl group (a silyl group having preferably 3 to 38, more preferably 3 to 18 carbon atoms, such as a trimethylsilyl group, a triethylsilyl group, a tributylsilyl group, a t-butyldimethylsilyl group and a t-hexyldimethylsilyl group), a hydroxyl group, a cyano group, a nitro group, an alkoxy group (an alkoxy group having preferably 1 to 48, more preferably 1 to 24 carbon atoms, such as a methoxy group, an ethoxy group, a 1-butoxy group, a 2-butoxy group, an isopropoxy group, a t-butoxy group, a dodecyloxy group, and cycloalkyloxy groups including a cyclopentyloxy group and a cyclohexyloxy group), an aryloxy group (an aryloxy group having preferably 6 to 48, more preferably 6 to 24 carbon atoms, such as a phenoxy group and a 1-naphthoxy group), a heterocycleoxy group (a heterocycleoxy group having preferably 1 to 32, more preferably 1 to 18 carbon atoms, such as a 1-phenyltetrazole-5-oxy group and a 2-tetrahydropyranyloxy group), a silyloxy group (a silyloxy group having preferably 1 to 32, more preferably 1 to 18 carbon atoms, such as a trimethylsilyloxy group, a t-butyldimethylsilyloxy group and a diphenylmethylsilyloxy group), an acyloxy group (an acyloxy group having preferably 2 to 48, more preferably 2 to 24 carbon atoms, such as an acetoxy group, a pivaloyloxy group, a benzoyloxy group and a dodecanoyloxy group), an alkoxycarbonyloxy group (an alkoxycarbonyloxy group having preferably 2 to 48, more preferably 2 to 24 carbon atoms, such as an ethoxycarbonyloxy group, a t-butoxycarbonyloxy group, and a cycloalkyloxycarbonyloxy group, such as a cyclohexyloxycarbonyloxy group), an aryloxycarbonyloxy group (an aryloxycarbonyloxy group having preferably 7 to 32, more preferably 7 to 24 carbon atoms, such as a phenoxycarbonyloxy group), a carbamoyloxy group (a carbamoyloxy group having preferably 1 to 48, more preferably 1 to 24 carbon atoms, such as an N,N-dimethylcarbamoyloxy group, an N-butylcarbamoyloxy group, an N-phenylcarbamoyloxy group and an N-ethyl-N-phenylcarbamoyloxy group), a sulfamoyloxy group (a sulfamoyloxy group including preferably 1 to 32, more preferably 1 to 24 carbon atoms, such as an N,N-diethylsulfamoyloxy group and an N-propylsulfamoyloxy group), an alkylsulfonyloxy group (an alkylsulfonyloxy group having preferably 1 to 38, more preferably 1 to 24 carbon atoms, such as a methylsulfonyloxy group, a hexadecylsulfonyloxy group and a cyclohexylsulfonyloxy group), an arylsulfonyloxy group (an arylsulfonyloxy group having preferably 6 to 32, more preferably 6 to 24 carbon atoms, such as a phenylsulfonyloxy group), an acyl group (an acyl group having preferably 1 to 48, more preferably 1 to 24 carbon atoms, such as a formyl group, an acetyl group, a pivaloyl group, a benzoyl group, a tetradecanoyl group and a cyclohexanoyl group), an alkoxycarbonyl group (an alkoxycarbonyl group having preferably 2 to 48, more preferably 2 to 24 carbon atoms, such as a methoxycarbonyl group, an ethoxycarbonyl group, an octadecyloxycarbonyl group, a cyclohexyloxycarbonyl group and a 2,6-di-tert-butyl-4-methylcyclohexyloxycarbonyl group), an aryloxycarbonyl group (an aryloxycarbonyl group having preferably 7 to 32, more preferably 7 to 24 carbon atoms, such as a phenoxycarbonyl group), a carbamoyl group (a carbamoyl group having preferably 1 to 48, more preferably 1 to 24 carbon atoms, such as a carbamoyl group, an N,N-diethylcarbamoyl group, an N-ethyl-N-octylcarbamoyl group, an N,N-dibutylcarbamoyl group, an N-propylcarbamoyl group, an N-phenylcarbamoyl group, a N-methyl-N-phenylcarbamoyl group and an N,N-dicyclohexylcarbamoyl group), an amino group (an amino group having preferably 32 or less, more preferably 24 or less carbon atoms, such as an amino group, a methylamino group, an N,N-dibutylamino group, a tetradecylamino group, a 2-ethylhexylamino group and a cyclohexylamino group), an anilino group (an anilino group having preferably 6 to 32, more preferably 6 to 24 carbon atoms, such as an anilino group and an N-methylanilino group), a heterocyclic amino group (a heterocyclic amino group having preferably 1 to 32, more preferably 1 to 18 carbon atoms, such as a 4-pyridylamino group), a carbonamide group (a carbonamide group having preferably 2 to 48, more preferably 2 to 24 carbon atoms, such as an acetamide group, a benzamide group, a tetradecanamide group, a pivaloylamide group and a cyclohexanamide group), an ureido group (an ureido group having preferably 1 to 32, more preferably 1 to 24 carbon atoms, such as an ureido group, an N,N-dimethylureido group and an N-phenylureido group), an imide group (an imide group having preferably 36 or less, more preferably 24 or less carbon atoms, such as an N-succinimide group and an N-phthalimide group), an alkoxycarbonylamino group (an alkoxycarbonylamino group having preferably 2 to 48, more preferably 2 to 24 carbon atoms, such as a methoxycarbonylamino group, an ethoxycarbonylamino group, a t-butoxycarbonylamino group, an octadecyloxycarbonylamino group and a cyclohexyloxycarbonylamino group), an aryloxycarbonylamino group (an aryloxycarbonylamino group having preferably 7 to 32, more preferably 7 to 24 carbon atoms, such as an phenoxycarbonylamino group), a sulfonamide group (a sulfonamide group having preferably 1 to 48, more preferably 1 to 24 carbon atoms, such as a methanesulfonamide group, a butanesulfonamide group, a benzenesulfonamide group, a hexadecanesulfonamide group and a cyclohexanesulfonamide group), a sulfamoylamino group (a sulfamoylamino group having preferably 1 to 48, more preferably 1 to 24 carbon atoms, such as an N,N-dipropylsulfamoylamino group and an N-ethyl-N-dodecylsulfamoylamino group), an azo group (an azo group having preferably 1 to 32, more preferably 1 to 24 carbon atoms, such as a phenylazo group and a 3-pyrazolylazo group), an alkylthio group (an alkylthio group having preferably 1 to 48, more preferably 1 to 24 carbon atoms, such as a methylthio group, an ethylthio group, an octylthio group and a cyclohexylthio group), an arylthio group (an arylthio group having preferably 6 to 48, more preferably 6 to 24 carbon atoms, such as a phenylthio group), a heterocyclic thio group (a heterocyclic thio group having preferably 1 to 32, more preferably 1 to 18 carbon atoms, such as a 2-benzothiazolylthio group, a 2-pyridylthio group and a 1-phenyltetrazolylthio group), an alkylsulfinyl group (an alkylsulfinyl group having preferably 1 to 32, more preferably 1 to 24 carbon atoms, such as a dodecanesulfinyl group), an arylsulfinyl group (an arylsulfinyl group having preferably 6 to 32, more preferably 6 to 24 carbon atoms, such as a phenylsulfinyl group), an alkylsulfonyl group (an alkylsulfonyl group having preferably 1 to 48, more preferably 1 to 24 carbon atoms, such as a methylsulfonyl group, an ethylsulfonyl group, a propylsulfonyl group, a butylsulfonyl group, an isopropylsulfonyl group, a 2-ethylhexylsulfonyl group, a hexadecylsulfonyl group, an octylsulfonyl group and a cyclohexylsulfonyl group), an arylsulfonyl group (an arylsulfonyl group having preferably 6 to 48, more preferably 6 to 24 carbon atoms, such as a phenylsulfonyl group and a 1-naphthylsulfonyl group), a sulfamoyl group (a sulfamoyl group having preferably 32 or less, more preferably 24 or less carbon atoms, such as a sulfamoyl group, an N,N-dipropylsulfamoyl group, an N-ethyl-N-dodecylsulfamoyl group, an N-ethyl-N-phenylsulfamoyl group and an N-cyclohexylsulfamoyl group), a sulfo group, a phosphonyl group (a phosphonyl group having preferably 1 to 32, more preferably 1 to 24 carbon atoms, such as a phenoxyphosphonyl group, an octyloxyphosphonyl group and a phenylphosphonyl group) and a phosphinoylamino group (a phosphinoylamino group having preferably 1 to 32, more preferably 1 to 24 carbon atoms, such as a diethoxyphosphinoylamino group and an dioctyloxyphosphinoylamino group).

When the above-mentioned monovalent group is a group that may further be substituted, it may further be substituted by any of the above-mentioned groups. When the monovalent group has two or more substituents, those substituents may be the same or different.

In the formula (I), $R^1$ and $R^2$, $R^2$ and $R^3$, $R^4$ and $R^5$, and $R^5$ and $R^6$ each may independently bond to each other to form a 5-, 6- or 7-membered ring. Examples of the ring to be formed include saturated or unsaturated rings. Examples of the 5-, 6- or 7-membered saturated or unsaturated rings include a pyrrole ring, a furan ring, a thiophene ring, a pyrazole ring, an imidazole ring, a triazole ring, an oxazole ring, a thiazole ring, a pyrrolidine ring, a piperidine ring, a cyclopentene ring, a cyclohexene ring, a benzene ring, a pyridine ring, a pyrazine ring and a pyridazine ring, preferably a benzene ring and a pyridine ring.

When the 5-, 6- or 7-membered ring to be formed is a group that may further be substituted, it may be substituted by any of Substituent R, and when the ring is substituted by two or more substituents, those substituent may be the same or different.

—Metal Atom or Metal Compound—

Next, the metal atom or metal compound that is included in the specific complex is explained.

The metal atom or metal compound as used herein may be any metal atom or metal compound so long as it may form a complex, and examples include bivalent metal atoms, bivalent metal oxides, bivalent metal hydroxides and bivalent metal chlorides. For example, Zn, Mg, Si, Sn, Rh, Pt, Pd, Mo, Mn, Pb, Cu, Ni, Co, Fe and the like, as well as metal chlorides including AlCl, InCl, FeCl, $TiCl_2$, $SnCl_2$, $SiCl_2$ and $GeCl_2$, metal oxides including TiO and VO, and metal hydroxides including $Si(OH)_2$ are included.

Among these, Fe, Zn, Mg, Si, Pt, Pd, Mo, Mn, Cu, Ni, Co, TiO and VO are preferable, Fe, Zn, Mg, Si, Pt, Pd, Cu, Ni, Co and VO are further preferable, and Fe, Zn, Cu, Co and VO (V=O) are the most preferable in view of stability, spectral property, heat resistance, light resistance, and production suitability and the like of the complex.

A preferable embodiment of the complex including the compound represented by the formula (I) and the metal atom or the metal compound is shown below.

Namely, an embodiment in which $R^1$ and $R^6$ each independently represent a hydrogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an amino group, an anilino group, a heterocyclic amino group, a carbonamide group, an ureido group, an imide group, an alkoxycarbonylamino group, an aryloxycarbonylamino group, a sulfonamide group, an azo group, an alkylthio group, an arylthio group, a heterocyclic thio group, an alkylsulfonyl group, an arylsulfonyl group or a phosphinoylamino group, $R^2$ and $R^5$ each independently represent a hydrogen atom, a halogen atom, an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imide group, an alkoxycarbonylamino group, a sulfonamide group, an azo group, an alkylthio group, an arylthio group, a heterocyclic thio group, an alkylsulfonyl group, an arylsulfonyl group or a sulfamoyl group, $R^3$ and $R^4$ each independently represent a hydrogen atom, a halogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an anilino group, a carbonamide group, an ureido group, an imide group, an alkoxycarbonylamino group, a sulfonamide group, an azo group, an alkylthio group, an arylthio group, a heterocyclic thio group, an alkylsulfonyl group, an arylsulfonyl group, a sulfamoyl group or a phosphinoylamino group, and $R^7$ represents a hydrogen atom, a halogen atom, an alkyl group, an aryl group or a heterocyclic group in the formula (I), and the metal atom or the metal compound is Zn, Mg, Si, Pt, Pd, Mo, Mn, Cu, Ni, Co, TiO or VO, is exemplified.

A more preferable embodiment of the complex including the compound represented by the formula (I) and the metal atom or the metal compound is shown below.

Namely, an embodiment in which $R^1$ and $R^6$ each independently represent a hydrogen atom, an alkyl group, an alkenyl group, an aryl group, a heterocyclic group, a cyano group, an acyl group, an alkoxycarbonyl group, a carbamoyl group, an amino group, a heterocyclic amino group, a carbonamide group, an ureido group, an imide group, an alkoxycarbonylamino group, an aryloxycarbonylamino group, a sulfonamide group, an azo group, an alkylsulfonyl group, an arylsulfonyl group or a phosphinoylamino group, $R^2$ and $R^5$ each independently represent an alkyl group, an alkenyl group, an aryl group, a heterocyclic group, a cyano group, a nitro group, an acyl group, an alkoxycarbonyl group, an aryloxycarbonyl group, a carbamoyl group, an imide group, an alkylsulfonyl group, an arylsulfonyl group or a sulfamoyl group, $R^3$ and $R^4$ each independently represent a hydrogen atom, an alkyl group, an alkenyl group, an aryl group, a heterocyclic group, a cyano group, an acyl group, an alkoxycarbonyl group, a carbamoyl group, a carbonamide group, an ureido group, an imide group, an alkoxycarbonylamino group, a sulfonamide group, an alkylthio group, an arylthio group, a heterocyclic thio group, an alkylsulfonyl group, an arylsulfonyl group or a sulfamoyl group, and $R^7$ represents a hydrogen atom, a halogen atom, an alkyl group, an aryl group or a heterocyclic group in the formula (I), and the metal atom or the metal compound is Zn, Mg, Si, Pt, Pd, Cu, Ni, Co or VO, is exemplified.

A specifically preferable embodiment of the complex including the compound represented by the formula (I) and the metal atom or the metal compound is shown below.

Namely, an embodiment in which $R^1$ and $R^6$ each independently represent a hydrogen atom, an alkyl group, an aryl group, a heterocyclic group, an amino group, a heterocyclic amino group, a carbonamide group, an ureido group, an imide group, an alkoxycarbonylamino group, a sulfonamide group, an azo group, an alkylsulfonyl group, an arylsulfonyl group or a phosphinoylamino group, $R^2$ and $R^5$ each independently represent an alkyl group, an aryl group, a heterocyclic group, a cyano group, an acyl group, an alkoxycarbonyl group, a carbamoyl group, an alkylsulfonyl group or an arylsulfonyl group, $R^3$ and $R^4$ each independently represent a hydrogen atom, an alkyl group, an aryl group or a heterocyclic group, and $R^7$ represents a hydrogen atom, an alkyl group, an aryl group or a heterocyclic group in the formula (I), and the metal atom or the metal compound is Zn, Cu, Co or VO, is exemplified.

Specifically, in the formula (I), $R^3$ and $R^4$ are preferably each a phenyl group in view of excellent toughness. The reason is considered that (1) since $R^3$ and $R^4$ are each a phenyl group, the spectrum of this compound is shifted to longer wavelengths and overlapping with the spectrum of the phthalocyanine pigment that is used in combination (at around 550 nm) is increased, which allows easy transfer of energy, and that (2) the toughness of this compound itself is increased due to presence of sterically bulky substituents.

Furthermore, in the formula (I), $R^2$ and/or $R^5$ is preferably a 2,6-di-tert-butyl-4-methylcyclohexyloxycarbonyl group in view of excellent solubility in solvents.

—Compound Represented by the Formula (II-1)—

One of the preferable examples of the specific complex in the invention is the compound represented by the following formula (II-1).

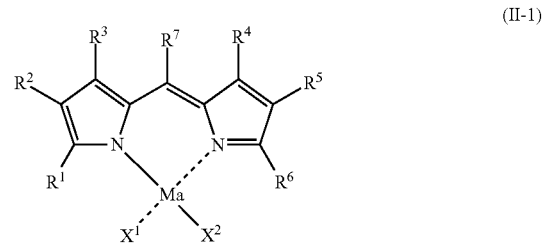

(II-1)

In the formula (II-1), $R^1$ to $R^6$ each independently represent a hydrogen atom or a substituent, $R^7$ represents a hydrogen atom, a halogen atom, an alkyl group, an aryl group or a heterocycle group, Ma represents a metal atom or a metal compound, $X^2$ represents a group that is necessary for neutralizing the charge of Ma, and $X^1$ represents a group capable of bonding to Ma, wherein $X^1$ and $X^2$ may bond to each other to form a 5-, 6- or 7-membered ring.

$R^1$ to $R^6$ in the formula (II-1) have the same definitions as $R^1$ to $R^6$ in the formula (I), and preferable embodiments thereof are also the same.

Ma in the formula (II-1) is a metal atom or a metal compound that has the same definition as the metal atom or the metal compound that is included in the above-mentioned specific complex, and the preferable range thereof is the same.

$R^7$ in the formula (II-1) has the same definition as $R^7$ in the formula (I), and the preferable embodiment thereof is also the same.

$X^1$ in the formula (II-1) may be any group so long as it is capable of bonding to Ma, and examples include water, alcohols (e.g., methanol, ethanol, propanol) and the like, as well as groups derived from the compounds described in "Metal Chelates" [1] Takeichi Sakaguchi and Kyohei Ueno (1995 Nankodo), "Metal Chelates" [2] (1996), "Metal Chelates" [3] (1997) and the like.

$X^2$ in the formula (II-1) is a group that is necessary for neutralizing the charge of Ma, and examples include a halogen atom, a hydroxy group, a carboxylic acid group, a phosphoric acid group, a sulfonic acid group and the like.

$X^1$ and $X^2$ in the formula (II-1) may bond to each other to form a 5-, 6- or 7-membered ring. The 5-, 6- or 7-membered ring to be formed may be a saturated or unsaturated ring. Furthermore, the 5-, 6- or 7-membered ring may be formed by only carbon atoms and hydrogen atoms, or may be a heterocycle having at least one atom selected from a nitrogen atom, an oxygen atom and a sulfur atom.

—Compound Represented by the Formula (II-2)—

One of the preferable examples of the specific complex in the invention is a compound represented by the following formula (II-2).

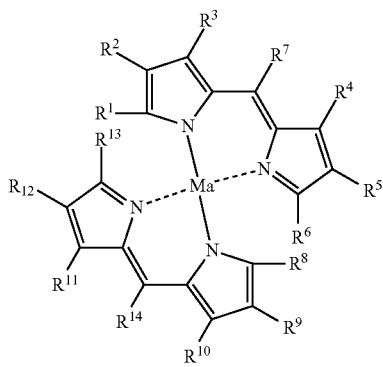

(II-2)

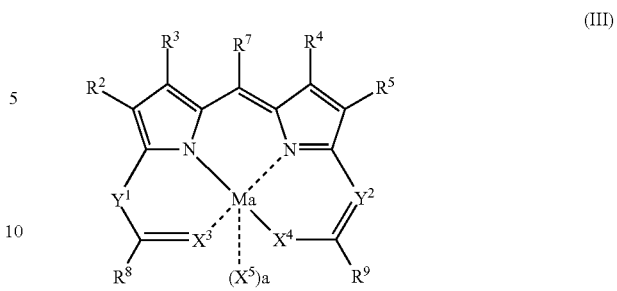

(III)

In the formula (II-2), $R^1$ to $R^6$ and $R^8$ to $R^{13}$ each independently represent a hydrogen atom or a substituent, $R^7$ and $R^{14}$ each independently represent a hydrogen atom, a halogen atom, an alkyl group, an aryl group or a heterocyclic group, and Ma represents a metal atom or a metal compound.

$R^1$ to $R^6$ in the formula (II-2) have the same definitions as $R^1$ to $R^6$ in formula (I), and preferable embodiments thereof are also the same.

The substituents represented by $R^8$ to $R^{13}$ in the formula (II-2) have the same definitions as $R^1$ to $R^6$ in the compound represented by the formula (I), and preferable embodiments thereof are also the same. When the substituents represented by $R^8$ to $R^{13}$ in the formula (II-2) are groups that may further be substituted, they may be substituted by any of Substituent R mentioned above, and when they are substituted by two or more substituents, those substituents may be the same or different.

$R^7$ in the formula (II-2) has the same definition as $R^7$ in the formula (I), and the preferable embodiments are also the same.

$R^{14}$ in the formula (II-2) is a hydrogen atom, a halogen atom, an alkyl group, an aryl group or a heterocyclic group, and the preferable range of $R^{14}$ is the same as the preferable range of $R^7$. When $R^{14}$ is a group that may further be substituted, it may be substituted by any of Substituent R mentioned above, and when it is substituted by two or more substituents, the substituents may be the same or different.

Ma in the formula (II-2) represents a metal atom or a metal compound that has the same definition as the metal atom or the metal compound that is included in the specific complex mentioned above, and the preferable range is also the same.

$R^8$ and $R^9$, $R^9$ and $R^{10}$, $R^{11}$ and $R^{12}$, and $R^{12}$ and $R^{13}$ in the formula (II-2) each may independently bond to each other to form a 5-, 6- or 7-membered saturated or unsaturated ring. The saturated or unsaturated ring to be formed has the same definition as the saturated or unsaturated ring to be formed by $R^1$ and $R^2$, $R^2$ and $R^3$, $R^4$ and $R^5$, or $R^5$ and $R^6$, and the preferable examples thereof are the same.

—Compound Represented by the Formula (III)—

One of the preferable examples of the specific complex in the invention is the compound represented by the following formula (III).

In the formula (III), $R^2$ to $R^5$ each independently represent a hydrogen atom or a substituent, $R^7$ represents a hydrogen atom, a halogen atom, an alkyl group, an aryl group or a heterocyclic group, Ma represents a metal atom or a metal compound, $X^3$ represents NR (wherein R represents a hydrogen atom, an alkyl group, an alkenyl group, an aryl group, a heterocyclic group, an acyl group, an alkylsulfonyl group or an arylsulfonyl group), a nitrogen atom, an oxygen atom or a sulfur atom, $X^4$ represents NRa (wherein Ra represents a hydrogen atom, an alkyl group, an alkenyl group, an aryl group, a heterocyclic group, an acyl group, an alkylsulfonyl group or an arylsulfonyl group), an oxygen atom or a sulfur atom, $Y^1$ represents NRc (wherein Rc represents a hydrogen atom, an alkyl group, an alkenyl group, an aryl group, a heterocyclic group, an acyl group, an alkylsulfonyl group or an arylsulfonyl group), a nitrogen atom or a carbon atom, $Y^2$ represents a nitrogen atom or a carbon atom, $R^8$ and $R^9$ each independently represent an alkyl group, an alkenyl group, an aryl group, a heterocyclic group, an alkoxy group, an aryloxy group, an alkylamino group, an arylamino group or a heterocyclic amino group, $R^8$ and $Y^1$ may bond to each other to form a 5-, 6- or 7-membered ring, $R^9$ and $Y^2$ may bond to each other to form a 5-, 6- or 7-membered ring, $X^5$ represents a group capable of bonding to Ma, and a represents 0, 1, or 2.

$R^2$ to $R^5$ and $R^7$ in the formula (III) have the same definitions as the $R^1$ to $R^6$ and $R^7$ in the compound represented by the formula (I), and preferable embodiments thereof are also the same.

Ma in the formula (III) represents a metal atom or a metal compound that has the same definition as the metal atom or the metal compound that is included in the specific complex mentioned above, and the preferable range thereof is also the same.

In the formula (III), $R^8$ and $R^9$ each independently represent an alkyl group (a straight chain, branched chain or cyclic alkyl group having preferably 1 to 36, more preferably 1 to 12 carbon atoms, such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group and a 1-adamantyl group), an alkenyl group (an alkenyl group having preferably 2 to 24, more preferably 2 to 12 carbon atoms, such as a vinyl group, an allyl group and a 3-buten-1-yl group), an aryl group (an aryl group having preferably 6 to 36, more preferably 6 to 18 carbon atoms, such as a phenyl group and a naphthyl group), a heterocyclic group (a heterocyclic group having preferably 1 to 24, more preferably 1 to 12 carbon atoms, such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group and a benzotriazol-1-yl group), an alkoxy group (an alkoxy group having preferably 1 to 36, more preferably 1 to 18 carbon atoms, such as a methoxy group, an ethoxy group, a propyloxy group, a butoxy group, a hexyloxy group, a 2-ethylhexyloxy group, a dodecyloxy group and a cyclohexyloxy group), an aryloxy group (an aryloxy group having preferably 6 to 24, more preferably 1 to 18 carbon atoms, such as a phenoxy group and a naphthyloxy group), an alkylamino group (an alkylamino group having preferably 1 to 36, more preferably 1 to 18 carbon atoms, such as a methylamino group, an ethylamino group, a propylamino group, a butylamino group, a hexylamino group, a 2-ethylhexylamino group, an isopropylamino group, a t-butylamino group, a t-octylamino group, a cyclohexylamino group, an N,N-diethylamino group, an N,N-dipropylamino group, an N,N-dibutylamino group and an N-methyl-N-ethylamino group), an arylamino group (an aryl amino group having preferably 6 to 36, more preferably 6 to 18 carbon atoms, such as a phenylamino group, a naphthylamino group, an N,N-diphenylamino group and an N-ethyl-N-phenylamino group), or a heterocyclic amino group (a heterocyclic amino group having preferably 1 to 24, more preferably 1 to 12 carbon atoms, such as a 2-aminopyrrole group, a 3-aminopyrazole group, a 2-aminopyridine group and a 3-aminopyridine group).

In the formula (III), when the alkyl group, alkenyl group, aryl group, heterocyclic group, alkoxy group, aryloxy group, alkylamino group, arylamino group or heterocyclic amino group represented by $R^8$ or $R^9$ is a group that may further be substituted, it may be substituted by any of Substituent R mentioned above, and when it is substituted by two or more substituents, the substituents may be the same or different.

In the formula (III), $X^3$ represents NR, a nitrogen atom, an oxygen atom or a sulfur atom, $X^4$ represents NRa, an oxygen atom or a sulfur atom, wherein R and Ra each independently represent a hydrogen atom, an alkyl group (a straight chain, branched chain, or cyclic alkyl group having preferably 1 to 36, more preferably 1 to 12 carbon atoms, such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group, a 1-adamantyl group), an alkenyl group (an alkenyl group having preferably 2 to 24, more preferably 2 to 12 carbon atoms, such as a vinyl group, an allyl group and a 3-buten-1-yl group), an aryl group (an aryl group having preferably 6 to 36, more preferably 6 to 18 carbon atoms, such as a phenyl group and a naphthyl group), a heterocyclic group (a heterocyclic group having preferably 1 to 24, more preferably 1 to 12 carbon atoms, such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group and a benzotriazol-1-yl group), an acyl group (an acyl group having preferably 1 to 24, more preferably 2 to 18 carbon atoms, such as an acetyl group, a pivaloyl group, a 2-ethylhexyl group, a benzoyl group and a cyclohexanoyl group), an alkylsulfonyl group (an alkylsulfonyl group having preferably 1 to 24, more preferably 1 to 18 carbon atoms, such as a methylsulfonyl group, a ethylsulfonyl group, a isopropylsulfonyl group and a cyclohexylsulfonyl group), or an arylsulfonyl group (an arylsulfonyl group having preferably 6 to 24, more preferably 6 to 18 carbon atoms, such as a phenylsulfonyl group and a naphthylsulfonyl group).

The alkyl group, alkenyl group, aryl group, heterocyclic group, acyl group, alkylsulfonyl group or arylsulfonyl group for R and Ra may further be substituted by any of Substituent R, and when the group is substituted by plural substituents, the substituents may be the same or different.

In the formula (III), $Y^1$ represents NRc, a nitrogen atom or a carbon atom, $Y^2$ represents a nitrogen atom or a carbon atom, and Rc has the same definition as R for $X^3$.

In the formula (III), $R^8$ and $Y^1$ may bond to each other so that $R^8$, $Y^1$ and the carbon atom form a 5-membered ring (e.g., cyclopentane, pyrrolidine, tetrahydrofuran, dioxolane, tetrahydrothiophene, pyrrole, furan, thiophene, indole, benzofuran and benzothiophene), a 6-membered ring (e.g., cyclohexane, piperidine, piperazine, morpholine, tetrahydropyran, dioxane, pentamethylenesulfide, dithiane, benzene, piperidine, piperazine, pyridazine, quinoline and quinazoline) or a 7-membered ring (e.g., cycloheptane and hexamethyleneimine).

In the formula (III), $R^9$ and $Y^2$ may bond to each other so that $R^9$, $Y^2$ and the carbon atom form a 5-, 6- or 7-membered ring. Examples of the 5-membered, 6-membered and 7-membered rings to be formed include a ring in which one bond in the ring formed by $R^8$, $Y^1$ and the carbon atom has been converted to a double bond.

In the formula (III), when the 5-, 6- or 7-membered ring formed by bonding of $R^8$ and $Y^1$ or $R^9$ and $Y^2$ is a ring that may further be substituted, it may be substituted by any of Substituent R, and when it is substituted by two or more substituents, the substituents may be the same or different.

In the formula (III), $X^5$ represents a group capable of bonding to Ma, and examples thereof include groups as defined for $X^1$ in the formula (II-1).

The a represents 0, 1 or 2.

A preferable embodiment of the compound represented by the formula (III) is shown below.

Namely, it is an embodiment wherein $R^2$ to $R^5$, $R^7$ and Ma are each a preferable embodiment for the complex including the compound represented by the formula (I) and the metal atom or the metal compound, $X^3$ represents NR (R represents a hydrogen atom or an alkyl group), a nitrogen atom or an oxygen atom, $X^4$ represents NRa (Ra represents a hydrogen atom, an alkyl group or a heterocyclic group) or an oxygen atom, $Y^1$ represents NRc (Rc represents a hydrogen atom or an alkyl group), a nitrogen atom or a carbon atom, $Y^2$ represents a nitrogen atom or a carbon atom, $X^5$ represents a group that bonds via an oxygen atom, $R^8$ and $R^9$ each independently represent an alkyl group, an aryl group, a heterocyclic group, an alkoxy group or an alkylamino group, or $R^8$ and $Y^1$ bond to each other to form a 5- or 6-membered ring and $R^9$ and $Y^2$ bond to each other to form a 5- or 6-membered ring, and a represents 0 or 1.

A more preferable embodiment of the compound represented by the formula (III) is shown below.

Namely, it is an embodiment wherein $R^2$ to $R^5$, $R^7$ and Ma are each a preferable embodiment for the complex including the compound represented by the formula (I) and the metal atom or the metal compound, $X^3$ and $X^4$ are each an oxygen atom, $Y^1$ represents NH, $Y^2$ represents an nitrogen atom, $X^5$ represents a group that bonds via an oxygen atom, $R^8$ and $R^9$ each independently represent an alkyl group, an aryl group, a heterocyclic group, an alkoxy group or an alkylamino group, or $R^8$ and $Y^1$ bond to each other to form a 5- or 6-membered ring and $R^9$ and $Y^2$ bond to each other to form a 5- or 6-membered ring, and a represents 0 or 1.

Hereinafter specific examples of the specific complex of the invention are shown, but the invention is not limited to these examples.

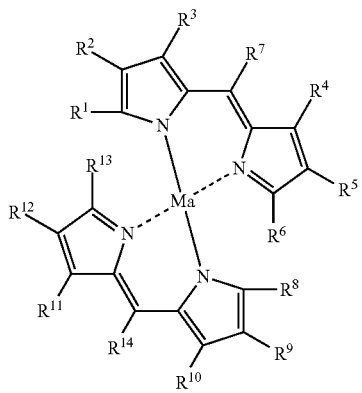

| Compd No. | $R^1 = R^6 = R^8 = R^{13}$ | $R^2 = R^5 = R^9 = R^{12}$ |
|---|---|---|
| Ia-3 | —NH$_2$ | 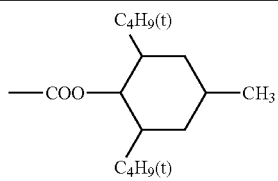 |
| Ia-4 | Same as above | Same as above |
| Ia-5 | —NHCOCH$_3$ | Same as above |
| Ia-6 | Same as above | Same as above |
| Ia-7 | Same as above | Same as above |
| Ia-8 | —NHCOCH$_2$OCH$_2$COOH | Same as above |
| Ia-9 | Same as above | Same as above |
| Ia-10 | Same as above | Same as above |
| Ia-11 | Same as above | Same as above |
| Ia-12 | Same as above | Same as above |
| Ia-13 | —NH$_2$ | Same as above |
| Ia-14 | Same as above | Same as above |
| Ia-15 | Same as above | Same as above |
| Ia-16 | —NHCOCH$_3$ | Same as above |
| Ia-17 | —NH$_2$ | Same as above |
| Ia-18 | Same as above | Same as above |
| Ia-19 | Same as above | Same as above |
| Ia-20 | Same as above | Same as above |
| Ia-21 | —NHCOCH$_3$ | Same as above |
| Ia-22 | —NHCOCH$_2$OCH$_2$COOH | Same as above |
| Ia-23 | Same as above | Same as above |
| Ia-24 | —NHCOCH$_2$OCH$_2$COOH | 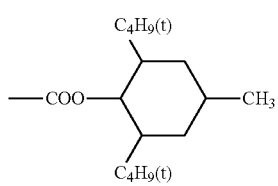 |
| Ia-25 | Same as above | Same as above |
| Ia-26 | Same as above | Same as above |
| Ia-27 | 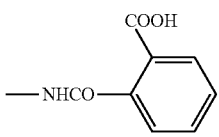 | Same as above |
| Ia-28 | Same as above | Same as above |
| Ia-29 | 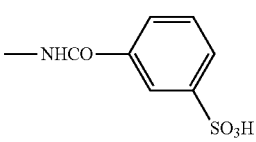 | Same as above |

-continued

| | | |
|---|---|---|
| Ia-30 | Same as above | Same as above |
| Ia-31 | 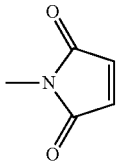 | Same as above |
| Ia-32 | 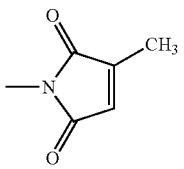 | Same as above |
| Ia-33 | —NHSO$_2$CH$_3$ | Same as above |
| Ia-34 | 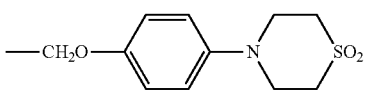 | Same as above |
| Ia-35 | 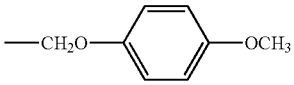 | 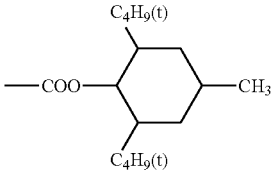 |
| Ia-36 | 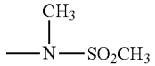 | Same as above |
| Ia-37 | 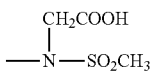 | Same as above |
| Ia-38 | —Cl | Same as above |
| Ia-39 | —S—CH$_2$COOH | Same as above |
| Ia-40 | 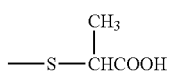 | Same as above |
| Ia-41 | Same as above | Same as above |
| Ia-42 | —SO$_2$CH$_3$ | Same as above |
| Ia-43 | Same as above | Same as above |
| Ia-44 | 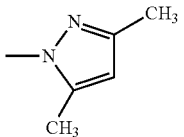 | Same as above |
| Ia-45 | —CH$_3$ | Same as above |
| Ia-46 | Same as above | Same as above |
| Ia-47 | Same as above | Same as above |
| Ia-48 | Same as above | Same as above |
| Ia-49 | —C$_4$H$_9$(t) | Same as above |
| Ia-50 | Same as above | Same as above |
| Ia-51 | —CH$_2$CH$_2$COOH | Same as above |

-continued

| | | |
|---|---|---|
| Ia-52 | —CH₂CH₂COOH | —COO—[cyclohexyl with 2,6-di-C₄H₉(t) and 4-CH₃] |
| Ia-53 | —CH₃ | Same as above |
| Ia-54 | Same as above | Same as above |
| Ia-55 | Same as above | Same as above |
| Ia-56 | Same as above | Same as above |
| Ia-57 | —C₆H₅ (phenyl) | Same as above |
| Ia-58 | Same as above | Same as above |
| Ia-59 | —C₆H₄—COOH (4-carboxyphenyl) | Same as above |
| Ia-60 | Same as above | —COOCH₂—CH(C₆H₁₃)C₈H₁₇ |
| Ia-61 | 3-(NHCOCH₂CH₂COOH)-phenyl | —COOCH₂—CH(C₂H₅)C₄H₉ |
| Ia-62 | 2-pyridyl | —COO—[cyclohexyl with 2,6-di-C₄H₉(t) and 4-CH₃] |
| Ia-63 | —CH₃ | Same as above |
| Ia-67 | —NH₂ | —CN |
| Ia-68 | —NHCOCH₃ | Same as above |
| Ia-69 | —CH₃ | Same as above |
| Ia-70 | Same as above | Same as above |
| Ia-71 | —C₁₃H₂₇ | Same as above |
| Ia-72 | —NH₂ | Same as above |
| Ia-73 | —NHCOCH₂OCH₂COOH | Same as above |
| Ia-74 | —NHCO—CH(C₄H₉)—CHO—C₆H₄—N(thiomorpholine-1,1-dioxide) | Same as above |
| Ia-75 | —C₆H₄—CO—N(CH₂CH₂OCH₃)₂ | Same as above |
| Ia-76 | Same as above | Same as above |
| Ia-77 | Same as above | Same as above |
| Ia-78 | —NHCOCH₂OCH₂COOH | Same as above |
| Ia-79 | 2-pyridyl | —COO—[cyclohexyl with 2,6-di-C₄H₉(t) and 4-CH₃] |
| Ia-80 | Same as above | Same as above |

-continued

| Compd | | |
|---|---|---|
| Ia-81 | —$C_{13}H_{27}$ | Same as above |
| Ia-82 | —$NHCOCH_2OCH_2COOH$ | —$COOC_2H_5$ |
| Ia-83 | 3-methylphenyl-$SO_2$—N($CH_2COOH$)($CH_2COOH$) | —COO-(2,6-di-t-$C_4H_9$-4-$CH_3$-cyclohexyl) |
| Ia-A | —$NHCOCH_3$ | —COO-(2,6-di-t-$C_4H_9$-4-$CH_3$-cyclohexyl) |

| Compd No. | $R^3 = R^4 = R^{10} = R^{11}$ | $R^7 = R^{14}$ | Ma |
|---|---|---|---|
| Ia-3 | —$CH_3$ | —H | Zn |
| Ia-4 | Same as above | Same as above | V=O |
| Ia-5 | Same as above | Same as above | Zn |
| Ia-6 | Same as above | Same as above | Cu |
| Ia-7 | Same as above | —$CH_3$ | Zn |
| Ia-8 | Same as above | Same as above | Zn |
| Ia-9 | Same as above | Same as above | Zn |
| Ia-10 | —$C_3H_7$(iso) | —H | Zn |
| Ia-11 | Same as above | —$CH_3$ | Zn |
| Ia-12 | —$C_4H_9$(t) | —H | Cu |
| Ia-13 | Same as above | —$CH_3$ | Zn |
| Ia-14 | Same as above | —H | Zn |
| Ia-15 | cyclohexyl | Same as above | Zn |
| Ia-16 | —$CH_2S$—$CH(CH_3)COOH$ | —$CH_3$ | Cu |
| Ia-17 | phenyl | —H | Zn |
| Ia-18 | Same as above | Same as above | Cu |
| Ia-19 | Same as above | Same as above | V=O |
| Ia-20 | Same as above | —$CH_3$ | Zn |
| Ia-21 | Same as above | Same as above | Zn |
| Ia-22 | Same as above | —H | Zn |
| Ia-23 | Same as above | —$CH_3$ | Zn |
| Ia-24 | methylphenyl | —$CH_3$ | Cu |
| Ia-25 | 4-chlorophenyl | Same as above | Zn |
| Ia-26 | 2-methylphenyl | Same as above | Zn |
| Ia-27 | —$CH_3$ | —H | Cu |
| Ia-28 | Same as above | —$CH_3$ | Zn |
| Ia-29 | Same as above | Same as above | Cu |

-continued

| | | | |
|---|---|---|---|
| Ia-30 | —CH$_2$—CH(C$_2$H$_5$)C$_4$H$_9$ | Same as above | Cu |
| Ia-31 | 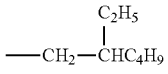 phenyl | Same as above | Zn |
| Ia-32 | Same as above | Same as above | Zn |
| Ia-33 | —CH$_3$ | Same as above | Zn |
| Ia-34 | Same as above | Same as above | Zn |
| Ia-35 | 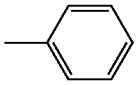 phenyl | —CH$_3$ | Zn |
| Ia-36 | Same as above | Same as above | Zn |
| Ia-37 | Same as above | Same as above | Zn |
| Ia-38 | Same as above | Same as above | Cu |
| Ia-39 | Same as above | Same as above | Cu |
| Ia-40 | —CH$_3$ | Same as above | Cu |
| Ia-41 | Same as above | Same as above | V=O |
| Ia-42 | Same as above | Same as above | V=O |
| Ia-43 | 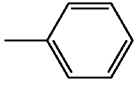 phenyl | Same as above | Cu |
| Ia-44 | Same as above | Same as above | Cu |
| Ia-45 | —CH$_3$ | —H | Cu |
| Ia-46 | Same as above | —CH$_3$ | Zn |
| Ia-47 | Same as above | Same as above | Cu |
| Ia-48 | Same as above | Same as above | Ni |
| Ia-49 | Same as above | Same as above | Zn |
| Ia-50 | Same as above | Same as above | Pd |
| Ia-51 | Same as above | Same as above | Zn |
| Ia-52 | 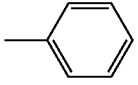 phenyl | —CH$_3$ | Zn |
| Ia-53 | Same as above | Same as above | Zn |
| Ia-54 | 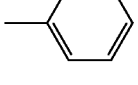 4-COOH-phenyl | Same as above | Zn |
| Ia-55 | Same as above | Same as above | Cu |
| Ia-56 | Same as above | 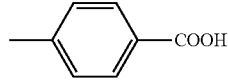 phenyl | Zn |
| Ia-57 | —CH$_3$ | —H | Zn |
| Ia-58 | Same as above | —CH$_3$ | Zn |
| Ia-59 | 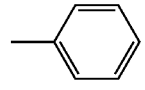 —CH$_2$O-(4-(thiomorpholine-1,1-dioxide)phenyl) | Same as above | Zn |
| Ia-60 | 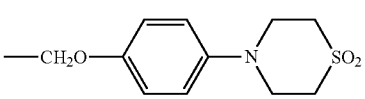 —CH$_2$CH$_2$—O-(4-OCH$_3$-phenyl) | Same as above | Zn |

-continued

| | | | |
|---|---|---|---|
| Ia-61 | Same as above | Same as above | Zn |
| Ia-62 | Same as above | Same as above | Zn |
| Ia-63 | Same as above | Same as above | Cu |
| Ia-67 | —CH₃ | —H | Zn |
| Ia-68 | Same as above | —CH₃ | Zn |
| Ia-69 | Same as above | Same as above | Zn |
| Ia-70 | 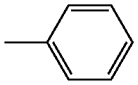 | Same as above | Zn |
| Ia-71 | —CH₃ | 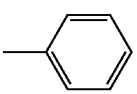 | Cu |
| Ia-72 | —CF₃ | Same as above | Cu |
| Ia-73 | Same as above | Same as above | Cu |
| Ia-74 | Same as above | —CH₃ | Zn |
| Ia-75 | —C₃H₇(iso) | Same as abov | Zn |
| Ia-76 | 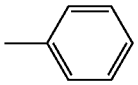 | Same as above | Zn |
| Ia-77 | —CF₃ | Same as above | Zn |
| Ia-78 | 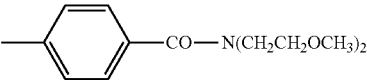 | Same as above | Zn |
| Ia-79 | 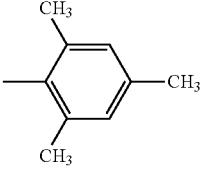 | —H | Zn |
| Ia-80 | —C₄H₉(t) | Same as above | Zn |
| Ia-81 | 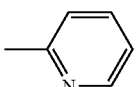 | Same as above | Zn |
| Ia-82 | 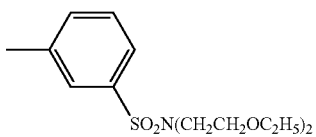 | Same as above | Cu |
| Ia-83 | —CH₃ | Same as above | Zn |
| Ia-A | —CH₃ | 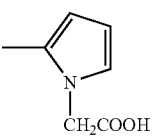 | Zn |

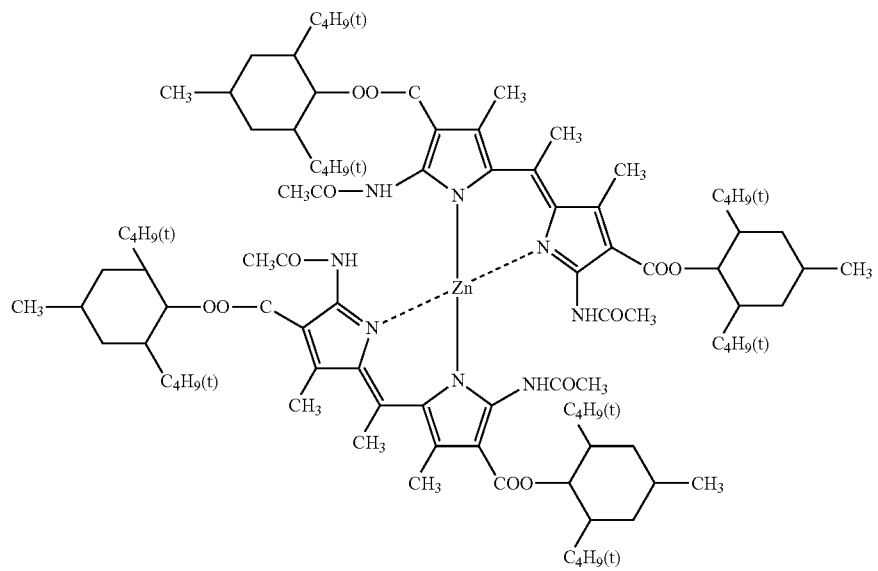
IIa-1
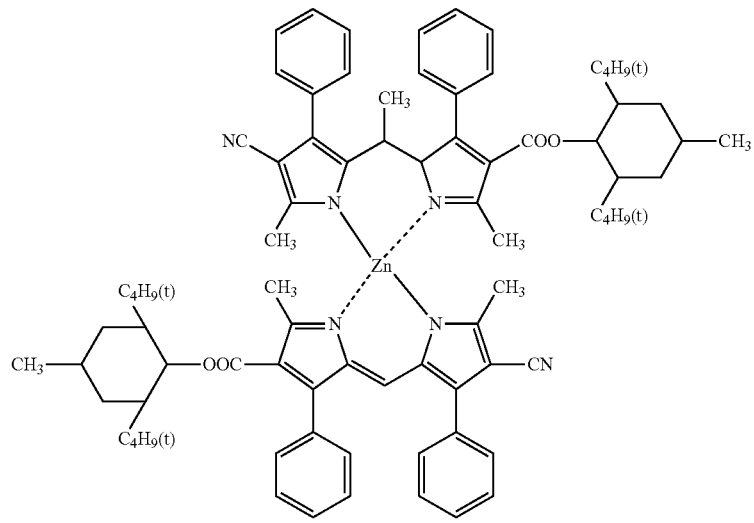
IIa-2
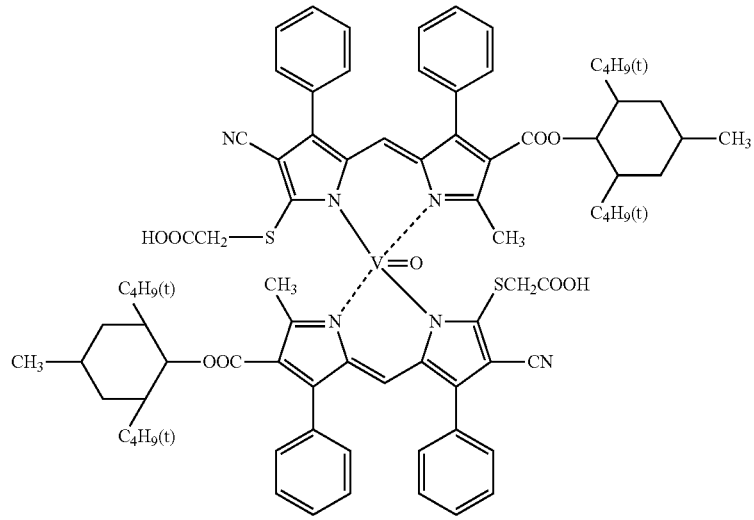
IIa-3

IIa-4
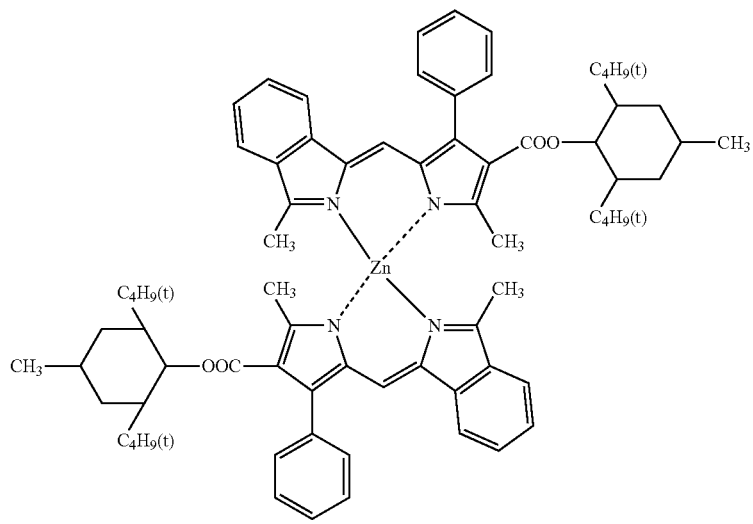
IIa-5
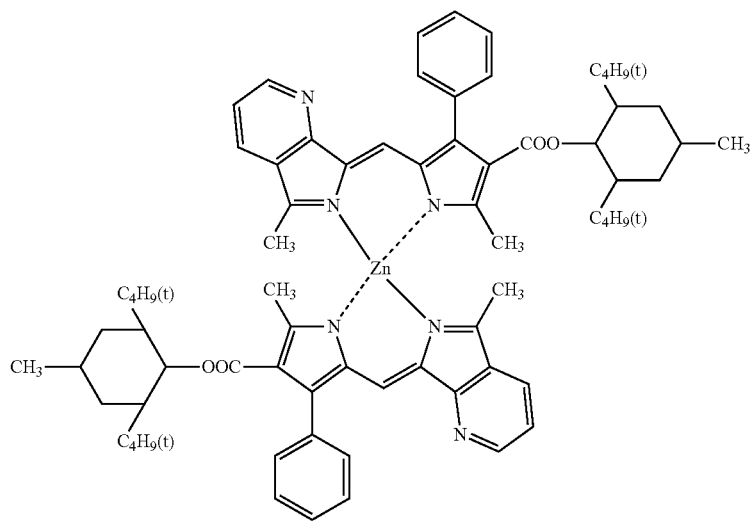
IIa-6
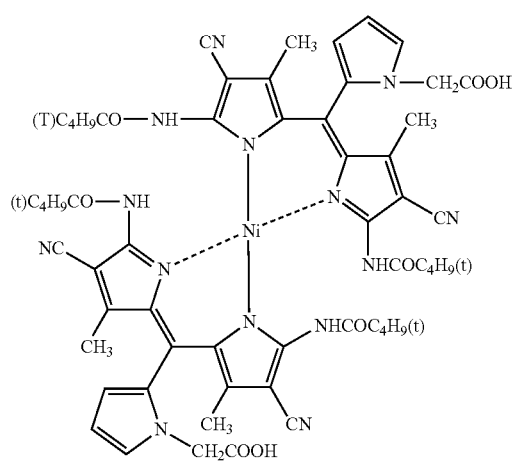

-continued
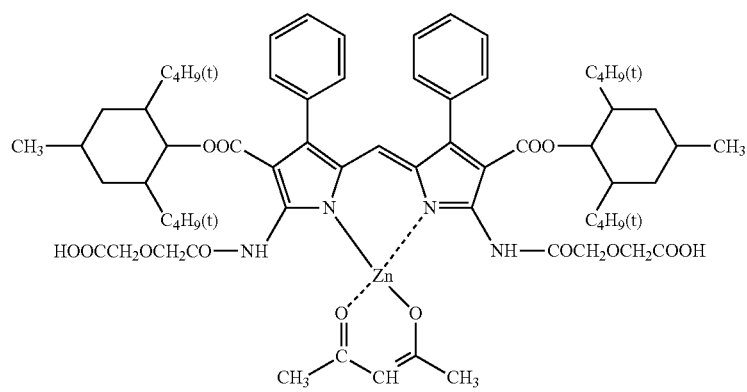
IIa-7
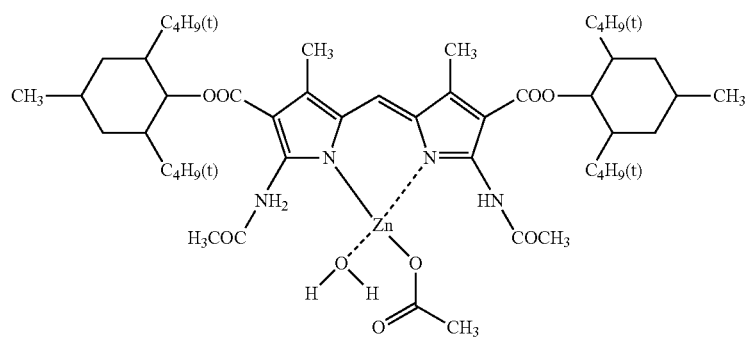
IIa-8
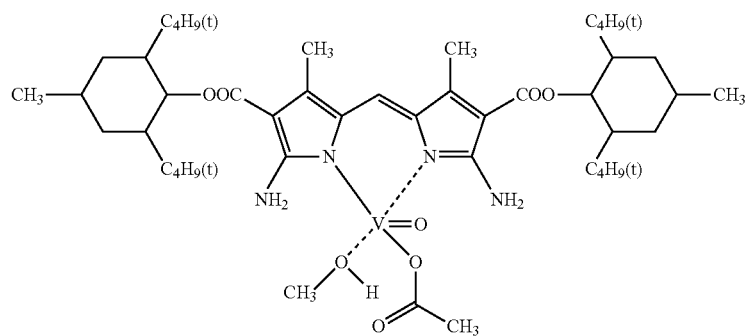
IIa-10
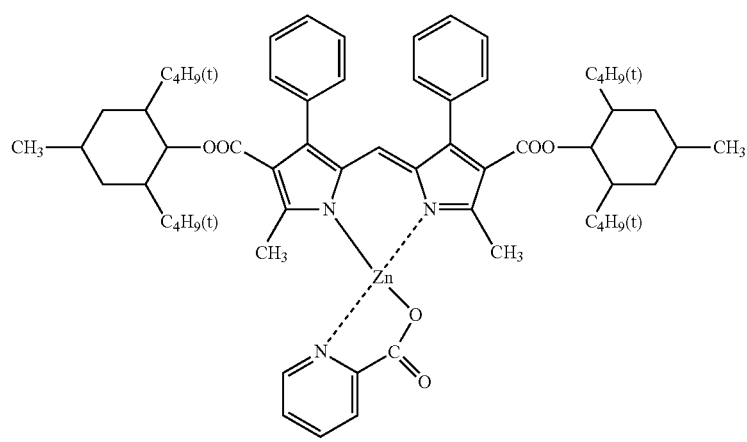
IIa-11

-continued
IIa-12
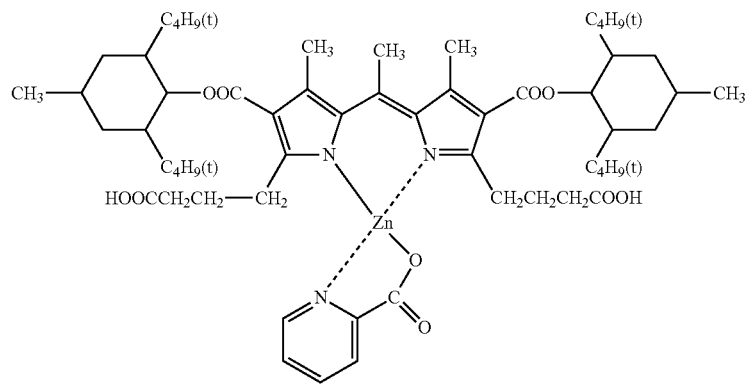
IIa-13
IIa-14
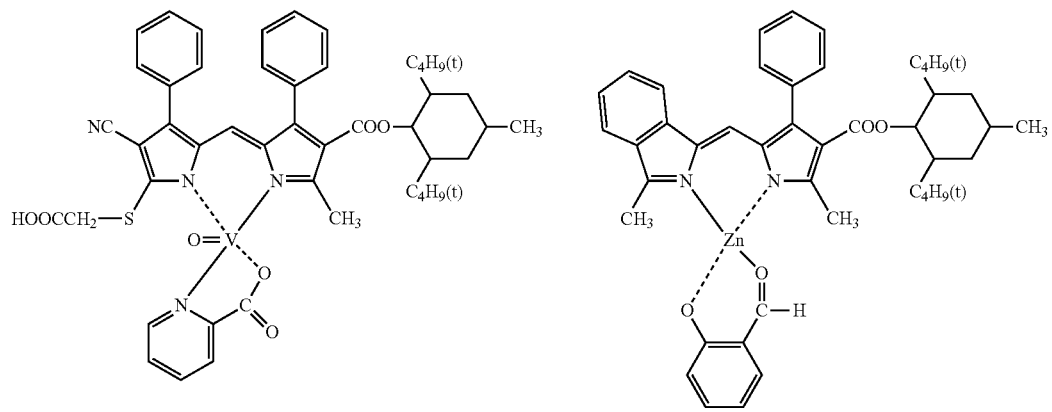
IIa-15
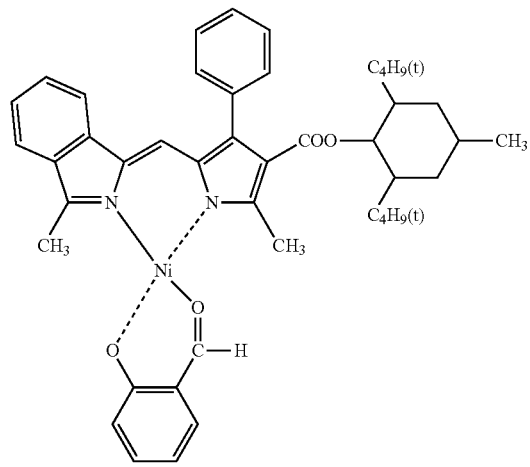
IIa-16
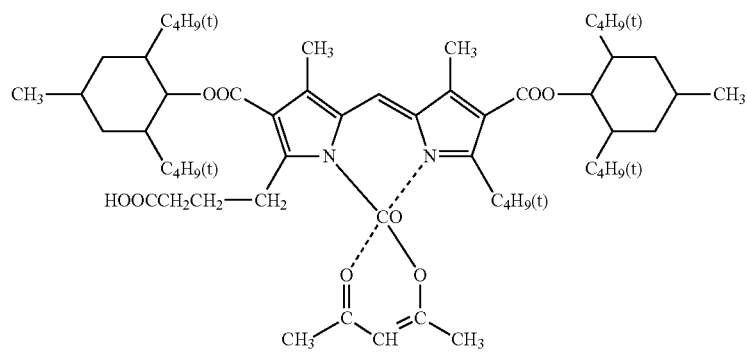

-continued
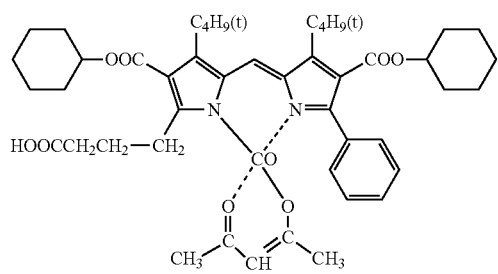
IIa-17
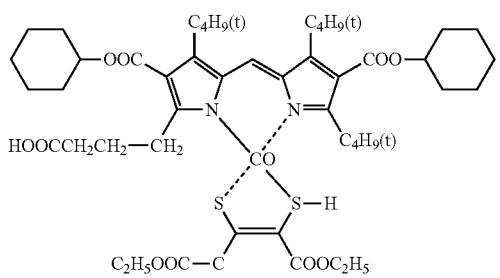
IIa-18
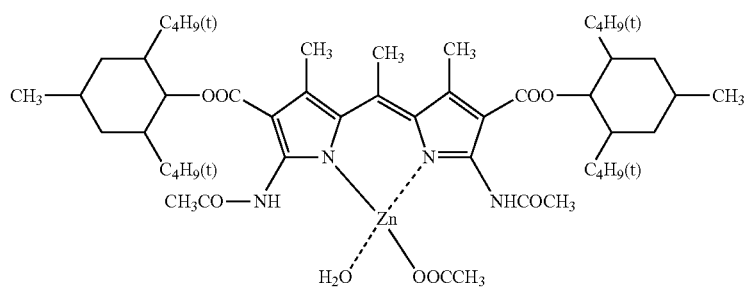
IIa-19
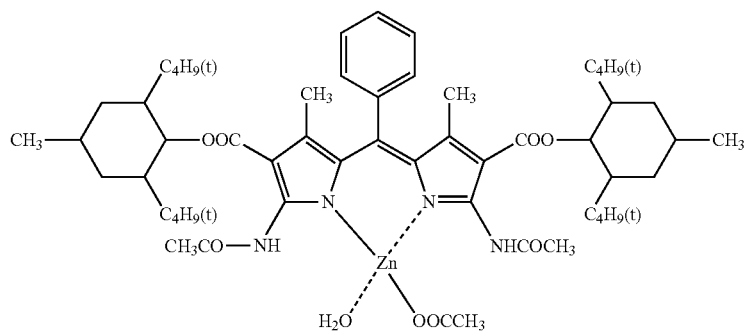
IIa-20
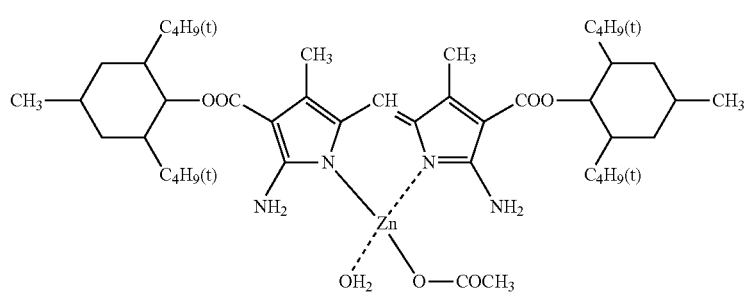
I-1
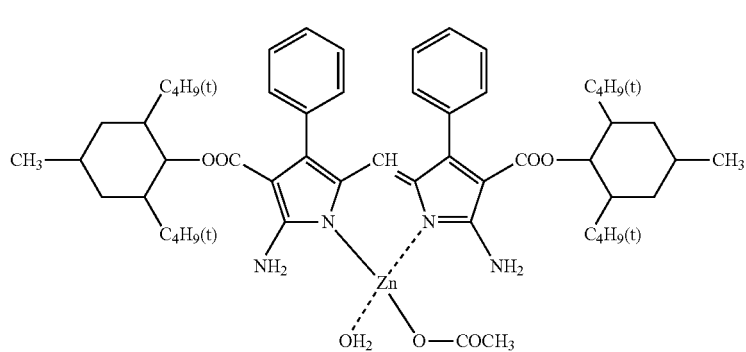
I-2

-continued
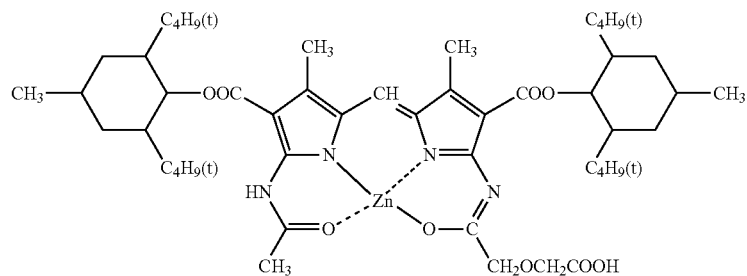
I-3
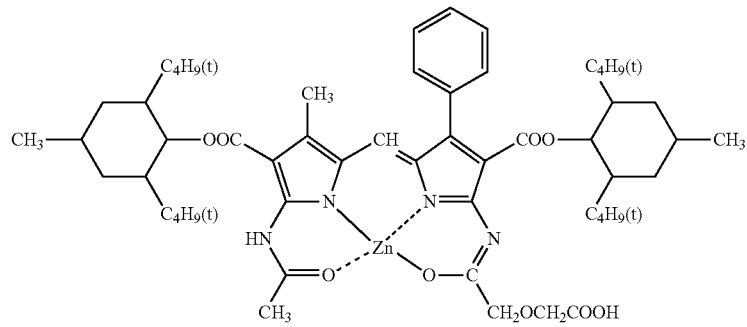
I-4
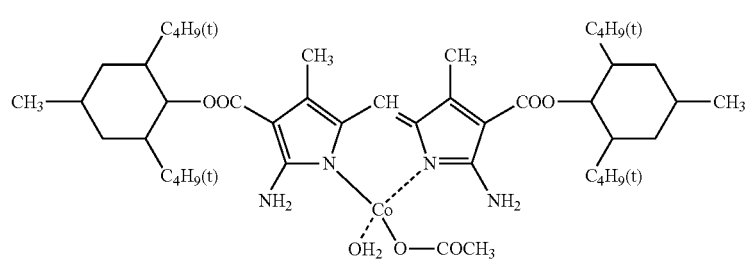
I-5
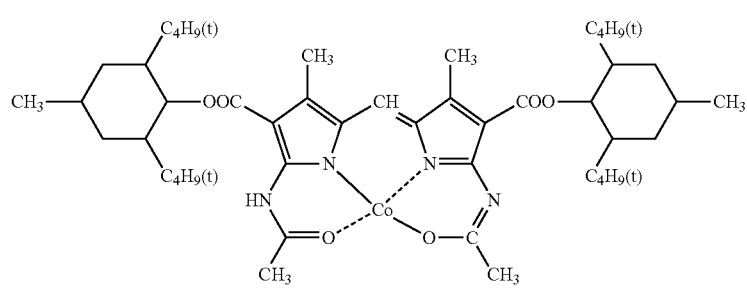
I-6
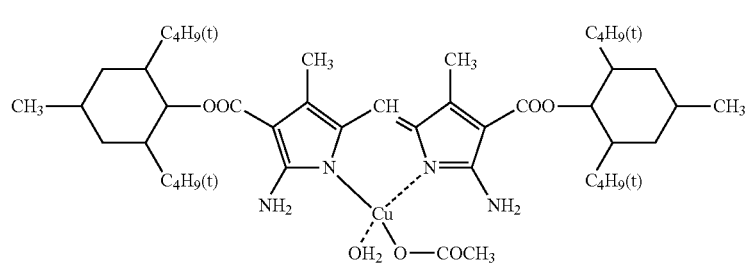
I-7

-continued
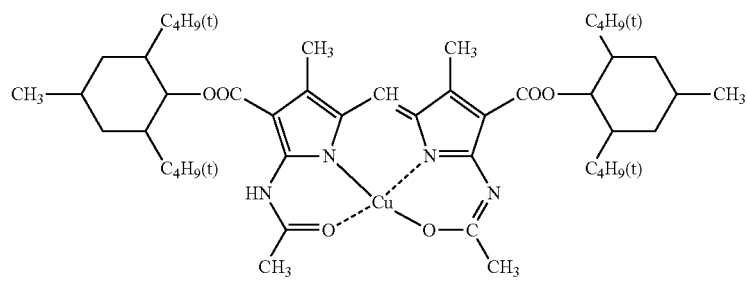
I-8
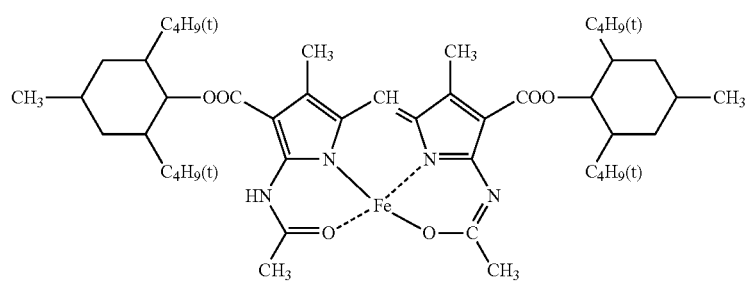
I-9
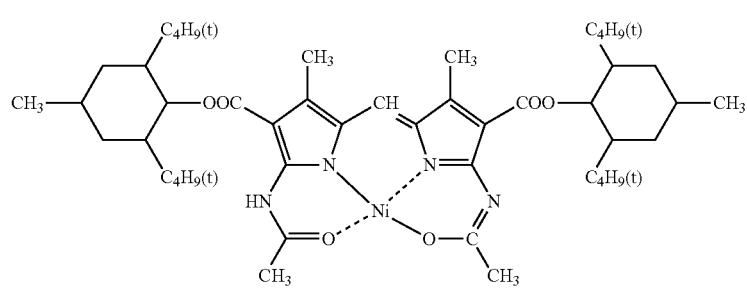
I-10
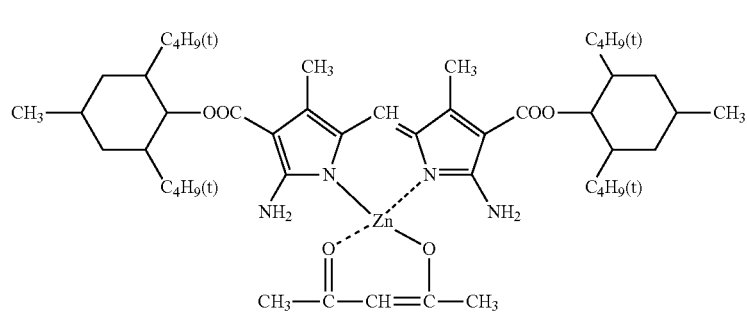
I-11
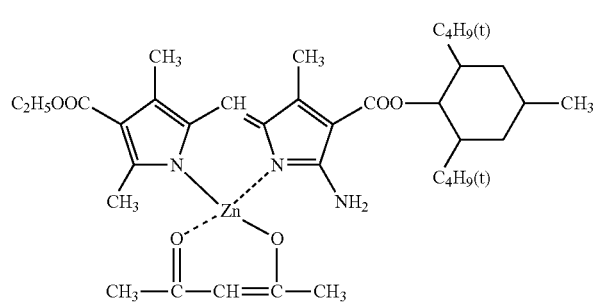
I-12

-continued
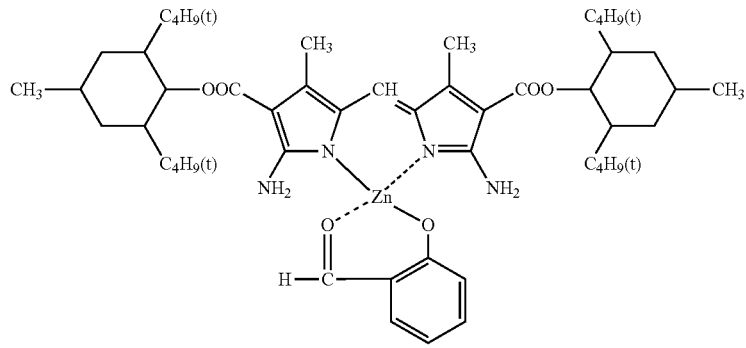
I-13
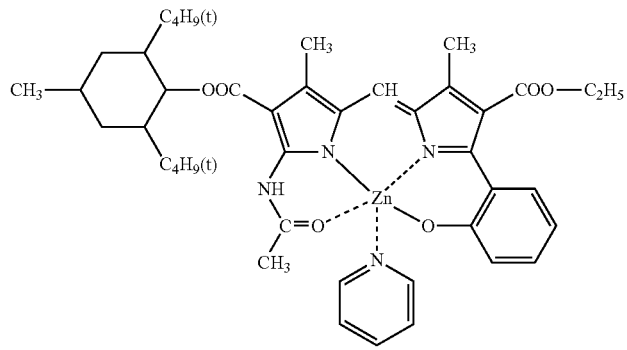
I-14
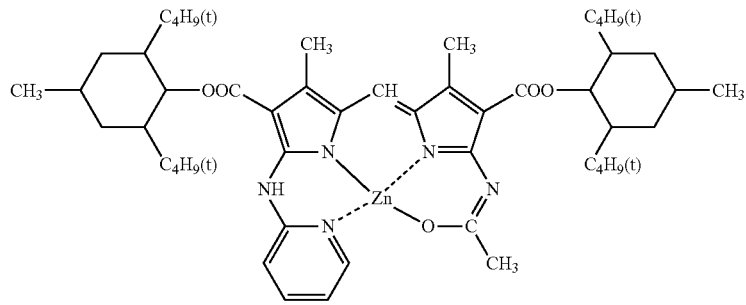
I-15
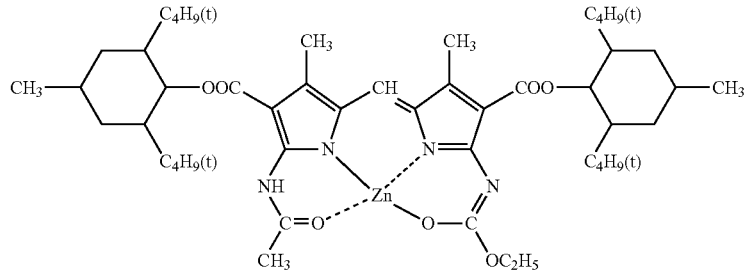
I-16
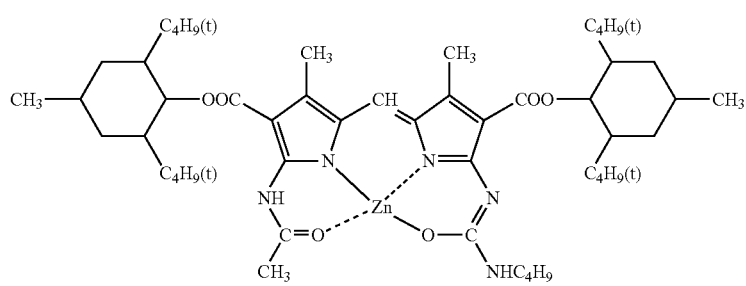
I-17

-continued
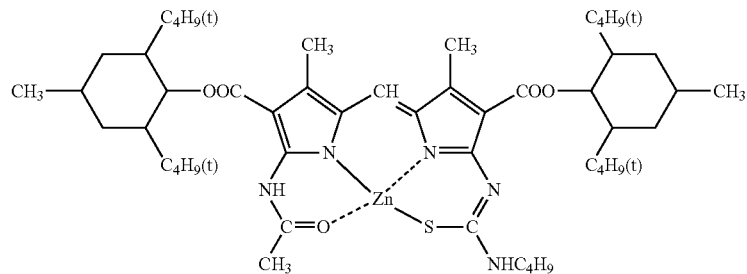
I-18
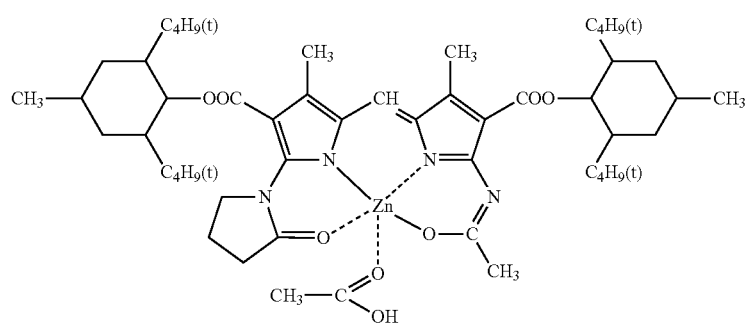
I-19
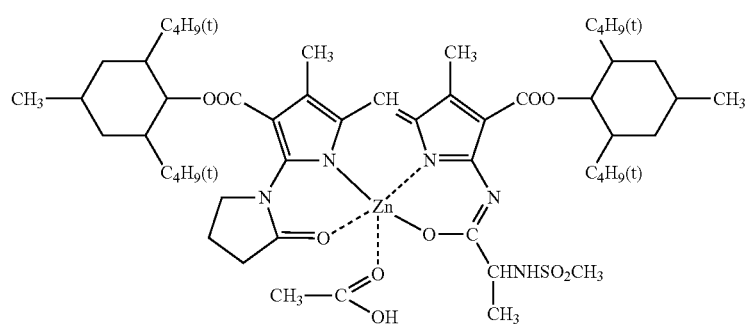
I-20
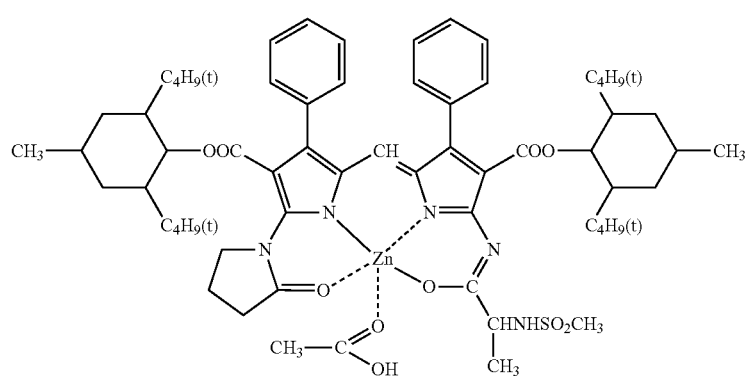
I-21

I-22
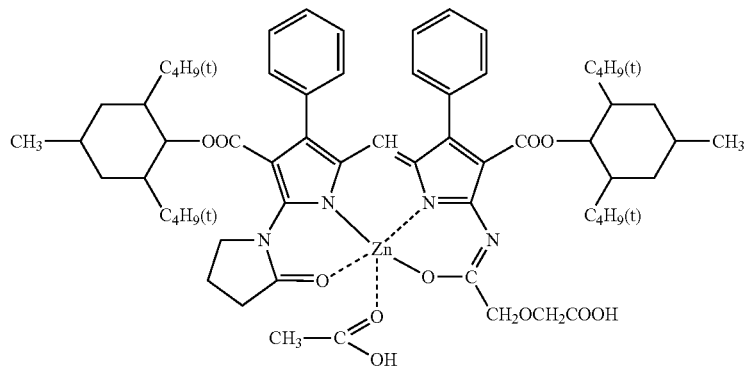
I-23
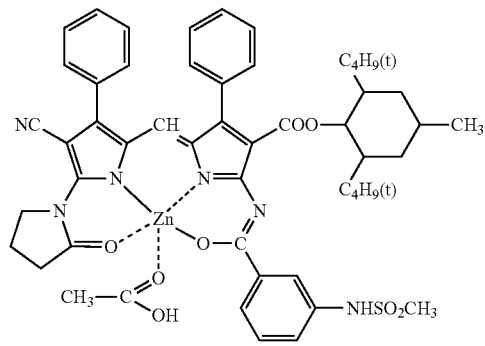
I-24
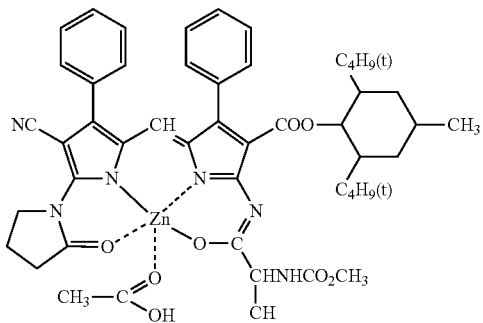
I-25
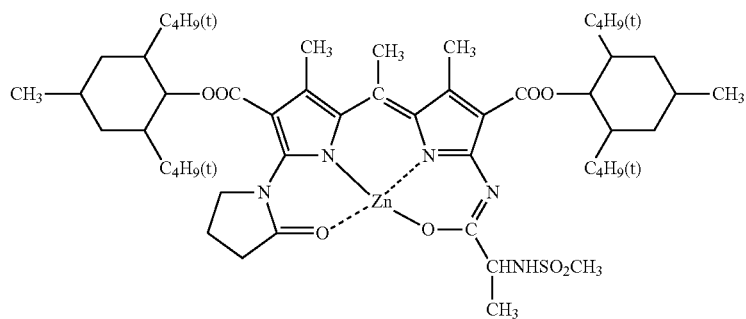
I-26
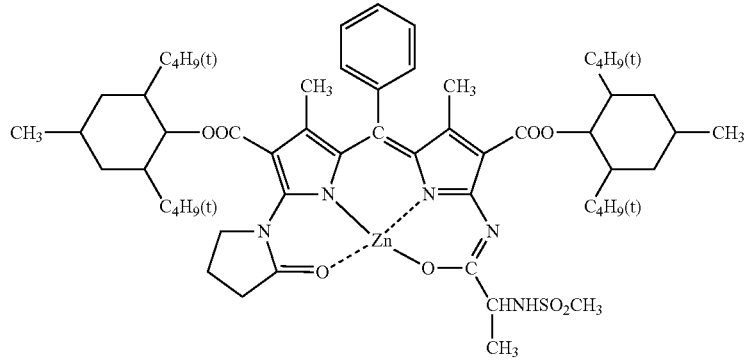

-continued
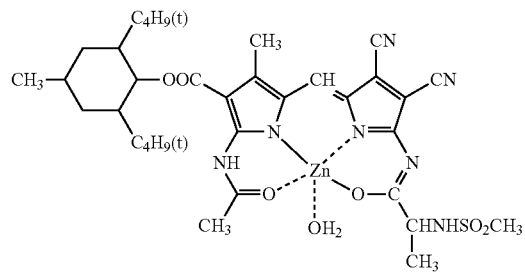
I-27
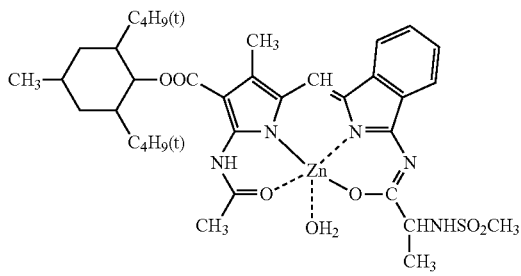
I-28
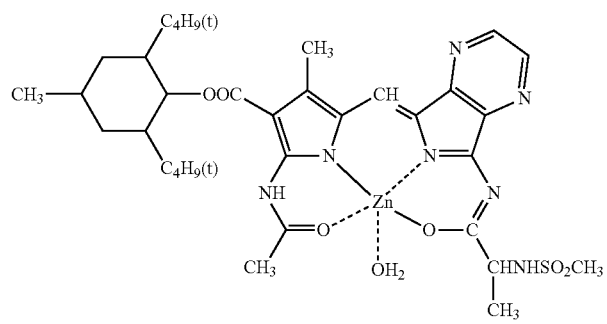
I-29
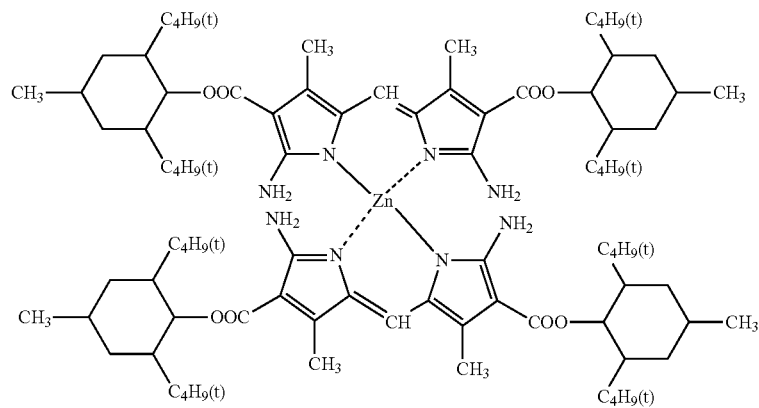
I-30
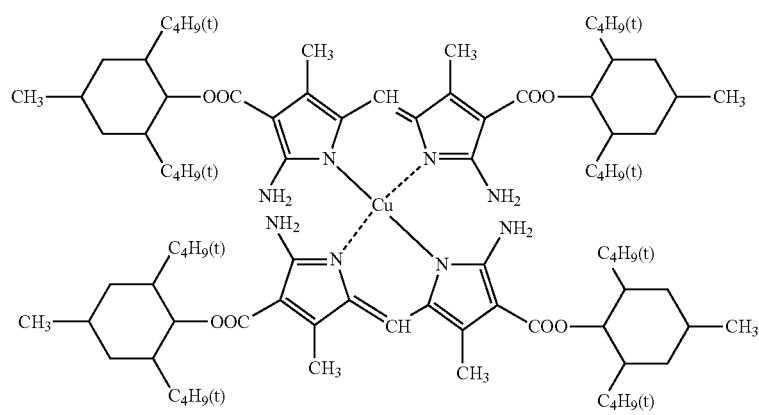
I-31

-continued
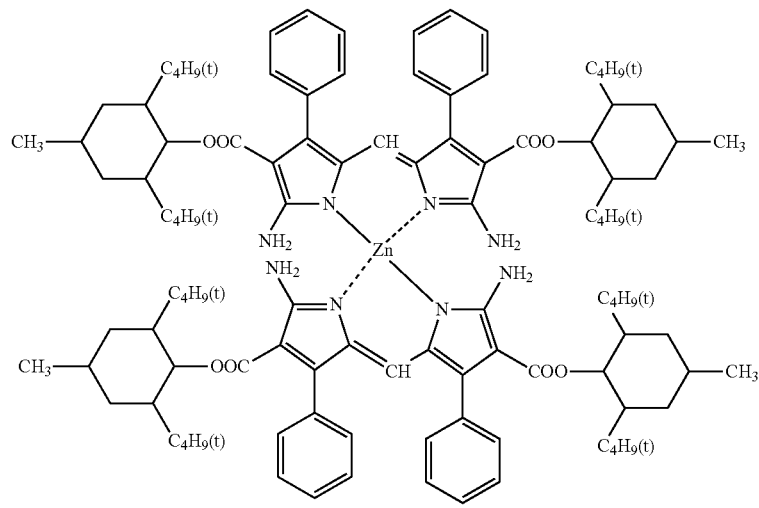
I-32
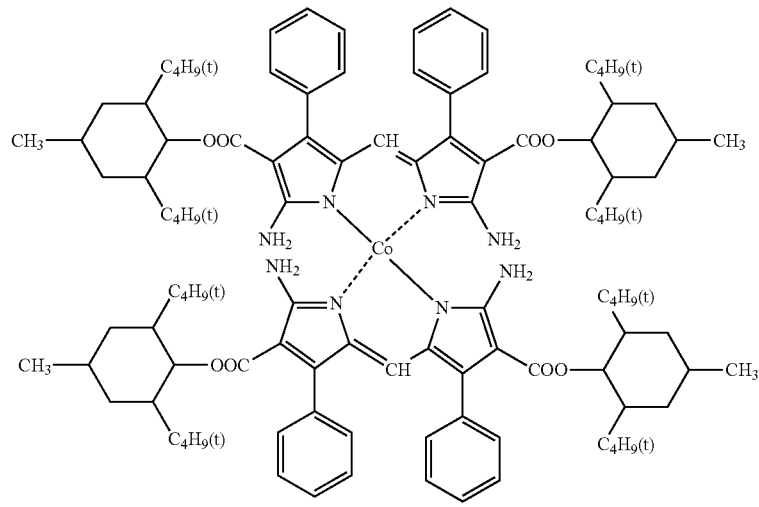
I-33
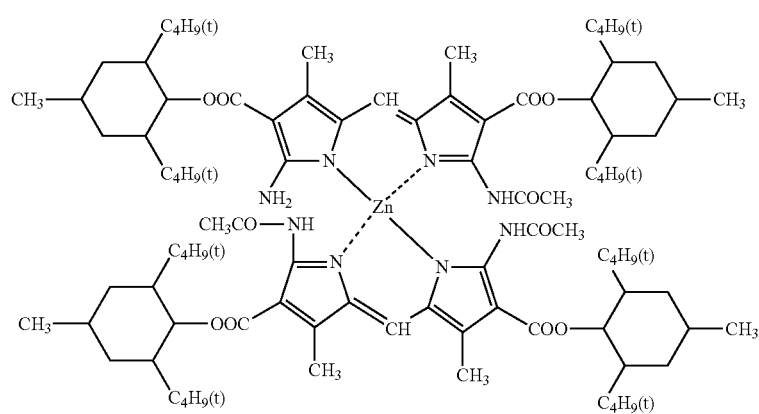
I-34

I-35
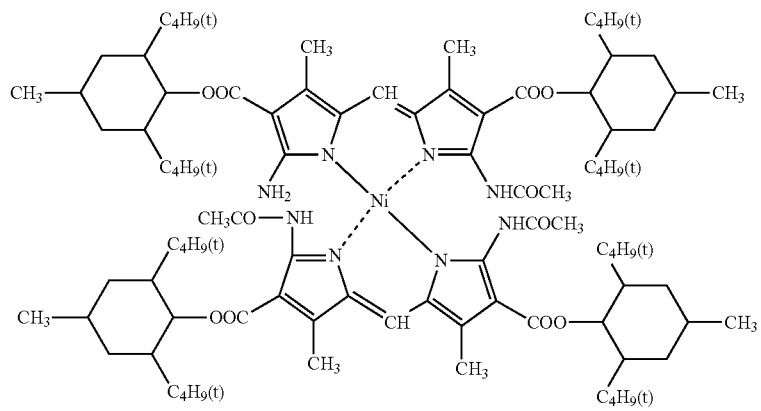
I-36
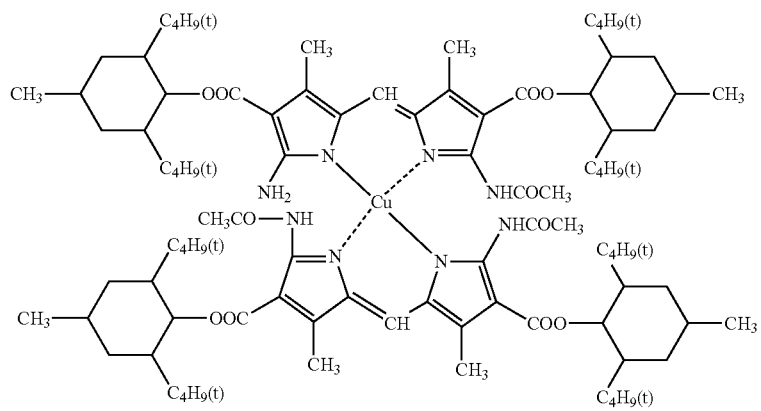
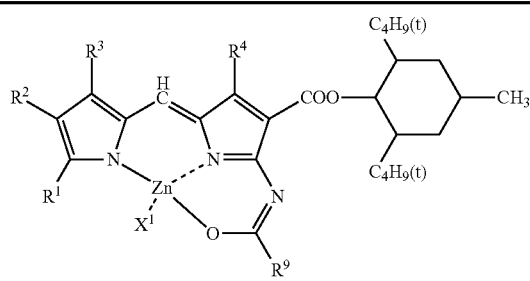
| Compd No. | R$^1$ | R$^2$ | R$^3$ | R$^4$ | R$^9$ | X$^1$ |
|---|---|---|---|---|---|---|
| II-1 | —CH$_3$ | —COOC$_2$H$_5$ | —CH$_3$ | —CH$_3$ | —CH$_3$ | H$_2$O |
| II-2 | Same as above | Same as above | Same as above | Same as above | —CH(CH$_3$)NHSO$_2$CH$_3$ | Same as above |
| II-3 | Same as above | Same as above | Same as above | Same as above | 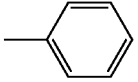 | Same as above |
| II-4 | 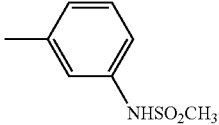 | —COOCH$_3$ | Same as above | 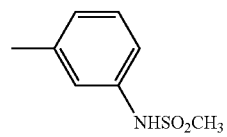 | —CH$_3$ | Same as above |

-continued

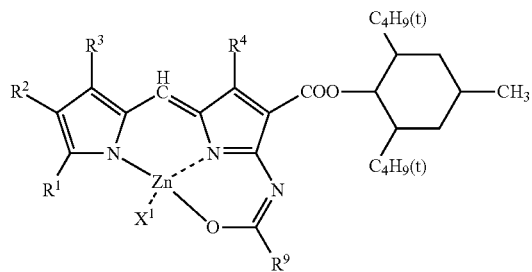

| Compd No. | R¹ | R² | R³ | R⁴ | R⁹ | X¹ |
|---|---|---|---|---|---|---|
| II-5 | 3-(NHSO₂CH₃)-phenyl | —COOC₂H₅ | Same as above | Same as above | —CH₂OCH₂COOH | Same as above |
| II-6 | Same as above | Same as above | Same as above | Same as above | —CH₃ | Same as above |
| II-7 | —CH₃ | —COOC₂H₅ | phenyl | phenyl | —CH₃ | H₂O |
| II-8 | 3-pyridyl | Same as above | Same as above | Same as above | Same as above | Same as above |
| II-9 | 3-(NHSO₂CH₃)-phenyl | —CN | —CH₃ | —CH₃ | Same as above | Same as above |
| II-10 | 3-(NHSO₂CH₃)-phenyl | Same as above | Same as above | Same as above | 3-(NHSO₂CH₃)-phenyl | Same as above |
| II-11 | Same as above | Same as above | phenyl | phenyl | —CH₃ | Same as above |

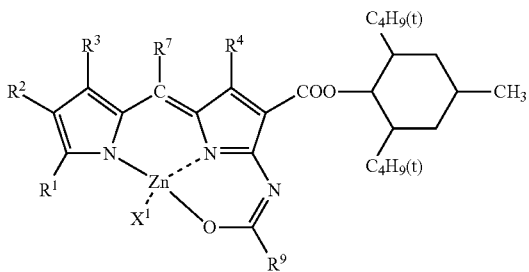

| Compound No. | R¹ | R² | R³ | R⁴ | R⁷ | R⁹ | X¹ |
|---|---|---|---|---|---|---|---|
| II-A | —CH$_3$ | —COOC$_2$H$_5$ | —CH$_3$ | —CH$_3$ | 2-methyl-1-(CH$_2$COOH)-pyrrolyl | —CH$_3$ | H$_2$O |

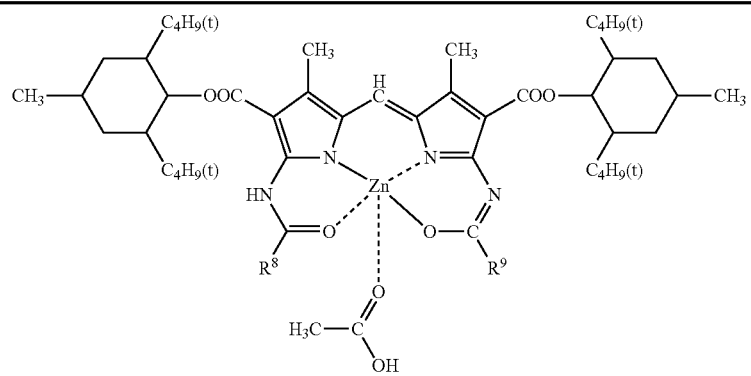

| Compd No. | R⁸ | R⁹ | Compd No. | R⁸ | R⁹ |
|---|---|---|---|---|---|
| III-1 | —CH$_3$ | —CH$_3$ | III-2 | —CH(C$_2$H$_5$)C$_4$C$_9$ | —CH$_3$ |
| III-3 | —C$_4$H$_9$(t) | Same as above | III-4 | —CH(C$_2$H$_5$)C$_4$C$_9$ | —CH(C$_2$H$_5$)C$_4$H$_9$ |
| III-5 | —C$_4$H$_9$(t) | —C$_4$H$_9$(t) | III-6 | —cyclohexyl | —CH$_3$ |
| III-7 | —CH(CH$_3$)S—C$_4$H$_9$ | —CH$_3$ | III-8 | —CH$_2$OCH$_3$ | Same as above |
| III-9 | —CH(C$_2$H$_5$)—O—C$_6$H$_4$—OCH$_3$ | Same as above | III-10 | —CH(C$_2$H$_5$)—O—C$_6$H$_4$—N(morpholinyl-SO$_2$) | Same as above |
| III-11 | —CH(CH$_3$)—S—CH$_2$COOC$_2$H$_5$ | Same as above | III-12 | —C(CH$_3$)=CH$_2$ | Same as above |

-continued

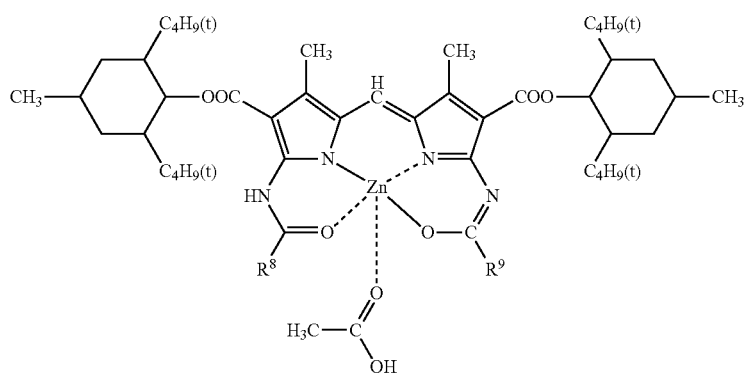

| Compd No. | R⁸ | R⁹ | Compd No. | R⁸ | R⁹ |
|---|---|---|---|---|---|
| III-13 | —C(CH₃)(CH₃)—COOCH₃ | Same as above | III-14 | —CO—CH(CH₃)—COCH₃ | Same as above |
| III-15 | —CH₂OCH₂COOC₂H₅ | Same as above | III-16 | —CH₂NHSO₂CH₃ | Same as above |
| III-17 | —CH(CH₃)NHSO₂CH₃ | Same as above | III-18 | —CH(C₂H₅)NHSO₂CH₃ | Same as above |
| III-19 | —CH(C₄H₉)NHSO₂CH₃ | Same as above | III-20 | —CH(CH(CH₃)₂)NHSO₂CH₃ | Same as above |
| III-21 | —CH(CH₃)NHSO₂—C₄H₉ | Same as above | III-22 | —CH(CH₃)NHSO₂—C₆H₄—CH₃ | Same as above |
| III-23 | —CH(CH₃)NHSO₂—C₆H₄—NHSO₂CH₃ | Same as above | III-24 | —CH(CH₃)NHSO₂—N(C₂H₅)₂ | Same as above |
| III-25 | —CH(CH₃)—N(phthalimide) | —CH₃ | III-26 | —CH₂CH₂COOC₂H₅ | —CH₃ |
| III-27 | —CH(CH₃)—S—C₆H₄—COOCH₃ | Same as above | III-28 | —CH(CH₃)—S—(2-pyridyl) | Same as above |

-continued

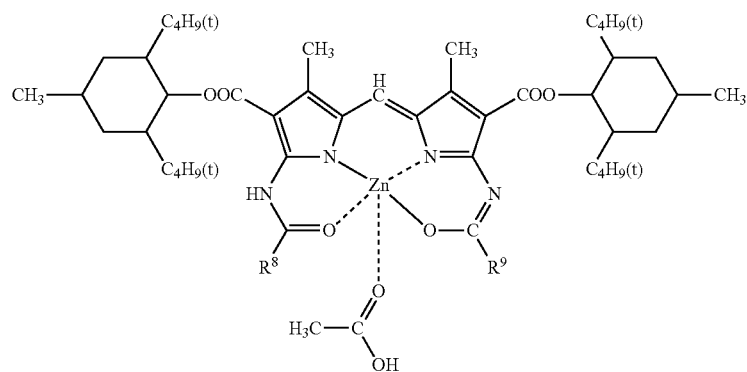

| Compd No. | R⁸ | R⁹ | Compd No. | R⁸ | R⁹ |
|---|---|---|---|---|---|
| III-29 | —CH₂NHSO₂CH₃ | —CH₂NHSO₂CH₃ | III-30 | —CH₂—CH(CH₃)NHSO₂CH₃ | —CH₂—CH(CH₃)NHSO₂CH₃ |
| III-31 | —CH₂NHSO₂CH₃ | —CH(C₂H₅)C₄H₉ | III-32 | —CH₂—CH(CH₃)NHSO₂CH₃ | —C₄H₉(t) |
| III-33 | phenyl | —CH₃ | III-34 | phenyl | —CH₂—CH(CH₃)NHSO₂CH₃ |
| III-35 | 4-C₄H₉(t)-phenyl | —CH₃ | III-36 | 3-NHSO₂CH₃-phenyl | —CH₃ |
| III-37 | 2-NHSO₂CH₃-phenyl | Same as above | III-38 | 3-NHSO₂-phenyl-phenyl | Same as above |
| III-39 | 2-OH-phenyl | Same as above | III-40 | 2-OCH₃-phenyl | Same as above |
| III-41 | 3-SO₂NH₂-phenyl | Same as above | III-42 | 3-SO₂N(CH₃)₂-phenyl | Same as above |
| III-43 | 4-SCH₃-phenyl | Same as above | III-44 | 4-SO₂CH₃-phenyl | Same as above |

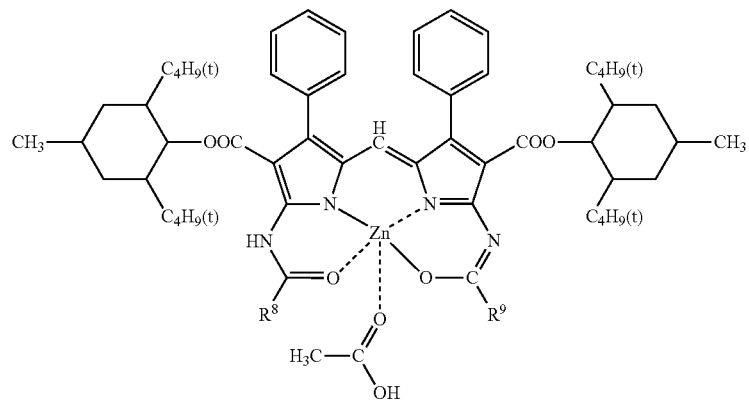

| Compd No. | R⁸ | R⁹ | Compd No. | R⁸ | R⁹ |
|---|---|---|---|---|---|
| III-45 | —CH₃ | —CH₃ | III-46 | —CH(C₂H₅)C₄H₉ | —CH(C₂H₅)C₄H₉ |
| III-47 | —C₄H₉(t) | —C₄H₉(t) | III-48 | cyclohexyl | cyclohexyl |
| III-49 | —CH₂NHSO₂CH₃ | —CH₃ | III-50 | —CH₂NHSO₂CH₃ | —CH₂NHSO₂CH₃ |
| III-51 | —CH(CH₃)NHSO₂CH₃ | Same as above | III-52 | —CH(CH₃)NHSO₂CH₃ | —CH(CH₃)NHSO₂CH₃ |
| III-53 | —CH(C₄H₉)NHSO₂CH₃ | Same as above | III-54 | 3-(NHSO₂CH₃)phenyl | —CH₃ |
| III-55 | 3-(NHSO₂CH₃)phenyl | 3-(NHSO₂CH₃)phenyl | III-56 | 3-(SO₂NHCOCH₃)phenyl | Same as above |
| III-57 | 2,4,6-trimethylphenyl | —CH₃ | III-58 | 2,4,6-trimethylphenyl | 2,4,6-trimethylphenyl |
| III-59 | 2-(OCH₂CH₂OH)phenyl | Same as above | III-60 | 3-(COOCH₃)phenyl | —CH₃ |
| III-61 | 3,5-dimethoxyphenyl (2-methyl-3,5-dimethoxy shown) | Same as above | III-62 | 2-(NHSO₂CH₃)phenyl | Same as above |

-continued

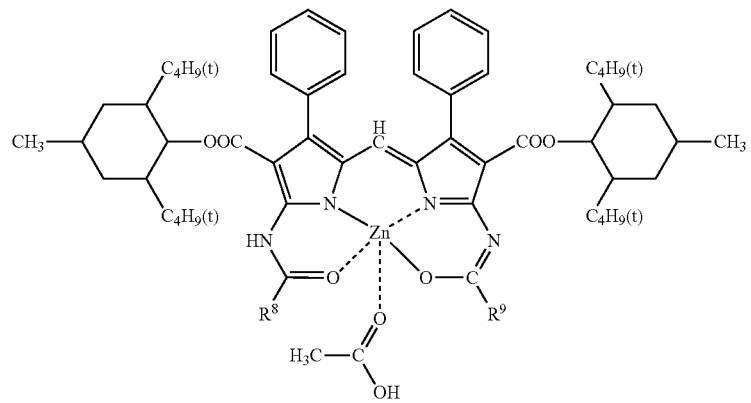

| Compd No. | R⁸ | R⁹ | Compd No. | R⁸ | R⁹ |
|---|---|---|---|---|---|
| III-63 | 2-pyridyl | Same as above | III-64 | 2-pyridyl | 2-pyridyl |

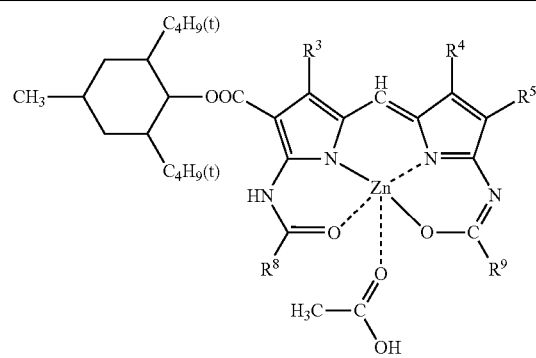

| Compd No. | $R^3$ | $R^4$ | $R^5$ | $R^8$ | $R^9$ |
|---|---|---|---|---|---|
| III-65 | —CH₃ | —CH₃ | —COOC₂H₅ | —CH₃ | —CH₃ |
| III-66 | Same as above | Same as above | Same as above | —CH(CH₃)NHSO₂CH₃ | —CH(CH₃)NHSO₂CH₃ |
| III-67 | Same as above | Same as above | Same as above | 3-(NHSO₂CH₃)phenyl | 3-(NHSO₂CH₃)phenyl |
| III-68 | phenyl | Same as above | Same as above | —CH₃ | —CH₃ |
| III-69 | phenyl | phenyl | Same as above | Same as above | Same as above |

-continued

| | | | | | |
|---|---|---|---|---|---|
| III-70 | —CH₃ | (phenyl) | —COO-(2,6-di-t-Bu-4-methylcyclohexyl) | Same as above | —CH₂NHSO₂-(4-methylphenyl) |
| III-71 | (phenyl) | (phenyl) | —CO—N(CH₃)CH₃ | —CH₃ | —CH₂NHSO₂-(4-methylphenyl) |
| III-72 | Same as above | Same as above | —CO—N(C₃H₇(iso))C₃H₇(iso) | Same as above | Same as above |
| III-73 | Same as above | Same as above | —CONH-(cyclohexyl) | Same as above | Same as above |
| III-74 | Same as above | Same as above | —CONH-(2,4,6-trimethylphenyl) | Same as above | Same as above |
| III-75 | Same as above | Same as above | —CON(CH₃)(phenyl) | Same as above | Same as above |

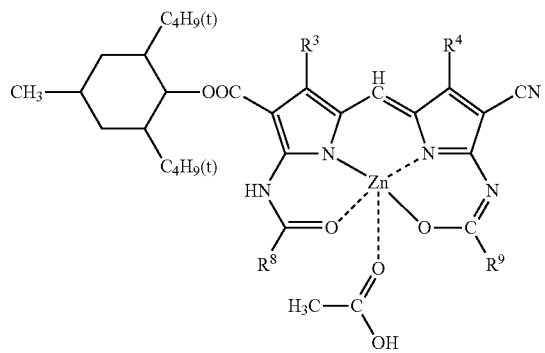

| Compd No. | $R^3$ | $R^4$ | $R^8$ | $R^9$ |
|---|---|---|---|---|
| III-76 | —CH₃ | —CH₃ | —CH₃ | —CH₃ |
| III-77 | Same as above | Same as above | —CH(CH₃)NHSO₂CH₃ | Same as above |
| III-78 | Same as above | Same as above | Same as above | —CH(CH₃)NHSO₂CH₃ |
| III-79 | Same as above | Same as above | —CH(CH₃)NHSO₂CH₃ | —CH(CH₃)NHSO₂CH₃ |
| III-80 | Same as above | (phenyl) | —CH₃ | —CH₃ |
| III-81 | Same as above | Same as above | Same as above | —CH(CH₃)NHSO₂CH₃ |
| III-82 | Same as above | Same as above | —CH(CH₃)NHSO₂CH₃ | Same as above |

-continued

| | | | | |
|---|---|---|---|---|
| III-83 | —CH₃ | (phenyl) | —CHNHSO₂CH₃ \| CH₃ | —CHNHSO₂CH₃ \| CH₃ |
| III-84 | Same as above | Same as above | Same as above | (3-NHSO₂CH₃-phenyl) |
| III-85 | Same as above | Same as above | —C₄H₉(t) | Same as above |
| III-86 | (phenyl) | —CH₃ | —CH₃ | —CH₃ |
| III-87 | Same as above | Same as above | —CH₂NHSO₂CH₃ | —CH₂NHSO₂CH₃ |
| III-88 | (phenyl) | (phenyl) | —CH₃ | —CH₃ |
| III-89 | —CH₃ | (3-NHSO₂CH₃-phenyl) | Same as above | Same as above |

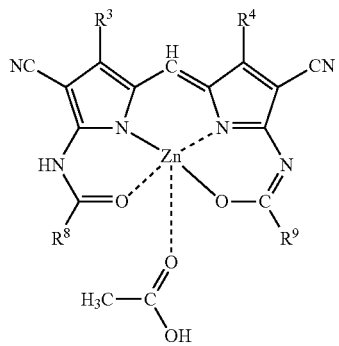

| Compd No. | R³ | R⁴ | R⁸ | R⁹ |
|---|---|---|---|---|
| III-90 | —CH₃ | —CH₃ | —CH₃ | —CH₃ |
| III-91 | Same as above | Same as above | Same as above | —CHNHSO₂CH₃ \| C₄H₉ |
| III-92 | Same as above | Same as above | —CHNHSO₂CH₃ \| C₄H₉ | Same as above |
| III-93 | (phenyl) | (phenyl) | —CH₃ | —CH₃ |
| III-94 | Same as above | Same as above | —C₄H₉(t) | —C₄H₉(t) |
| III-95 | Same as above | Same as above | —CHNHSO₂CH₃ \| C₄H₉ | Same as above |

-continued

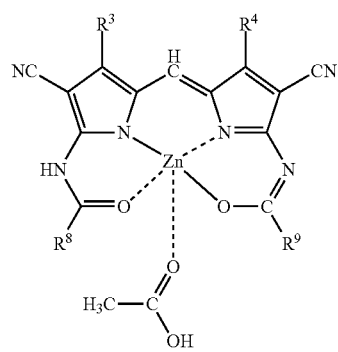

| Compd No. | R³ | R⁴ | R⁸ | R⁹ |
|---|---|---|---|---|
| III-96 | Same as above | Same as above | ![3-NHSO₂C₈H₁₇-phenyl] | —CH₃ |
| III-97 | ![3-NHSO₂CH₃-phenyl] | ![3-NHSO₂CH₃-phenyl] | —CH₃ | —CH₃ |
| III-98 | ![2-CH₃-phenyl] | ![2-CH₃-phenyl] | —CH₃ | —CH₃ |
| III-99 | ![2,4-diCl-phenyl] | ![2,4-diCl-phenyl] | Same as above | Same as above |
| III-100 | ![4-OCH₃-phenyl] | ![4-OCH₃-phenyl] | Same as above | Same as above |
| III-101 | ![2-pyridyl] | ![2-pyridyl] | Same as above | Same as above |
| III-102 | —CHC₂H₅ with CH₃ | —CHC₂H₅ with CH₃ | —CHNHSO₂CH₃ with C₄H₉ | —CHNHSO₂CH₃ with C₄H₉ |
| III-103 | ![3-pyridyl] | ![3-pyridyl] | ![3-NHSO₂C₈H₁₇-phenyl] | ![3-NHSO₂C₈H₁₇-phenyl] |

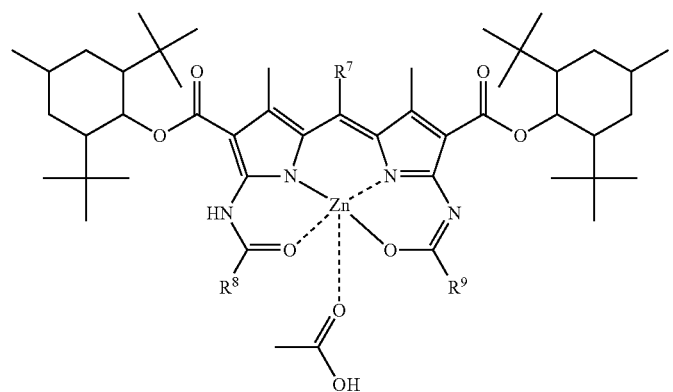
| Compound No. | R⁷ | R⁸ | R⁹ |
| --- | --- | --- | --- |
| III-A | ![pyrrole-CH₂COOH] | —C₄H₉(t) | —C₄H₉(t) |
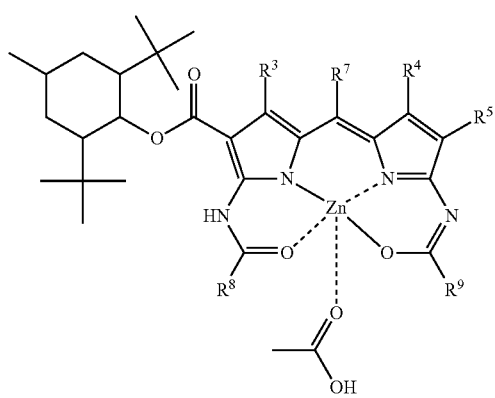
| Compd No. | R³ | R⁴ | R⁵ | R⁷ | R⁸ | R⁹ |
| --- | --- | --- | --- | --- | --- | --- |
| III-B | —CH₃ | —CH₃ | —COOC₂H₅ | ![pyrrole-CH₂COOH] | —CH₃ | —CH₃ |

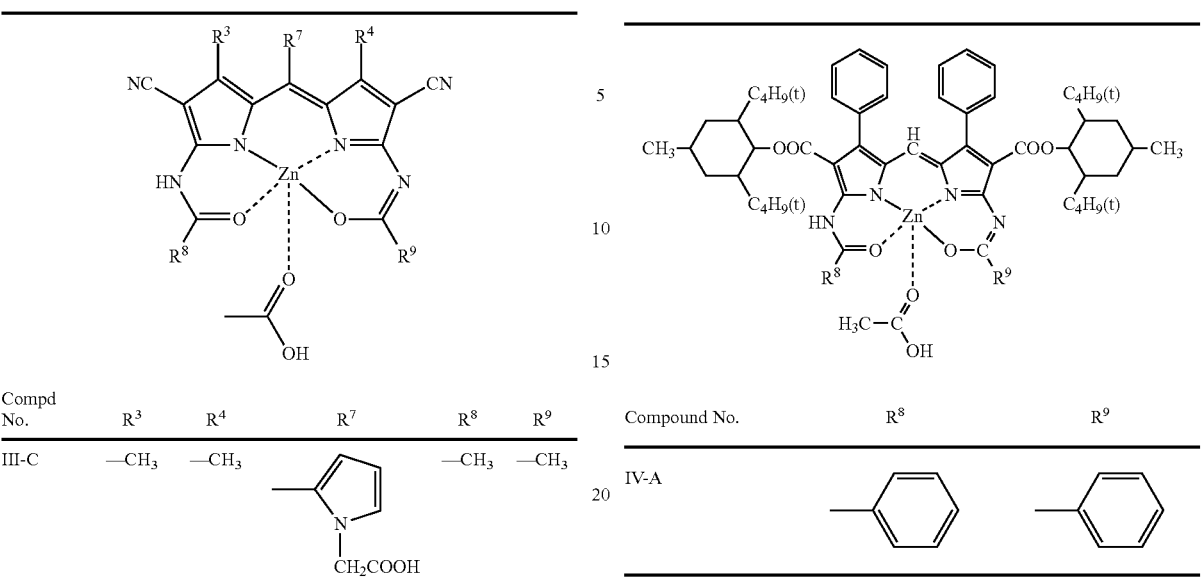
| Compd No. | R³ | R⁴ | R⁷ | R⁸ | R⁹ |
|---|---|---|---|---|---|
| III-C | —CH₃ | —CH₃ | (2-methylpyrrol-1-yl)-CH₂COOH | —CH₃ | —CH₃ |
| Compound No. | R⁸ | R⁹ |
|---|---|---|
| IV-A | phenyl | phenyl |
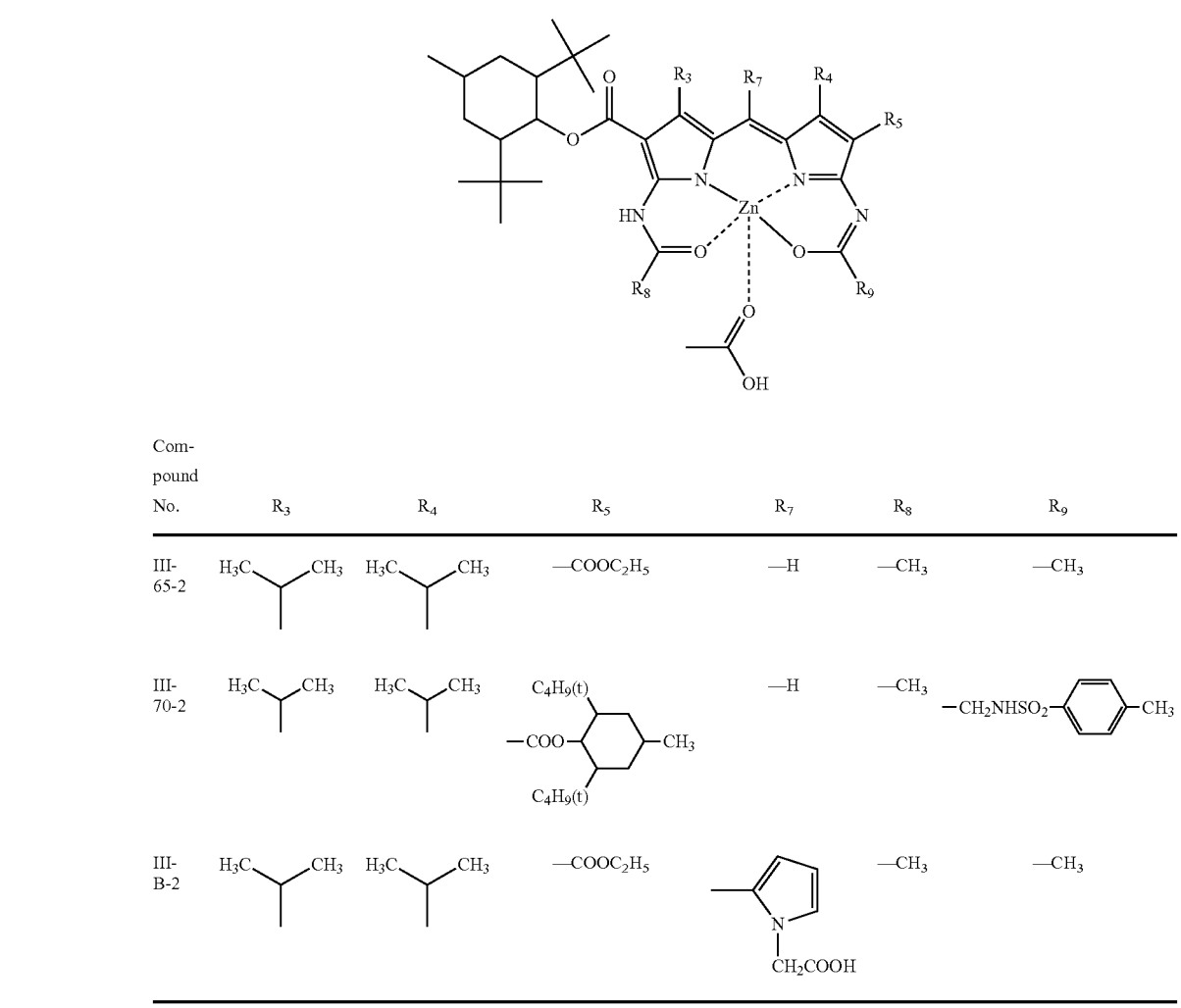
| Compound No. | $R_3$ | $R_4$ | $R_5$ | $R_7$ | $R_8$ | $R_9$ |
|---|---|---|---|---|---|---|
| III-65-2 | isopropyl | isopropyl | —COOC₂H₅ | —H | —CH₃ | —CH₃ |
| III-70-2 | isopropyl | isopropyl | —COO-(2,6-di-t-butyl-4-methylcyclohexyl) | —H | —CH₃ | —CH₂NHSO₂-C₆H₄-CH₃ |
| III-B-2 | isopropyl | isopropyl | —COOC₂H₅ | (2-methylpyrrol-1-yl)-CH₂COOH | —CH₃ | —CH₃ |

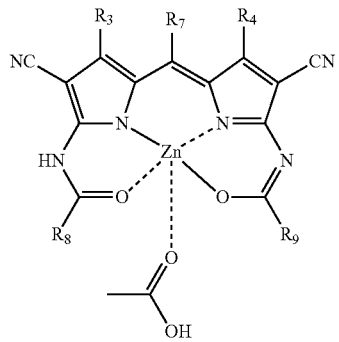

| Compound No. | R₃ | R₄ | R₇ | R₈ | R₉ |
|---|---|---|---|---|---|
| III-90-2 | H₃C-CH(CH₃) | H₃C-CH(CH₃) | —H | —CH₃ | —CH₃ |
| III-C-2 | H₃C-CH(CH₃) | H₃C-CH(CH₃) | pyrrole-CH₂COOH | —CH₃ | —CH₃ |

It is preferable that the mol absorption coefficient of the specific complex of the invention is as high as possible in view of film thickness. The maximum absorption wavelength λmax is preferably 520 nm to 580 nm, more preferably 530 nm to 570 nm in view of color purity. The maximum absorption wavelength and mol absorption coefficient are measured by a spectrophotometer (trade name: UV-2400PC, manufactured by Shimadzu Corporation).

It is preferable that the melting point of the specific complex of the invention is not too high in view of solubility.

The specific complex of the invention may be synthesized by the methods described in U.S. Pat. Nos. 4,774,339 and 5,433,896, JP-A Nos. 2001-240761 and 2002-155052, Japanese Patent No. 3614586, Aust. J. Chem, 1965, 11, 1835-1845, J. H. Boger et al, Heteroatom Chemistry, Vol. 1, No. 5, 389 (1990), and the like.

With respect to the synthesis method of the specific complex in the invention, the method described in the paragraphs [0131] to [0157] of JP-A No. 2008-292970 may be specifically applied.

In the photosensitive colored curable composition of the invention, one kind of the specific complex may be used, or two or more kinds thereof may be used in combination.

The content of the specific complex in the invention in the colored curable composition differs according to molecular weight and mol absorption coefficient, and is preferably 10 mass % to 70 mass %, more preferably 10 mass % to 50 mass %, and most preferably 15 mass % to 30 mass % with respect to all the solid components in the colored curable composition.

[(A-2) Phthalocyanine Pigment]

The phthalocyanine pigment used in the invention is not specifically limited so long as it is a pigment having a phthalocyanine backbone. The center metal included in the phthalocyanine pigment may be any metal capable of constituting a phthalocyanine backbone, and is not specifically limited. Among these, magnesium, titanium, iron, cobalt, nickel, copper, zinc and aluminum are preferably used as the center metal.

Specific examples of the phthalocyanine pigment in the invention include C. I. Pigment Blue 15, C. I. Pigment Blue 15:1, C. I. Pigment Blue 15:2, C. I. Pigment Blue 15:3, C. I. Pigment Blue 15:4, C. I. Pigment Blue 15:5, C. I. Pigment Blue 15:6, C. I. Pigment Blue 16, C. I. Pigment Blue 17:1, C. I. Pigment Blue 75, C. I. Pigment Blue 79, C. I. Pigment Green 7, C. I. Pigment Green 36, C. I. Pigment Green 37, chloroaluminum phthalocyanine, hydroxyaluminum phthalocyanine, aluminum phthalocyanine oxide and zinc phthalocyanine. Among these, C. I. Pigment Blue 15, C. I. Pigment Blue 15:6, C. I. Pigment Blue 15:1 and C. I. Pigment Blue 15:2 are preferable, and C. I. Pigment Blue 15:6 is specifically preferable in view of light resistance and coloring property.

The content of the phthalocyanine pigment in the colored curable composition in the invention is preferably 10 mass % to 70 mass %, more preferably 20 mass % to 60 mass %, and most preferably 35 mass % to 50 mass % with respect to all the solid components in the colored curable composition.

The content ratio of the specific complex to the phthalocyanine pigment (phthalocyanine pigment: specific complex) is preferably 100:5 to 100:100, more preferably 100:15 to 100:75, further preferably 100:25 to 100:50.

[(B) Dispersing Agent]

The colored curable composition of the invention includes the (B) dispersing agent.

As the (B) dispersing agent, known pigment dispersing agents and surfactants may be used.

As the dispersing agent, many kinds of compounds may be used, and examples thereof include phthalocyanine derivatives (commercial product, trade name: EFKA-745 (manufactured by Efka)), SOLSPERSE 5000 (trade name, manufactured by Lubrizol Japan Ltd.); cationic surfactants including organosiloxane polymers (trade name: KP341, manufactured by Shin-Etsu Chemical Co., Ltd.), (meth) acrylic acid (co)polymers (trade names: POLYFLOW Nos. 75, 90 and 95, manufactured by Kyoeisha Chemical Co., Ltd.) and W001 (trade name, manufactured by Yusho Co., Ltd.); nonionic surfactants including polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate and sorbitan fatty acid esters; anionic surfactants including W004, W005 and W017 (trade names, manufactured by Yusho Co., Ltd.); polymer dispersing agents (trade names: EFKA-46, EFKA-47, EFKA-47EA, EFKA POLYMER 100, EFKA POLYMER 400, EFKA POLYMER 401 and EFKA POLYMER 450, manufactured by Morishita & Co., Ltd., and trade names: DISPERSE AID 6, DISPERSE AID 8, DISPERSE AID 15 and DISPERSE AID 9100, manufactured by San Nopco Ltd.); various SOLSPERSE dispersing agents (trade names: SOLSPERSE 3000, 5000, 9000, 12000, 13240, 13940, 17000, 24000, 26000 and 28000, manufactured by Lubrizol Japan Ltd.); ADEKA PLURONIC L31, F38, L42, L44, L61, L64, F68, L72, P95, F77, P84, F87, P94, L101, P103, F108, L121 and P-123 (trade names, manufactured by Adeka Corporation), and ISONET S-20 (trade name, manufactured by Sanyo Chemical Industries, Ltd.).

The content of the (B) dispersing agent in the colored curable composition in the invention is preferably 1 mass % to 80 mass %, more preferably 5 mass % to 70 mass %, and most preferably 10 mass % to 60 mass % with respect to the pigment.

[(C) Polymerizable Compound]

The colored curable composition of the invention includes the (C) polymerizable compound. As the polymerizable compound, for example, an addition-polymerizable compound having at least one ethylenic unsaturated double bond may be exemplified. Specifically, it is selected from compounds having at least one, preferably two or more terminal ethylenic unsaturated bonds. Such compounds are widely known in this industrial field, and may be used in the invention without specific limitation. These may have any chemical form of, for example, a monomer, a prepolymer (i.e., a dimer, trimer or oligomer) or a mixture thereof, or a (co)polymer thereof.

In the present specification, an acryloyl group and a methacryloyl group may be collectively referred to as a (meth) acryloyl group, and an acrylate and a methacrylate may be collectively referred to as a (meth)acrylate.

Examples of the (C) polymerizable compound may include an unsaturated carboxylic acid (e.g., acrylic acid, methacrylic acid, itaconic acid, crotonic acid, isocrotonic acid, maleic acid and the like) and an ester and an amide thereof, and preferable examples may include an ester of an unsaturated carboxylic acid and an aliphatic polyvalent alcohol compound and an amide of an unsaturated carboxylic acid and an aliphatic polyvalent amine compound. Furthermore, an adduct of an unsaturated carboxylic acid ester or an amide having a nucleophilic substituent such as a hydroxyl group, an amino group or a mercapto group with a monofunctional or multifunctional isocyanate or epoxy, a dehydration condensate with a monofunctional or multifunctional carboxylic acid, and the like are preferably used. Moreover, an adduct of an unsaturated carboxylic acid ester or amide having an electrophilic substituent such as an isocyanate group or an epoxy group with a monofunctional or multifunctional alcohol, amine or thiol, and a substituted reaction product of an unsaturated carboxylic acid ester or amide having a detachable substituent such as a halogen group or a tosyloxy group with a monofunctional or multifunctional alcohol, amine or thiol are also preferable. In addition, as another example, compounds in which the unsaturated carboxylic acid is replaced with unsaturated phosphonic acid, styrene, vinyl ether or the like are also possible.

Specific examples of the monomer of the ester of the aliphatic polyvalent alcohol compound and the unsaturated carboxylic acid include acrylic acid esters including ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, tripentaerythritol polyacrylate (acrylate group number: 1-8), tetrapentaerythritol polyacrylate (acrylate group number: 1-10), pentapentaerythritol polyacrylate (acrylate group number: 1-12), sorbitol triacrylate, sorbitol tetraacrylate, sorbitol pentaacrylate, sorbitol hexaacrylate, tri(acryloyloxyethyl)isocyanurate, polyesteracrylate oligomer and isocyanuric acid EO-modified triacrylate.

Examples of the methacrylic acid ester include tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy) phenyl]dimethylmethane and bis-[p-(methacryloxyethoxy) phenyl]dimethylmethane.

Examples of the itaconic acid ester include ethylene glycol diitaconate, propylene glycol diitaconate, 1,3-butanediol diitaconate, 1,4-butanediol diitaconate, tetramethylene glycol diitaconate, pentaerythritol diitaconate and sorbitol tetraitaconate, examples of the crotonic acid ester include ethylene glycol dicrotonate, tetramethylene glycol dicrotonate, pentaerythritol dicrotonate and sorbitol tetradicrotonate, examples of the isocrotonic acid ester include ethylene glycol diisocrotonate, pentaerythritol diisocrotonate and sorbitol tetraisocrotonate, and examples of the maleic acid ester include ethylene glycol dimaleate, triethylene glycol dimaleate, pentaerythritol dimaleate and sorbitol tetramaleate and the like.

Preferable examples of other esters to be used include the aliphatic alcohol esters described in Japanese Examined Patent Publication (JP-B) No. 51-47334 and JP-A No. 57-196231, those including an aromatic backbone described in JP-A Nos. 59-5240, 59-5241 and 2-226149, and those including an amino group described in JP-A No. 1-165613. The above-mentioned ester monomers may be used as a mixture.

Specific examples of the monomer of the amide of the aliphatic polyvalent amine compound and the unsaturated carboxylic acid include methylene bis-acrylamide, methylene bis-methacrylamide, 1,6-hexamethylene bis-acrylamide, 1,6-hexamethylene bis-methacrylamide, diethylenetriamine tris-acrylamide, xylylene bis-acrylamide and xylylene bis-methacrylamide.

Examples of other preferable amide monomers may include those having a cyclohexylene structure described in JP-B No. 54-21726.

Alternatively, an urethane type addition-polymerizable compound produced by using addition reaction between an isocyanate and a hydroxy group is also preferable, and specific examples thereof include a vinyl urethane compound including two or more polymerizable vinyl groups in one molecule as described in JP-B No. 48-41708, which is obtained by adding a vinyl monomer including a hydroxy group represented by the following formula (A) to a polyisocyanate compound having two or more isocyanate groups in one molecule:

   (A)

wherein R and R' each independently represent H or $CH_3$.

Urethane acrylates such as those described in JP-A No. 51-37193, JP-B Nos. 2-32293 and 2-16765; or the urethane compounds having an ethylene oxide-based skeleton described in JP-B Nos. 58-49860, 56-17654, 62-39417 and 62-39418, are also suitable. If the addition polymerizable compounds having an amino structure or a sulfide structure in the molecule, as described in JP-A Nos. 63-277653, 63-260909 and 1-105238, are used, a colored curable composition that is very excellent in photocuring speed may be obtained.

Other examples include polyfunctional acrylates or methacrylates such as the polyester acrylates and epoxy acrylates obtained by reacting an epoxy resin and (meth)acrylic acid, such as those described in JP-A No. 48-64183, JP-B Nos. 49-43191 and 52-30490; the specific unsaturated compounds described in JP-B Nos. 46-43946, 1-40337 and 1-40336; the vinylphosphonic acid-based compounds described in JP-A No. 2-25493; and the like. Under certain circumstances, the structure containing a perfluoroalkyl group described in JP-A No. 61-22048 is also suitably used. The compounds introduced in Journal of the Adhesion Society of Japan, Vol. 20, No. 7, pp. 300-308 (1984) as photocurable monomers and oligomers, may also be used.

For these polymerizable compounds, details of the method of use including the structure, whether single use or combination use, and the amount to be added, may be arbitrarily set according to the ultimate designing of performance of the colored curable composition. For example, polymerizable compounds are selected in view of the following points.

In view of sensitivity, a structure including many unsaturated groups per one molecule is preferable, and bi- or more functional structure is preferable in many cases. Further, a tri- or more functional compound is preferable in order to enhance the strength of the colored image portion (that is, the colored curable composition layer), and a method of adjusting both sensitivity and strength by using compounds having different functional numbers and different polymerizable groups (e.g., acrylic acid esters, methacrylic acid esters, styrene compounds and vinyl ether compounds) in combination is also effective. In view of the curing sensitivity, a compound having preferably two or more, more preferably three or more, still more preferably four or more (meth)acrylic acid ester structures may be used. In view of the curing sensitivity, and the developability of the unexposed portion, an EO modified compound is preferably included. In view of the curing sensitivity and the strength of the exposed portion, a compound having a urethane bond is preferably used.

Furthermore, selection and use of the polymerizable compound are also important factors for compatibility with other components (e.g., an alkali soluble resin and an initiator) included in the colored curable composition layer. For example, compatibility may be improved by using a compound having low purity or using two or more kinds of compounds in combination. Further, a specific structure may be selected in order to improve adhesion with a substrate.

From the above viewpoints, preferable examples include bisphenol A di(meth)acrylate, bisphenol A di(meth)acrylate EO modified product, trimethylolpropane tri(meth)acrylate, trimethylolpropane tri((meth)acryloyloxypropyl)ether, trimethylolethane tri(meth)acrylate, tetraethylene glycol di(meth)acrylate, pentaerythritol di(meth)acrylate, pentaerythritol tri(meth)acrylate, pentaerythritol tetra(meth)acrylate, dipentaerythritol tetra(meth)acrylate, dipentaerythritol penta(meth)acrylate, dipentaerythritol hexa(meth)acrylate, ethoxylated bisphenol A diacrylate, sorbitol tri(meth)acrylate, sorbitol tetra(meth)acrylate, sorbitol penta(meth)acrylate, sorbitol hexa(meth)acrylate, tri((meth)acryloyloxyethyl) isocyanurate, pentaerythritol tetra(meth)acrylate EO modified product, dipentaerythritol hexa(meth)acrylate EO modified product, and the like. Preferable examples of commercially available products include urethane oligomer UAS-10, UAB-140 (trade names, manufactured by Sanyo-Kokusaku Pulp Co., Ltd.), KAYARAD DPHA (trade name, manufactured by Nippon Kayaku Co., Ltd.), NK ESTER A-TMMT, NK ESTER A-TMPT, NK ESTER A-TMM-3 (trade names, manufactured by Shin-Nakamura Chemical Co., Ltd.), ARONIX M-305, ARONIX M-306, ARONIX M-309, ARONIX M-450, ARONIX M-402 (trade names, manufactured by Toagosei Co., Ltd.), V#802 (manufactured by Osaka Organic Chemical Industry Ltd.), UA-306H, UA-306T, UA-306I, AH-600, T-600, AI-600 (trade names, manufactured by Kyoeisha Chemical Co., Ltd.).

Among them, bisphenol A di(meth)acrylate EO modified product, ethoxylated bisphenol A diacrylate, pentaerythritol tri(meth)acrylate, pentaerythritol tetra(meth)acrylate, dipentaerythritol penta(meth)acrylate, dipentaerythritol hexa(meth)acrylate, tri((meth)acryloyloxyethyl) isocyanurate, pentaerythritol tetra(meth)acrylate EO modified product, dipentaerythritol hexa(meth)acrylate EO modified product, and the like are preferable. As commercially available products, KAYARAD DPHA (trade name, manufactured by Nippon Kayaku Co., Ltd.), NK ESTER A-TMMT, NK ESTER A-TMPT, NK ESTER A-TMM-3 (trade names, manufactured by Shin-Nakamura Chemical Co., Ltd.), ARONIX M-305, ARONIX M-306, ARONIX M-309, ARONIX M-450, ARONIX M-402 (trade names, manufactured by Toagosei Co., Ltd.), and V#802 (manufactured by Osaka Organic Chemical Industry Ltd.) are more preferable.

The content of the polymerizable compound (total content in case of two or more polymerizable compounds being used) in the whole solid content in the colored curable composition is not specifically limited, and is preferably 10 mass % to 80 mass %, more preferably 15 mass % to 75 mass %, and specifically preferably 20 mass % to 60 mass % in view of more effectively obtaining the effect of the invention.

[(D) Photopolymerization Initiator]

The colored curable composition of the invention includes the (D) photopolymerization initiator.

The photopolymerization initiator is not specifically limited as long it may polymerize the (C) polymerizable compound mentioned above, and is preferably selected in view of property, initiation efficiency, absorption wavelength, availability, cost and the like.

Examples of the photopolymerization initiator include at least one active halogen compound selected from halomethyloxadiazole compounds and halomethyl-s-triazine compounds, 3-aryl-substituted coumarin compounds, lophine dimers, benzophenone compounds, acetophenone compounds and derivatives thereof, cyclopentadiene-benzene-iron complexes and salts thereof, and oxime compounds. Specific examples of the photopolymerization initiator include those described in the paragraphs [0070] to [0077] of JP-A No. 2004-295116. Among these, oxime compounds are preferable in view of rapid polymerization reaction and the like.

The oxime compound (hereinafter also referred to as "oxime photopolymerization initiator") is not specifically limited, and examples include the oxime compounds described in, for example, JP-A No. 2000-80068, WO02/100903A1, JP-A No. 2001-233842 and the like.

Specific examples include, but are not limited to,
2-(O-benzoyloxime)-1-[4-(phenylthio)phenyl]-1,2-butanedione,
2-(O-benzoyloxime)-1-[4-(phenylthio)phenyl]-1,2-pentanedione,
2-(O-benzoyloxime)-1-[4-(phenylthio)phenyl]-1,2-hexanedione,
2-(O-benzoyloxime)-1-[4-(phenylthio)phenyl]-1,2-heptanedione,
2-(O-benzoyloxime)-1-[4-(phenylthio)phenyl]-1,2-octanedione,
2-(O-benzoyloxime)-1-[4-(methylphenylthio)phenyl]-1,2-butanedione,
2-(O-benzoyloxime)-1-[4-(ethylphenylthio)phenyl]-1,2-butanedione,
2-(O-benzoyloxime)-1-[4-(butylphenylthio)phenyl]-1,2-butanedione,
1-(O-acetyloxime)-1-[9-ethyl-6-(2-methylbenzoyl)-9H-carbazole-3-yl]ethanone,
1-(O-acetyloxime)-1-[9-methyl-6-(2-methylbenzoyl)-9H-carbazole-3-yl]ethanone,
1-(O-acetyloxime)-1-[9-propyl-6-(2-methylbenzoyl)-9H-carbazole-3-yl]ethanone,
1-(O-acetyloxime)-1-[9-ethyl-6-(2-ethylbenzoyl)-9H-carbazole-3-yl]ethanone and
1-(O-acetyloxime)-1-[9-ethyl-6-(2-butylbenzoyl)-9H-carbazole-3-yl]ethanone.

Among these, oxime-O-acyl compounds including 2-(O-benzoyloxime)-1-[4-(phenylthio)phenyl]-1,2-octanedione and 1-(O-acetyloxime)-1-[9-ethyl-6-(2-methylbenzoyl)-9H-carbazole-3-yl]ethanone are specifically preferable in view of that a pattern having a good shape (specifically, a rectangle shape of a pattern in case of a solid-state image pickup device) may be obtained with smaller amount of exposure, and specific examples include CGI-124 and CGI-242 (trade names, manufactured by Ciba Specialty Chemicals).

In the invention, the compound represented by the following formula (1) is preferable as the oxime compound in view of sensitivity, stability over time and coloring during post-heating.

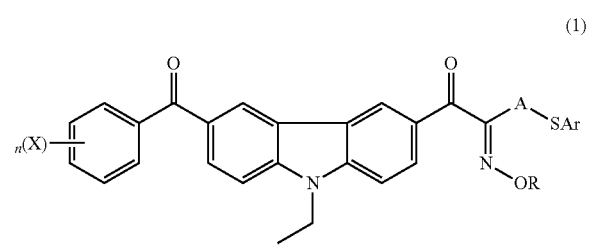

(1)

In the formula (1), R and X each independently represent a monovalent substituent, A is a bivalent organic group, Ar is an aryl group, and n is an integer of 1 to 5.

As R, an acyl group is preferable in view of improvement of sensitivity, and preferable specific examples include an acetyl group, a propionyl group, a benzoyl group and a toluoyl group.

A is preferably an unsubstituted alkylene group, an alkylene group substituted by an alkyl group (e.g., a methyl group, an ethyl group, a tert-butyl group and a dodecyl group), an alkylene group substituted by an alkenyl group (e.g., a vinyl group and an allyl group), or an alkylene group substituted by an aryl group (e.g., a phenyl group, a p-tolyl group, a xylyl group, a cumenyl group, a naphthyl group, an anthryl group, a phenanthryl group and a styryl group), in view of improved sensitivity and suppression of coloring by heating or storing over time.

Ar is preferably a substituted or unsubstituted phenyl group in view of improved sensitivity and suppression of coloring by heating or storing over time. In case of the substituted phenyl group, preferable examples of the substituent include halogen groups including a fluorine atom, a chlorine atom, a bromine atom and an iodine atom.

X is preferably an optionally substituted alkyl group, an optionally substituted aryl group, an optionally substituted alkenyl group, an optionally substituted alkynyl group, an optionally substituted alkoxy group, an optionally substituted aryloxy group, an optionally substituted alkylthioxy group, an optionally substituted arylthioxy group or an optionally substituted amino group, in view of improvement of solubility in solvents and absorption efficiency in a long wavelength region.

In the formula (1), n is preferably an integer of 1 or 2.

Hereinafter the specific examples of the compound represented by the formula (1) are shown, but the invention is not limited to these examples.

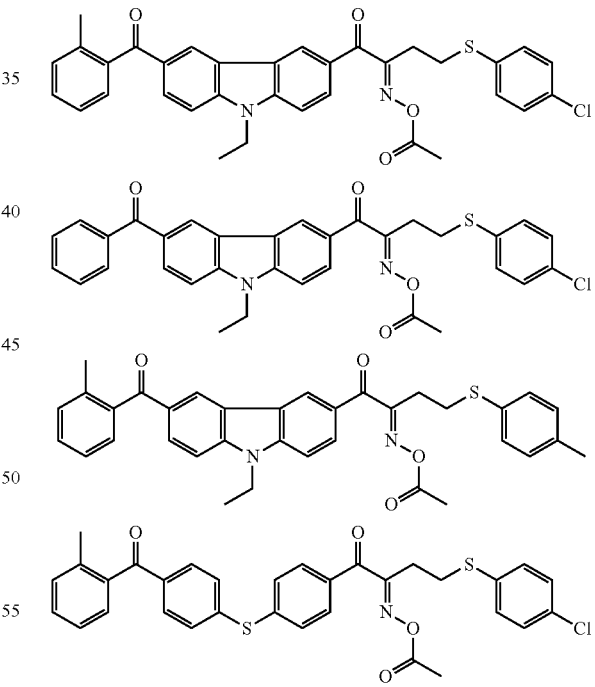

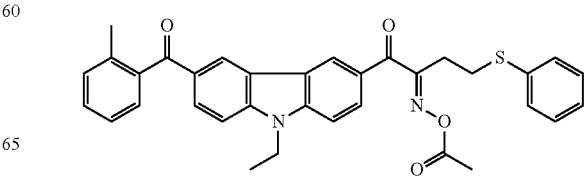

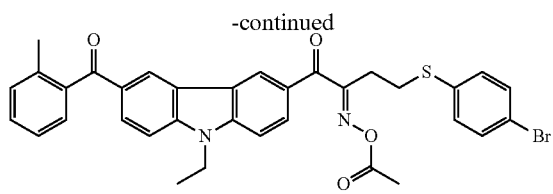

Besides the above-mentioned photopolymerization initiators, other known photopolymerization initiators described in the paragraph [0079] of JP-A No. 2004-295116 may be used for the colored curable composition of the invention.

Only one photopolymerization initiator may be incorporated, or two or more kinds thereof may be incorporated in combination. The content of the photopolymerization initiator (total content in case of two or more photopolymerization initiators being used) in the whole solid components of the colored curable composition is preferably 3 mass % to 20 mass %, more preferably 4 mass % to 19 mass %, and specifically preferably 5 mass % to 18 mass %, in view of obtaining the effect of the invention more effectively.

—Sensitizing Dye—

In the colored curable composition of the present invention, a sensitizing dye may be added as required. The sensitizing dye may promote the radical generating reaction of the photopolymerization initiator by light-exposure of the wavelengths absorbable by the sensitizing dye, and thereby may promote the polymerization reaction of the polymerizable compound.

Examples of such a sensitizing dye include known spectral sensitizing dyes or colorants, or dyes or colorants that absorb light and interact with the photopolymerization initiator.

(Spectral Sensitizing Dye or Colorant)

Examples of preferable spectral sensitizing dyes or colorants used as the sensitizing dye in the present invention include: polynuclear aromatic compounds (for example, pyrene, perylene, triphenylene); xanthenes (for example, fluorescein, eosin, erythrosin, rhodamine B, rose bengal; cyanines (for example, thiacarbocyanine, oxacarbocyanine); merocyanines (for example, merocyanine, carbomerocyanine); thiazines (for example, thionine, methylene blue and toluidine blue); acridines (for example, acridine orange, chloroflavin, acriflavine); phthalocyanines (for example, phthalocyanine, metal phthalocyanines); porphyrins (for example, tetraphenylporphyrin, central metal-substituted porphyrins); chlorophylls (for example, chlorophyll, chlorophyllin, central metal-substituted chlorophyll); metal complexes; anthraquinones (for example, anthraquinone); squaryliums (for example, squarylium); and the like.

More preferable examples of the spectral sensitizing dyes include styryl-based dyes described in JP-B No. 37-13034, cation dyes described in JP-A No. 62-143044, quinoxalinium salts described in JP-B No. 59-24147, novel methylene blue compounds described in JP-A No. 64-33104, anthraquinones described in JP-A No. 64-56767, benzoxanthene dyes described in JP-A No. 2-1714, acridines described in JP-A No. 2-226148 and JP-A No. 2-226149, pyrylium salts described in JP-B No. 40-28499, cyanines described in JP-B No. 46-42363, benzofuran dyes described in JP-A No. 2-63053, conjugate ketone dyes described in JP-A No. 2-85858 and JP-A No. 2-216154, dyes described in JP-A No. 57-10605, azocinnamylidene derivatives described in JP-B No. 2-30321, cyanine-based dyes described in JP-A No. 1-287105, xanthene-based dyes described in JP-A No. 62-31844, JP-A No. 62-31848, and JP-A No. 62-143043, aminostyryl ketones described in JP-B No. 59-28325, dyes described in JP-A No. 2-179643, merocyanine dyes described in JP-A No. 2-244050, melocyanine dyes described in JP-B No. 59-28326, merocyanine dyes described in JP-A No. 59-89303, merocyanine dyes described in JP-A No. 8-129257, and benzopyran-based dyes described in JP-A No. 8-334897.

(Dyes Having Maximum Absorption Wavelength at 350 Nm to 450 Nm)

Examples of other preferable embodiments of sensitizing dyes include compounds belonging to the following groups of dyes having a maximum absorption wavelength at 350 nm to 450 nm. Examples include: polynuclear aromatic compounds (for example, pyrene, perylene and triphenylene); xanthenes (for example, fluorescein, eosin, erythrosine, rhodamine B, and rose bengal); cyanines (for example, thiacarbocyanine and oxacarbocyanine); merocyanines (for example, merocyanine and carbomerocyanine); thiazines (for example, thionine, methylene blue and toluidine blue); acridines (for example, acridine orange, chloroflavin, acriflavine); anthraquinones (for example, anthraquinone); and squaryliums (for example, squarylium).

With respect to the sensitizing dyes, the following various chemical modifications may be performed thereto in order to improve the characteristics of the colored curable composition of the present invention. For example, by combining the sensitizing dye with an addition polymerizable compound structure (for example, an acryloyl group or a methacryloyl group) using methods such as a covalent bond, an ionic bond, or a hydrogen bond, an improvement in the strength of the cross-linked cured layer and an improvement in the effect of suppressing unwanted precipitation of the dye from the cross-linked cured layer may be obtained.

The content of the sensitizing dye is preferably 0.01 mass % to 20 mass %, more preferably 0.01 mass % to 10 mass %, and still more preferably 0.1 mass % to 5 mass %, with respect to the total solid content of the colored curable composition. When the content of the sensitizing dye is within these ranges, high sensitivity to the exposure wavelengths of an ultrahigh pressure mercury lamp, and curability of the deeper layer portions may be obtained, and these ranges are also preferable in terms of developing margin and pattern formability.

—Hydrogen Donating Compound—

The colored curable composition of the invention preferably contains a hydrogen donating compound. In the invention, the hydrogen donating compound further improves the sensitivity of the sensitizing dye and photopolymerization initiator to active radiation, or prevents inhibition of polymerization of the polymerizable compound caused by oxygen.

Examples of the hydrogen donating compound include amines such as the compounds described in M. R. Sander et al, "Journal of Polymer Society", vol. 10, p. 3173 (1972), JP-B No. 44-20189, JP-A Nos. 51-82102, 52-134692, 59-138205, 60-84305, 62-18537, 64-33104, and Research Disclosure No. 33825. Specific examples include triethanolamine, ethyl p-dimethylaminobenzoate, p-formyldimethylaniline, and p-methylthiodimethylaniline.

Other examples of the hydrogen donating compound include thiols and sulfides such as thiol compounds described in JP-A No. 53-702, JP-B No. 55-500806, and JP-A No. 5-142772, and disulfide compounds described in JP-A No. 56-75643, and specific examples thereof include 2-mercaptobenzothiazole, 2-mercaptobenzoxazole, 2-mercaptobenzimidazole, 2-mercapto-4(3H)-quinazoline, and β-mercaptonaphthalene.

Yet other examples of the hydrogen donating compound include amino acid compounds such as N-phenylglycine, organometallic compounds described in JP-B No. 48-42965, such as tributyl tin acetate, hydrogen donors described in JP-B No. 55-34414, and sulfur compounds described in JP-A No. 6-308727, such as trithiane.

The content of the hydrogen donating compound is preferably from 0.1 to 30% by mass, more preferably from 0.5 to 25% by mass, and even more preferably from 1 to 20% by mass with respect to the total solid content of the colored curable composition, from the viewpoint of improving the curing rate based on the balance of the polymerization growth rate and chain transfer.

[(E) Organic Solvent]

The colored curable composition of the invention includes the (E) organic solvent.

The organic solvent is not specifically limited so long as it may satisfy the solubility of the components existing together and the coating property of the colored curable composition, and is preferably selected in view of solubility of the binder, coating property and safety.

Examples of the organic solvent include esters including ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate and ethyl lactate, oxyacetate alkyl esters (e.g., methyl oxyacetate, ethyl oxyacetate and butyl oxyacetate (specifically, methyl methoxyacetate, ethyl methoxyacetate, butyl methoxyacetate, methyl ethoxyacetate and ethyl ethoxyacetate)), 3-oxypropionate alkyl esters (e.g., methyl 3-oxypropionate and ethyl 3-oxypropionate (specifically, methyl 3-methoxypropionate, ethyl 3-methoxypropionate, methyl 3-ethoxypropionate and ethyl 3-ethoxypropionate)), and 2-oxypropionate alkyl esters (e.g., methyl 2-oxypropionate, ethyl 2-oxypropionate and propyl 2-oxypropionate (specifically, methyl 2-methoxypropionate, ethyl 2-methoxypropionate, propyl 2-methoxypropionate, methyl 2-ethoxypropionate and ethyl 2-ethoxypropionate)), methyl 2-oxy-2-methylpropionate and ethyl 2-oxy-2-methylpropionate (specifically, methyl 2-methoxy-2-methylpropionate and ethyl 2-ethoxy-2-methylpropionate)), methyl pyruvate, ethyl pyruvate, propyl pyruvate, methyl acetacetate, ethyl acetacetate, methyl 2-oxobutanate, and ethyl 2-oxobutanate.

Examples of the ethers include diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate and propylene glycol monopropyl ether acetate.

Examples of the ketones include methyl ethyl ketone, cyclohexanone, 2-heptanone and 3-heptanone.

Preferable examples of the aromatic hydrocarbons include toluene and xylene.

It is also preferable to mix two or more kinds of these organic solvents in view of the solubility of the above-mentioned components, and where an alkali soluble binder is included, the solubility of the binder, improvement of the state of the surface to be coated, and the like. In this case, a mixed solution of two or more kinds selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether and propylene glycol methyl ether acetate, is specifically preferable.

The content of the organic solvent in the colored curable composition is an amount at which the concentration of the whole solid components in the composition becomes preferably 10 mass % to 80 mass %, more preferably 15 mass % to 60 mass %.

[(F) Other Components]

The colored curable composition of the invention may further include other components including an alkali-soluble binder and a crosslinking agent besides the above-mentioned components to the extent that the effect of the invention is not deteriorated.

—Alkali-Soluble Binder—

The alkali-soluble binder is not specifically limited so long as it has alkali solubility, and may be preferably selected in view of heat resistance, developing property, availability and the like.

Preferable examples of the alkali-soluble binder include a linear organic high molecular polymer that may be dissolved in an organic solvent and may be developed by a weak alkali aqueous solution. Examples of such linear organic high molecular polymer include polymers having carboxylic acids at side chains including methacrylic acid copolymers, acrylic acid copolymers, itaconic acid copolymers, crotonic acid copolymers, maleic acid copolymers and partially-esterified maleic acid copolymers as described in JP-A No. 59-44615, JP-B Nos. 54-34327, 58-12577 and 54-25957 and JP-A Nos. 59-53836 and 59-71048. Acidic cellulose derivatives having carboxylic acids at side chains are also useful.

Besides the above-mentioned binders, adducts of polymers having hydroxy groups with acid anhydrides, polyhydroxystyrene resins, polysiloxane resins, poly(2-hydroxyethyl (meth)acrylate), polyvinyl pyrrolidone, polyethylene oxides, polyvinyl alcohols, and the like are also useful as the alkali-soluble binder in the invention. The linear organic high molecular polymer may be a copolymer with a hydrophilic monomer. Examples thereof include alkoxyalkyl(meth)acrylates, hydroxyalkyl(meth)acrylates, glycerol(meth)acrylates, (meth)acrylamides, N-methylolacrylamides, secondary or tertiary alkylacrylamides, dialkylaminoalkyl(meth)acrylates, morpholine(meth)acrylates, N-vinylpyrrolidone, N-vinylcaprolactam, vinylimidazole, vinyltriazole, methyl(meth)acrylates, ethyl(meth)acrylates, branched or straight chain propyl (meth)acrylates, branched or straight chain butyl(meth)acrylates, and phenoxyhydroxy propyl(meth)acrylates. Other examples of useful hydrophilic monomer include monomers including a tetrahydrofurfuryl group, a phosphoric acid group, a phosphoric acid ester group, a quaternary ammonium salt group, an ethyleneoxy chain, a propyleneoxy chain, a sulfonic acid group or a group derived from a salt thereof, or a morpholinoethyl group.

The alkali-soluble binder may have polymerizable groups at side chains in order to improve crosslinking efficiency. For example, polymers having allyl groups, (meth)acryl groups, allyloxyalkyl groups or the like at side chains, and the like are also useful. Examples of the polymer having the polymerizable groups include commercial products including KS RESIST-106 (trade name, manufactured by Osaka Organic Chemical Industry Ltd.) and CYCLOMER-P series (trade names, manufactured by Daicel Chemical Industries, Ltd.). Furthermore, in order to improve strength of cured films, alcohol soluble nylons and a polyether of 2,2-bis-(4-hydroxyphenyl)propane and epichlorohydrin are also useful.

Among these various alkali-soluble binders, polyhydroxystyrene resins, polysiloxane resins, acrylic resins, acrylamide resins and acryl/acrylamide copolymer resins are preferable in view of heat resistance, and acrylic resins, acrylamide resins and acryl/acrylamide copolymer resins are preferable in view of control of developing property.

As the acrylic resin, copolymers formed by monomers selected from benzyl(meth)acrylate, (meth)acrylic acid, hydroxyethyl(meth)acrylate, (meth)acrylamide and the like, and commercial products including KS RESIST-106 (trade name, manufactured by Osaka Organic Chemical Industry Ltd.) and CYCLOMER-P series (trade names, manufactured by Daicel Chemical Industries, Ltd.), and the like are preferable.

The alkali-soluble binder is a polymer having a weight average molecular weight (polystyrene-converted value measured by GPC) of preferably 1000 to $2\times10^5$, more preferably 2000 to $1\times10^5$, and specifically preferably 5000 to $5\times10^4$, in view of developing property, liquid viscosity and the like.

—Crosslinking Agent—

By using a crosslinking agent as a supplement in the colored curable composition of the invention, the hardness of the colored cured film formed by curing the colored curable composition may further be improved.

The crosslinking agent is not specifically limited so long as it may cure a film by crosslinking reaction, and examples include (a) an epoxy resin, (b) a melamine compound, a guanamine compound, a glycoluril compound or an urea compound substituted by at least one substituent selected from a methylol group, an alkoxymethyl group and an acyloxymethyl group, and (c) a phenol compound, a naphthol compound or a hydroxyanthracene compound substituted by at least one substituent selected from a methylol group, an alkoxymethyl group and an acyloxymethyl group. Among these, multifunctional epoxy resins are preferable.

With respect to the details of the specific example and the like of the crosslinking agent, the description on the paragraphs [0134] to [0147] of JP-A No. 2004-295116 may be referred.

—Other Additives—

When needed, various additives including fillers, polymer compounds other than those mentioned above, surfactants, adhesion accelerating agents, antioxidants, ultraviolet absorbers, aggregation preventing agents and development accelerators may be incorporated into the colored curable composition. As these additives, those described in the paragraphs [0155] to [0156] of JP-A No. 2004-295116 may be exemplified.

(Surfactant)

The colored curable composition of the invention may contain various surfactants from the viewpoint of improving the coatability. Examples of the surfactants which may be used in the invention include various surfactants such as a fluorine-containing surfactant, a nonionic surfactant, a cationic surfactant, an anionic surfactant, and a silicone-based surfactant.

In particular, when the colored curable composition of the invention contains a fluorine-containing surfactant, the liquid properties (in particular, fluidity) of the composition prepared as a coating liquid is improved, thereby enabling improvement in the uniformity of the coating thickness and the liquid saving.

That is, when a colored curable composition containing a fluorine-containing surfactant is used as a coating liquid to form a film, due to decrease in the surface tension between the surface to be coated and the coating liquid, the wettability on the surface to be coated is improved, so that the coatability on the surface to be coated is improved. As a result, even when a thin film of several micrometers is formed with a small amount of the liquid, a film with uniform thickness may be suitably formed.

The fluorine content in the fluorine-containing surfactant is preferably 3% by mass to 40% by mass, more preferably 5% by mass to 30% by mass, and particularly preferably 7% by mass to 25% by mass. A fluorine-containing surfactant having a fluorine content in this range is effective in the uniformity of the coating film thickness and the liquid saving, and has good solubility in the colored curable composition.

Examples of the fluorine-containing surfactant include MEGAFAC F171, F172, F173, F176, F177, F141, F142, F143, F144, R30, F437, F479, F482, F780 and F781 (manufactured by DIC Corporation), FLUORAD FC430, FC431 and FC171 (manufactured by Sumitomo 3M Limited), SURFLON S-382, SC-101, SC-103, SC-104, SC-105, SC1068, SC-381, SC-383, 5393 and KH-40 (manufactured by Asahi Glass Co., Ltd.), and SOLSPERSE 20000 (manufactured by Lubrizol Japan Ltd.).

Examples of the nonionic surfactant include polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, and sorbitan fatty acid ester (such as PLURONIC L10, L31, L61, L62, 10R5, 1782 and 25R2, and TETRONIC 304, 701, 704, 901, 904 and 150R1, manufactured by BASF).

Examples of the cationic surfactant include a phthalocyanine derivative (trade name: EFKA-745, manufactured by Morishita & Co., Ltd.), an organosiloxane polymer (trade name: KP341, manufactured by Shin-Etsu Chemical Co., Ltd.), a (meth)acrylic acid based (co)polymer (trade names: POLYFLOW No. 75, No. 90, No. 95, manufactured by Kyoeisha Chemical Co., Ltd.), and W001 (trade name, manufactured by Yusho Co., Ltd.).

Examples of the anionic surfactant include W004, W005 and W017 (trade names, manufactured by Yusho Co., Ltd.).

Examples of the silicone-based surfactant include "TORAY SILICONE DC3PA", "TORAY SILICONE SH7PA", "TORAY SILICONE DC11PA", "TORAY SILICONE SH21PA", "TORAY SILICONE SH28PA", "TORAY SILICONE SH29PA", "TORAY SILICONE SH30PA" and "TORAY SILICONE SH8400" (trade names, manufactured by Dow Corning Toray Co., Ltd.), "TSF-4440", "TSF-4300", "TSF-4445", "TSF-444(4)(5)(6)(7)6", "TSF-44 60" and "TSF-4452" (trade names, manufactured by Momentive Performance Materials Inc.), "KP341" (trade name, manufactured by Shin-Etsu Chemical Co., Ltd.), and "BYK323" and "BYK330" (trade names, manufactured by BYK Chemie).

Only one surfactant may be used, or two or more surfactants may be used in combination.

(Heat Polymerization Inhibitor)

Further, the colored curable composition of the invention may include the sensitizer and light stabilizer described in the paragraph [0078] of JP-A No. 2004-295116 and the heat polymerization inhibitor described in the paragraph [0081] of the same publication.

That is, in the colored curable composition of the invention, it is preferred that a small amount of a heat polymerization inhibitor be added in order to prevent unnecessary heat polymerization of the polymerizable compound during manufacture or storage of the colored curable composition.

Examples of the heat polymerization inhibitor useful in the invention include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butyl phenol), and N-nitrosophenylhydroxyamine primary cerium salt.

The addition amount of the heat polymerization inhibitor is preferably from about 0.01% to about 5% by mass with respect to the mass of the colored curable composition.

(Development Accelerator)

Furthermore, when acceleration of the alkali solubility of non-exposed areas and further improvement of the developing property of the colored curable composition are intended, an organic carboxylic acid having a molecular weight of 1000 or less, or a glycerol propoxylate having a molecular weight of from 300 to 5000, such as a glycerol propoxylate (Mw 1500), a glycerol propoxylate (Mw 1000), a glycerol propoxylate (Mw 750) or a glycerol propoxylate (Mw 4100), may be added to the composition.

Specific examples of the organic carboxylic acid having a molecular weight of 1000 or less include aliphatic monocarboxylic acids including formic acid, acetic acid, propionic acid, butyric acid, valeric acid, pivalic acid, caproic acid, diethyl acetate, enanthic acid and capric acid; aliphatic dicarboxylic acids including oxalic acid, malonic acid, succinic acid, glutaric acid, adipic acid, pimeric acid, suberic acid, azelaic acid, sebacic acid, brassylic acid, methyl malonic acid, ethyl malonic acid, dimethyl malonic acid, methyl succinic acid, tetramethyl succinic acid and citraconic acid; aliphatic tricarboxylic acids including tricarbaryl acid, aconitic acid and camphoronic acid; aromatic monocarboxylic acids including benzoic acid, toluic acid, cuminic acid, hemellitic acid and mesitylenic acid; aromatic polycarboxylic acids including phthalic acid, isophthalic acid, terephthalic acid, trimellitic acid, trimesic acid, mellophanic acid and pyromellitic acid; and other carboxylic acids including phenyl acetic acid, hydroatropic acid, hydrocinnamic acid, mandelic acid, phenylsuccinic acid, atropic acid, cinnamic acid, methyl cinnamate, benzyl cinnamate, cinnamylidene acetic acid, coumaric acid and umbellic acid.

[Preparation Method of Colored Curable Composition]

The colored curable composition of the invention is prepared by mixing the above-mentioned essential components, and optional components when needed.

During the preparation of the colored curable composition, the components for the colored curable composition may be mixed at one time, or the components may be each dissolved or dispersed in a solvent and mixed successively. The order of addition during mixing and operation condition are not specifically limited. For example, the composition may be prepared by simultaneously dissolving or dispersing all components in a solvent, or when needed, the components may be suitably prepared into two or more solutions or dispersion liquids that are mixed before use (at the time of coating) to prepare a composition.

The colored curable composition prepared as above may be filtered using a filter or the like having a pore diameter of preferably about 0.01 μm to 3.0 μm, more preferably about 0.05 μm to 0.5 μm, and subjected to use.

Since the colored curable composition of the invention has excellent storage stability, and may form colored cured films having excellent light resistance, it may be used for forming colored pixels for color filters used for liquid crystal display devices (LCD) and solid-state image pickup devices (e.g., CCD, CMOS and the like), and for use in preparation of print ink, inkjet ink, paint and the like. Specifically, it may be used for forming colored pixels for solid-state image pickup devices including CCD and CMOS.

<<Color Filter and Production Method Therefor>>

Next, a method for producing a color filter using the colored curable composition of the invention (method for producing the color filter of the invention) is explained.

The method for producing the color filter of the invention includes (A) a step of applying the colored curable composition of the invention onto a support to form a colored curable composition layer, and (B) a step of exposing the colored curable composition layer formed in the step (A) via a mask, and developing the layer to form a colored pattern.

It is preferable that the method for producing the color filter of the invention further includes (C) a step of irradiating the colored pattern formed in the step (B) with ultraviolet radiation, and (D) a step of heat-treating the colored pattern on which ultraviolet radiation has been irradiated in the step (C).

Hereinafter the method for producing the color filter of the invention is explained more specifically.

—Step (A)—

In the method for producing the color filter of the invention, the colored curable composition of the invention as mentioned above is first applied onto a support by a coating process such as spin coating, casting coating, roll coating or the like to form a colored curable composition layer, and when needed, subjected to preliminary curing (pre-baking) to dry the colored curable composition layer.

Examples of the support used for the production method of the color filter of the invention include soda glass, alkali-free glass, borosilicate glass (PYREX® glass) and quartz glass used for liquid crystal display devices and the like, and those glass materials on which a transparent electroconductive film has been adhered, opto-electronic conversion device substrates used for solid-state image pickup devices including silicon substrates, and complementary metal oxide film semiconductor (CMOS) substrates. Black stripes for separating pixels may be formed on these substrates. When needed, a primer layer may be formed on these substrates in order to improve adhesion to the upper layer, prevent diffusion of the materials, or planalize the surface.

A coating film of the colored curable composition may be formed by applying the colored curable composition of the invention directly or via another layer onto a substrate by a coating process such as spin coating, slit coating, casting coating, roll coating, bar coating, inkjet coating or the like.

When the colored curable composition is spin-coated on the support, the colored curable composition may conform well to the support by adding dropwise a suitable organic solvent and rotating prior to dropwise addition of the colored curable composition so as to decrease the amount of the liquid to be added dropwise.

The conditions for the pre-baking may include a condition in which heating is performed using a hot plate or an oven at 70° C. to 130° C. for about 0.5 minute to 15 minutes.

The thickness of the colored curable composition layer formed by the colored curable composition is suitably selected according to the purpose. Generally, in a color filter for a solid-state image pickup device or the like, it is preferably 0.2 μm to 5.0 μm, more preferably 0.3 μm to 2.5 μm, and most preferably 0.3 μm to 1.5 μm. In a color filter for a liquid crystal display device or the like, it is preferably 0.2 μm to 5.0 μm, more preferably 1.0 μm to 4.0 μm, and most preferably 1.5 μm to 3.5 μm. The thickness of the colored curable composition layer as used herein is a film thickness after pre-baking.

—Step (B)—

Next, in the production method of the color filter of the invention, the colored curable composition layer formed on the support is exposed via a mask.

The light or radiation that may be applied to this exposing is preferably g-ray, h-ray, i-ray, KrF ray or ArF ray, specifically preferably i-ray. When i-ray is used as irradiation light, it is preferable to irradiate by an exposure amount of 100 mJ/cm$^2$ to 10000 mJ/cm$^2$.

Examples of other usable exposure radiation source include an ultrahigh pressure, high pressure, medium pressure or low pressure mercury lamp, a chemical lamp, a carbon-arc lamp, a xenon lamp, a metal halide lamp, visible and ultraviolet laser sources, a fluorescent lamp, a tungsten lamp, and sunlight.

(Exposure Step Using Laser Source)

In the exposure step using a laser source in the invention, an ultraviolet laser may be used as a light source. Laser is an acronym of Light Amplification by Stimulated Emission of Radiation. The oscillator and amplifier of the laser utilize the phenomenon of induced emission that occurs in a substance with population inversion, and generate monochromatic light having higher coherency and directionality by amplification and oscillation of light wave. Examples of the excitation medium of the laser include crystal, glass, liquid, dye and gas, and a known laser having an oscillation wavelength in the ultraviolet region, such as a solid laser, a liquid laser, a gas laser, or a semiconductor laser, may be used. Among them, a solid laser and a gas laser are preferable from the viewpoint of laser output and oscillation wavelength.

With respect to the wavelength of the laser, an ultraviolet laser having a wavelength of preferably from 300 nm to 380 nm and more preferably from 300 nm to 360 nm is preferable, because such a wavelength corresponds to the photosensitive wavelength of the resist.

Specifically, an Nd:YAG laser (third harmonic: 355 nm), which is a relatively cheap solid laser with particulary high out put, and an eximer laser (XeCl: 308 nm, XeF: 353 nm) may be preferably used.

The exposure amount of a body to be exposed (a pattern) is preferably form 1 mJ/cm$^2$ to 100 mJ/cm$^2$, and more preferably form 1 mJ/cm$^2$ to 50 mJ/cm$^2$. This range of the exposure amount is preferable in terms of the productibity of the formed pattern.

The exposing apparatus which may be used in the invention is not particularly limited, and examples thereof include commercially available apparatuses such as Callisto (trade name, manufactured by V Technology Co., Ltd.), EGIS (trade name, manufactured by V Technology Co., Ltd.) and DF2200G (trade name, manufactured by Dainippon Screen Mfg. Co., Ltd.), and other apparatuses may also be preferably used.

A light-emitting diode (LED) and a laser diode (LD) may be used as an active radiation source. Specifically, when an ultraviolet radiation source is necessary, an ultraviolet LED and an ultraviolet LD may be used. For example, Nichia Corporation places an ultraviolet LED having a main emission spectrum in a wavelength range of between 365 nm and 420 nm on the market. When a further shorter wavelength is necessary, an LED disclosed in U.S. Pat. No. 6,084,250 may be used which may emit active radiation centered at between 300 nm and 370 nm. Another ultraviolet LED may also available which may irradiate radiation of a different ultraviolet range. The active radiation source in the present invention is preferably a UV-LED and particularly preferably a UV-LED having a peak wavelength of from 340 nm to 370 nm.

An ultraviolet laser has good linearity, and thus may perform pattern exposure without a mask. However, a mask is preferably used during pattern exposure because the linearity of the pattern is further improved.

The exposed colored curable composition layer may be heated using a hot plate or an oven at 70° C. to 180° C. for about 0.5 minutes to 15 minutes prior to the subsequent developing treatment.

Furthermore, exposing may be performed while nitrogen gas is flowing in a chamber so as to suppress oxidation discoloration of the coloring material in the colored curable composition layer.

Subsequently, the exposed colored curable composition layer is developed using a developer. In this way, a negative-type or positive-type colored pattern (resist pattern) may be formed.

A combination of various organic solvents or an alkaline aqueous solutions may be used as a developer so long as it dissolves uncured parts (unexposed parts) and does not dissolve cured parts (exposed parts) in the colored curable composition layer. When the developer is an alkaline aqueous solution, it is preferable to adjust the alkali concentration to preferably pH 11 to 13, more preferably pH 11.5 to 12.5.

Examples of the alkaline aqueous solution include an alkaline aqueous solution of sodium hydroxide, potassium hydroxide, sodium carbonate, sodium hydrogen carbonate, sodium silicate, sodium metasilicate, ammonia, ethylamine, diethylamine, dimethylethanolamine, tetramethylammonium hydroxide, tetraethylammonium hydroxide, choline, pyrrole, piperidine, or 1,8-diazabicyclo[5.4.0]-7-undecene.

Specifically, an alkaline aqueous solution in which the concentration of tetraethylammonium hydroxide has been adjusted to 0.001 mass % to 10 mass %, preferably 0.01 mass % to 5 mass % may be used as a developer.

The developing time is preferably 30 seconds to 300 seconds, more preferably 30 seconds to 120 seconds. The developing temperature is preferably 20° C. to 40° C., more preferably 23° C.

Developing may be performed by using a paddle system, a shower system, a spray system or the like.

It is preferable that washing is performed by using water after developing using an alkali aqueous solution. A washing system is also suitably selected according to the purpose, and rinse treatment may be performed by rotating a support such as a silicon wafer at a revolution of 10 rpm to 500 rpm and supplying pure water in shower state from a spray nozzle from the above of the revolution center.

Thereafter, in the production method of the color filter of the invention, the colored pattern formed by developing may be subjected to post-heating and/or post-exposure to accelerate curing of the colored pattern when needed.

—Step (C)—

Specifically, in the production method of the color filter of the invention, the colored pattern (pixel) formed by the colored curable composition of the invention may be subjected to post-exposure by irradiation of ultraviolet radiation, whereby color transfer to the adjacent pixels and to the laminated upper and lower layers may be effectively suppressed. The color transfer is an inherent problem that occurs when a dye such as the specific complex is used as a coloring material as in the colored curable composition of the invention. The color transfer may be decreased by post-exposure by ultraviolet radiation irradiation as mentioned below.

(Post-Exposure by Ultraviolet Radiation Irradiation)

In post-exposure by ultraviolet radiation irradiation, it is preferable that a colored pattern that has been subjected to a developing treatment as mentioned above is irradiated with ultraviolet light (UV light) having an irradiation light amount [mJ/cm$^2$] of 10 or more times as large as an exposure amount [mJ/cm$^2$] in the exposing treatment prior to the development.

By irradiating the developed colored pattern with ultraviolet light (UV light) for a predetermined time period at between the developing treatment and the heat treatment by the step (D) mentioned below, color transfer during the subsequent heating may be effectively prevented, and light resistance is improved.

As a light source for irradiating ultraviolet light, for example, an ultra high pressure mercury lamp, a high pressure mercury lamp, a low pressure mercury lamp, a DEEP UV lamp or the like may be used. Among these, a light source that irradiates ultraviolet light including light at a wavelength of 275 nm or less, and may irradiate light in which an irradiation illuminance [mW/cm$^2$] of the light at a wavelength of 275 nm or less is 5% or more with respect to the integral irradiation illuminance of the light at whole wavelengths in the ultraviolet light is preferable. By adjusting the irradiation illuminance of the light at a wavelength of 275 nm or less in the ultraviolet light to 5% or more, effect of suppressing color transfer to the adjacent pixels and the upper and lower layer and effect of improving light resistance may be further improved.

From these viewpoints, it is preferable that the post-exposure by ultraviolet radiation irradiation is performed by using a light source that differs from the light source (such as i-ray) used in the exposing in the step (B), specifically a high pressure mercury lamp, a low pressure mercury lamp or the like. Among these, for the same reason as mentioned above, the irradiation illuminance [mW/cm$^2$] of the light at a wavelength of 275 nm or less is preferably 7% or more with respect to the integral irradiation illuminance of the light at whole wavelengths in the ultraviolet light. Furthermore, it is desirable that the upper limit of the irradiation illuminance of the light at a wavelength of 275 nm or less is 25% or less.

The integral irradiation illuminance refers to a sum (area) of illuminances of lights of wavelengths included in irradiated light when a curve is drawn by taking an illuminance for every spectral wavelength (radiation energy for passing through a unit area in a unit time period; [mW/m$^2$]) as a vertical axis and the wavelength [nm] of the light as a horizontal axis.

It is preferable that ultraviolet light is irradiated by an irradiation light amount [mJ/cm$^2$] of 10 or more times as large as the exposure amount during the exposure in the step (B). When the irradiated light amount in the step (C) is less than 10 times as large as the exposure amount during the exposure in the step (B), color transfer to adjacent pixels and to upper and lower layers may not be prevented, and light resistance may be deteriorated.

Among these, the irradiation light amount of ultraviolet light is preferably 12 or more times and 200 or less times, more preferably 15 or more times and 100 or less times as large as the exposure amount during the exposure in the step (B).

In this case, the integral irradiation illuminance in the irradiated ultraviolet light is preferably 200 mW/cm$^2$ or more. When the integral irradiation illuminance is 200 mW/cm$^2$ or more, effect of suppressing color transfer to adjacent pixels and upper and lower layers and effect of improving light resistance may be improved more effectively. Among these, 250 mW/cm$^2$ to 2000 mW/cm$^2$ is preferable, and 300 mW/cm$^2$ to 1000 mW/cm$^2$ is more preferable.

—Step (D)—

It is preferable that the colored pattern that has been subjected to post-exposure by ultraviolet radiation irradiation as mentioned above is subjected to heat treatment. By heating (so-called post-baking) the formed colored pattern, the colored pattern may further be cured.

This heat treatment may be performed by using, for example, a hot plate, various heaters, an oven or the like.

The temperature for the heat treatment is preferably 100° C. to 300° C., more preferably 150° C. to 250° C. The heating time is preferably 30 seconds to 30000 seconds, more preferably 60 seconds to 1000 seconds.

In the production method of the color filter of the invention, instead of the post-exposure by ultraviolet radiation irradiation as in the above-mentioned step (C), post-exposure by g-ray, h-ray, i-ray, KrF, ArF, electron beam or X-ray may be performed.

In the case of the post-exposure by these means, the irradiation time may be 10 seconds to 180 seconds, preferably 20 seconds to 120 seconds, further preferably 30 seconds to 60 seconds.

Alternatively, in the production method of the color filter of the invention, only the post-heating as in the above-mentioned step (D) may be performed without performing the post-exposure by ultraviolet radiation irradiation as in the above-mentioned step (C).

Although either the post-exposure or post-heating may be performed first, it is preferable to perform the post-exposure prior to the post-heating. In this case, by accelerating curing by the post-exposure, deformation due to heat sagging (change of a rectangular pattern into a spherical shape) and bottom spreading (reflowing of the lower part of the pattern) of the colored pattern that are observed in the subsequent post-heating step may be suppressed.

The thus-obtained colored pattern constitutes pixels of the color filter.

In the preparation of a color filter having pixels of plural hues, the above-mentioned steps (A) and (B), and optionally steps (C) and (D), may be repeated according to the desired numbers of colors.

The above-mentioned step (C) and/or step (D) may be performed after each completion of formation, exposure and development of a monochromatic curable composition layer (each color), or the above-mentioned step (C) and/or step (D) may be performed collectively after completion of formation, exposure and development of colored curable composition layers for all desired number of colors.

The color filter obtained by the production method of the color filter of the invention (the color filter of the invention) is excellent in light resistance since the colored curable composition of the invention is used.

Therefore, the color filter of the invention may be used for liquid crystal display devices, and solid-state image pickup devices including CCD image sensors and CMOS image sensors, and camera systems using them. Among these, it is preferable for use in a solid-state image pickup device in which a colored pattern with a minute size is formed on a thin film and a good rectangular cross-sectional profile is required, specifically for uses in CCD devices, CMOS and the like having high resolutions of more than 1,000,000 pixels.

<<Solid-State Image Pickup Device>>

The solid-state image pickup device of the invention includes the color filter of the invention. Since the color filter of the invention has high light resistance, a solid-state image pickup device including this color filter may provide excellent color reproducibility.

The configuration of the solid-state image pickup device is not specifically limited so long as it is a configuration that includes the color filter of the invention and acts as a solid-state image pickup device, and examples may include the following configuration.

Namely, it is a configuration including a support, plural photodiodes that constitute a light receiving area for a CCD image sensor (solid-state image pickup device) and transfer electrodes including polysilicon and the like formed on the support, the color filter of the invention formed thereon, and a microlens laminated thereon.

Furthermore, it is desirable that the camera system including the color filter of the invention includes a camera lens and an IR cut film that include dichroic-coated cover glass, microlens and the like in view of discoloration property of the coloring material, and that the materials therefor have an optical property to absorb a part or all parts of UV light of 400 nm or less. Furthermore, it is preferable that the structure of the camera system is a structure that decreases oxygen permeability to the color filter so as to suppress oxidation discoloration of the color material. For example, it is preferable that a part or all parts of the camera system is sealed with nitrogen gas.

<Liquid Crystal Display Device>

The color filter of the invention is excellent in hue and has colored pixels without chipping, peeling or unevenness, and thus is suitable as a color filter for a liquid crystal display device.

A liquid crystal display device having such a color filter may display a high quality image.

The definition of a display device and the explanation of each display device are described, for example, in "Electronic Display Device (Akio Sasaki, Kogyo Chosakai Publishing Co., Ltd., 1990", "Display Device (Sumiaki Ibuki, Sangyo Tosho Publishing Co., Ltd., 1989)" and the like. Liquid crystal display devices are described, for example, in "Next Generation Liquid Crystal Display Techniques (Tatsuo Uchida, Kogyo Chosakai Publishing Co., Ltd., 1994)". The liquid crystal display device to which the invention may be applied is not specifically limited, and the invention may be applied to various liquid crystal display devices described, for example, in the above "Next Generation Liquid Crystal Display Techniques".

The color filter of the invention is particulary effective in a color TFT liquid crystal display device. Color TFT liquid crystal display devices are described, for example, in "Color TFT Liquid Crystal Display (Kyoritsu Shuppan Co., Ltd., 1996)". Further, the invention may be applied to a liquid crystal display device with a wider view angle such as an in-plane switching (IPS) system or a multi-domain vertical alignment (MVA) system, or STN, TN, VA, OCS, FFS, R-OCB and the like.

The color filter of the invention may also be applied to a COA (Color-filter On Array) system, which has high brightness and high definition. In the COA type liquid crystal display device, the color filter layer should satisfy normal requirements as mentioned above, and further requirements for an interlayer dielectric film such as low dielectric constant and resistance to a removing liquid. By selecting the UV laser exposure method and the color and the film thickness of the pixels in the invention, the transmittance of the UV laser as an exposure light through the color filter of the invention may be increased. As a result, the curability of the colored pixels is improved to enable formation of pixels without chipping, peeling or unevenness, so that the resistance to a removing liquid is particulary improved in the colored layer provided directly or indirectly on the TFT substrate, and therefore the color filter of the invention is useful for the COA type liquid crystal display device. In order to satisfy the requirement of low dielectric constant, a resin coating may be provided on the color filter layer.

In the colored layer formed according to the COA system, in order to electrically connecting the ITO electrode disposed on the colored layer and the terminal of the driving substrate disposed below the colored layer, an electrically-conducting path such as a rectangular through hole having a side length of about 1 to 15 μm or a U-shaped depressed area should be formed, in which the size (that is, the side length) of the electrically-conducting path is preferably 5 μm or less. In the present invention, an electrically-conducting path having a size of 5 μm or less may also be formed.

These image display systems are describe, for example, on page 43 of "EL, PDP, LCD Display—Latest Current of Technique and Market (Research Study Division of Toray Research Center, Inc., 2001)" and the like.

The liquid crystal display device of the invention includes not only the color filter of the invention but also various members such as an electrode substrate, a polarization film, a phase difference film, a back light, a spacer, and a view angle compensation film. The color filter of the invention may be applied to a liquid crystal display device including these various known members.

These members are described, for example, in "'94 Market of Liquid Crystal Display Related Materials And Chemicals (Kentaro Shima, CMC Publishing CO., LTD., 1994)" and "2003 Current State And Perspective Of Liquid Crystal Related Market (Ryokichi Omote, Fuji Chimera Research Institute, Inc., 2003)".

Back lights are described, for example, in SID meeting Digest 1380 (2005) (A. Konno et. al) and Monthly Display, 2005 December, pages 18-24 (Hiroyasu Shima) and pages 25-30 (Takaaki Yagi).

When the color filter of the invention is used in a liquid crystal display device, high contrast may be obtained in combination with a conventionally known three-wavelength cold-cathode tube, but by using red, green and blue LED light sources (RGB-LED) as a back light, a liquid crystal display device having high brightness, high color purity, and good color reproducibility may be provided.

According to the invention, for example, the following exemplary embodiments <1> to <12> may be provided.

<1> A colored curable composition comprising at least (A-1) a complex comprising a compound represented by the following formula (I) and a metal atom or a metal compound, (A-2) a phthalocyanine pigment, (B) a dispersing agent, (C) a polymerizable compound, (D) a photopolymerization initiator, and (E) an organic solvent:

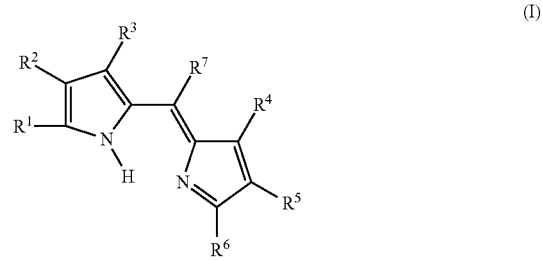

(I)

wherein $R^1$ to $R^6$ each independently represent a hydrogen atom or a substituent, but $R^1$ and $R^6$ do not bond to each other to form a ring structure; and $R^7$ represents a hydrogen atom, a halogen atom, an alkyl group, an aryl group or a heterocyclic group.

<2> The colored curable composition of <1>, wherein the (D) photopolymerization initiator is an oxime compound.

<3> The colored curable composition of <1> or <2>, wherein the (A-1) complex comprising the compound represented by the formula (I) and the metal atom or the metal compound is a compound represented by the following formula (II-1):

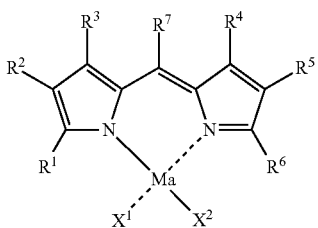

(II-1)

wherein $R^1$ to $R^6$ each independently represent a hydrogen atom or a substituent; $R^7$ represents a hydrogen atom, a halogen atom, an alkyl group, an aryl group or a heterocyclic group; Ma represents a metal atom or a metal compound; $X^2$ represents a group that is necessary for neutralizing the charge of Ma; and $X^1$ represents a group capable of bonding to Ma, wherein $X^1$ and $X^2$ may bond to each other to form a 5-, 6- or 7-membered ring.

<4> The colored curable composition of <1> or <2>, wherein the (A-1) complex comprising the compound represented by the formula (I) and the metal atom or the metal compound is a compound represented by the following formula (II-2):

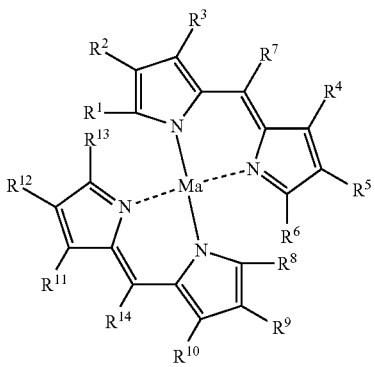

(II-2)

wherein $R^1$ to $R^6$ and $R^8$ to $R^{13}$ each independently represent a hydrogen atom or a substituent; $R^7$ and $R^{14}$ each independently represent a hydrogen atom, a halogen atom, an alkyl group, an aryl group or a heterocyclic group; and Ma represents a metal atom or a metal compound.

<5> The colored curable composition of <1> or <2>, wherein the (A-1) complex comprising the compound represented by the formula (I) and the metal atom or the metal compound is a compound represented by the following formula (III):

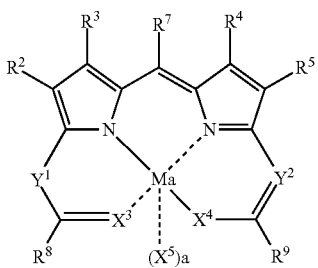

(III)

wherein: $R^2$ to $R^5$ each independently represent a hydrogen atom or a substituent; $R^7$ represents a hydrogen atom, a halogen atom, an alkyl group, an aryl group or a heterocyclic group; Ma represents a metal atom or a metal compound; $X^3$ represents NR (wherein R represents a hydrogen atom, an alkyl group, an alkenyl group, an aryl group, a heterocyclic group, an acyl group, an alkylsulfonyl group or an arylsulfonyl group), a nitrogen atom, an oxygen atom or a sulfur atom; $X^4$ represents NRa (wherein Ra represents a hydrogen atom, an alkyl group, an alkenyl group, an aryl group, a heterocyclic group, an acyl group, an alkylsulfonyl group or an arylsulfonyl group), an oxygen atom or a sulfur atom; $Y^1$ represents NRc (wherein Rc represents a hydrogen atom, an alkyl group, an alkenyl group, an aryl group, a heterocyclic group, an acyl group, an alkylsulfonyl group or an arylsulfonyl group), a nitrogen atom or a carbon atom; $Y^2$ represents a nitrogen atom or a carbon atom; $R^8$ and $R^9$ each independently represent an alkyl group, an alkenyl group, an aryl group, a heterocyclic group, an alkoxy group, an aryloxy group, an alkylamino group, an arylamino group or a heterocyclic amino group; $R^8$ and $Y^1$ may bond to each other to form a 5-, 6- or 7-membered ring; $R^9$ and $Y^2$ may bond to each other to form a 5-, 6- or 7-membered ring; $X^5$ represents a group capable of bonding to Ma; and a represents 0, 1 or 2.

<6> The colored curable composition of <1> or <2>, wherein the metal atom or the metal compound is any one of Fe, Zn, Co, V=O or Cu.

<7> The colored curable composition of <1> or <2>, wherein each of $R^3$ and $R^4$ in the formula (I) is a phenyl group.

<8> A method for producing a color filter, comprising:

(A) applying the colored curable composition of any one of <1> to <7> onto a support to form a colored curable composition layer, and (B) exposing the colored curable composition layer formed in (A) via a mask, and developing the layer to form a colored pattern.

<9> The method for producing a color filter of <8>, further comprising:

(C) irradiating the colored pattern formed in (B) with ultraviolet radiation, and (D) subjecting the colored pattern on which ultraviolet radiation has been irradiated in (C) to heat treatment.

<10> A color filter produced by the method for producing a color filter of <8> or <9>.

<11> A solid-state image pickup device comprising the color filter of <10>.

<12> A liquid crystal display device comprising the color filter of <10>.

Therefore, according to the invention, there may be provide a colored curable composition that is excellent in storage stability and may form a colored cured film having high light resistance.

Furthermore, according to the invention, a color filter having excellent light resistance, a method for producing the color filter, and a solid-state image pickup device and a liquid crystal display device including the color filter may be provided.

EXAMPLES

Hereinafter the present invention is further specifically explained by the Examples, but the invention should not be limited to the following Examples. Unless otherwise mentioned, "parts" and "%" are based on mass.

Example 1

1. Preparation of Colored Curable Composition

The following components are dispersed and dissolved by mixing to give a colored curable composition.

| | |
|---|---|
| Cyclohexanone (hereinafter referred to as "CyH") | 1.133 parts |
| Copolymer of benzyl methacrylate/methacrylic acid 20% CyH solution (molar ratio = 70:30, weight average molecular weight: 30000) | 1.009 parts |
| Fluorine-containing surfactant (trade name: SOLSPERSE 20000, manufactured by Lubrizol Japan Ltd.) 1% CyH solution | 0.125 parts |
| Oxime photopolymerization initiator (a compound having the following structure) | 0.087 parts |
| Specific complex (Exemplified compound Ia-5) | 0.183 parts |
| Pigment Blue-15:6 dispersion liquid (solid content concentration: 17.70%, pigment concentration: 11.80%) | 2.418 parts |
| Glycerol propoxylate 1% CyH solution | 0.048 parts |
| Dipentaerythritol hexaacrylate (trade name: KAYARAD DPHA, manufactured by Nippon Kayaku Co., Ltd.) | 0.225 parts |

The above Pigment Blue-15:6 dispersion liquid was prepared by dispersing the following composition with 0.5 mm zirconia beads using a dispersing machine (trade name: DISPERMAT, manufactured by GETZMANN) for 2 hours.

| | |
|---|---|
| Colorant: Pigment Blue-15:6 | 59.00 parts |
| Resin solution (Benzyl methacrylate/methacrylic acid copolymer, molar ratio = 80:20, Mw: 10000, resin solid content concentration: 30%, solvent: propylene glycol monomethyl ether acetate (hereinafter referred to as "PGMEA") 70%) | 19.65 parts |
| Solvent: PGMEA | 342.7 parts |
| Dispersing agent (trade name: BYK-161, manufactured by BYK) 30% solution (solvent: PGMEA and butyl acetate) | 78.65 parts |

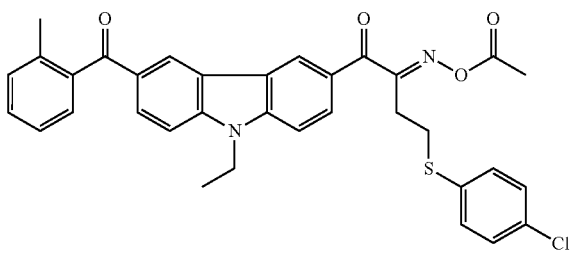 [SMILES: CCn1c2ccc(C(=O)/C(CCSc3ccc(Cl)cc3)=N/OC(C)=O)cc2c2cc(C(=O)c3ccccc3C)ccc21]

2. Evaluation of Storage Stability

The colored curable composition obtained in the above 1. was stored for one month at room temperature, and thereafter the degree of precipitation was evaluated by visual observation according to the following evaluation criteria. The results are shown in Table 1.
A: Precipitation was not observed.
B: Precipitation was slightly observed.
C: Precipitation was observed.

3. Preparation of Monochromatic Color Filter and Evaluation of Light Resistance The colored curable composition obtained in the above 1. was applied onto a glass substrate using a spin coater so that the film thickness after drying became 0.6 μm, and pre-baked at 100° C. for 120 seconds to give a monochromatic color filter for evaluation of light resistance.

The obtained monochromatic color filter for evaluation of light resistance was irradiated with a xenon lamp at 100,000 lux for 20 hours (corresponding to 2,000,000 lux·h). The color difference ($\Delta E^*ab$ value) of the monochromatic color filter before and after irradiation with the xenon lamp was measured and used as an index of light resistance. The smaller the $\Delta E^*ab$ value is, the better the light resistance is, and the evaluation criteria is as follows. The results are shown in Table 1.

—Evaluation Criteria—
A: $\Delta E^*ab$ value<1
B: $1 \leq \Delta E^*ab$ value<3
C: $3 \leq \Delta E^*ab$ value$\leq 10$
D: $10 < \Delta E^*ab$ value

Examples 2 to 26, and Comparative Examples 1 to 5

Colored curable compositions were prepared in a similar manner to Example 1, expect that the "specific complex (Exemplified Compound Ia-5)" in the colored curable composition of Example 1 was changed to Exemplified Compound or Comparative Colorant A described in the following Table 1, and the "Pigment Blue-15:6" was not added or was suitably changed to the pigment or Comparative Colorant B described in the following Table 1.

For the obtained colored curable compositions, storage stability was evaluated in a similar manner to Example 1. Furthermore, monochromatic color filters were prepared using the obtained colored curable compositions in a similar manner to Example 1, and light resistance was evaluated for the monochromatic color filters in a similar manner to Example 1. The results are shown in Table 1.

As Pigment Blue-15 used in Examples 23 and 25, a Pigment Blue-15 dispersion liquid was used which was prepared in a similar manner to the above Pigment Blue-15:6 dispersion liquid except that Pigment Blue-15:6 was changed to Pigment Blue-15 in the preparation of the Pigment Blue-15:6 dispersion liquid.

As Pigment Blue-15:3 used in Examples 24 and 26, a Pigment Blue-15:3 dispersion liquid was used which was prepared in a similar manner to the above Pigment Blue-15:6 dispersion liquid except that Pigment Blue-15:6 was changed to Pigment Blue-15:3 in the preparation of the Pigment Blue-15:6 dispersion liquid.

In Comparative Examples 1 to 5, colored curable compositions in which the solid concentration of the pigment and/or dye had been adjusted to be the same as that of the colored curable composition of Example 1 as follows were used.

In Comparative Examples 1 and 2, the dispersion liquid of Pigment Blue-15:6 used in Example 1 was replaced with a 20% CyH solution of benzyl methacrylate/methacrylic acid copolymer to adjust the solid content concentration of the dye (III-47 or C. I. Acid Violet-17).

In Comparative Example 3, a dye (CB-34) was used in an amount corresponding to the pigment content in the dispersion liquid of Pigment Blue-15:6 used in Example 1, and the part other than the pigment in the dispersion liquid was replaced with a 20% CyH solution of benzyl methacrylate/methacrylic acid copolymer to adjust the solid concentration of the dye (CB-34).

In Comparative Example 4, the specific complex (Exemplified Compound Ia-5) used in Example 1 was replaced with C. I. Acid Violet-17.

In Comparative Example 5, a dispersion liquid of Pigment Violet-23 (solid content concentration: 17.70%, pigment concentration: 11.80%) was added so that the amount of the pigment (Pigment Violet-23) became similar to the amount of the specific complex (Exemplified Compound Ia-5) used in Example 1, and in accordance with this, the 20% CyH solution of benzyl methacrylate/methacrylic acid copolymer was decreased to adjust the solid content concentration of the pigment (Pigment Violet-23).

As the Pigment Violet-23 dispersion liquid, a Pigment Violet-23 dispersion liquid was used which was prepared in a similar manner to the above Pigment Blue-15:6 dispersion liquid except that Pigment Blue-15:6 was changed to Pigment Violet-23 in the preparation of the Pigment Blue-15:6 dispersion liquid.

TABLE 1

|  | Specific complex or Comparative colorant A | Phthalocyanine pigment or Comparative colorant B | Light resistance | Storage stability |
|---|---|---|---|---|
| Example 1 | Ia-5 | Pigment Blue-15:6 | B | A |
| Example 2 | Ia-21 | Pigment Blue-15:6 | B | A |
| Example 3 | Ia-31 | Pigment Blue-15:6 | B | A |
| Example 4 | Ia-A | Pigment Blue-15:6 | B | A |
| Example 5 | II-1 | Pigment Blue-15:6 | B | A |
| Example 6 | II-7 | Pigment Blue-15:6 | A | A |
| Example 7 | II-4 | Pigment Blue-15:6 | B | A |
| Example 8 | II-A | Pigment Blue-15:6 | B | A |
| Example 9 | III-1 | Pigment Blue-15:6 | B | A |
| Example 10 | III-3 | Pigment Blue-15:6 | B | A |
| Example 11 | III-5 | Pigment Blue-15:6 | B | A |
| Example 12 | III-A | Pigment Blue-15:6 | B | A |
| Example 13 | III-45 | Pigment Blue-15:6 | A | A |
| Example 14 | III-47 | Pigment Blue-15:6 | A | A |
| Example 15 | III-65 | Pigment Blue-15:6 | B | A |
| Example 16 | III-68 | Pigment Blue-15:6 | B | A |
| Example 17 | III-69 | Pigment Blue-15:6 | A | A |
| Example 18 | III-70 | Pigment Blue-15:6 | B | A |
| Example 19 | III-B | Pigment Blue-15:6 | B | A |
| Example 20 | III-90 | Pigment Blue-15:6 | B | A |
| Example 21 | III-93 | Pigment Blue-15:6 | B | A |
| Example 22 | III-C | Pigment Blue-15:6 | B | A |
| Example 23 | III-5 | Pigment Blue-15 | B | A |
| Example 24 | III-5 | Pigment Blue-15:3 | B | A |
| Example 25 | III-47 | Pigment Blue-15 | A | A |
| Example 26 | III-47 | Pigment Blue-15:3 | A | A |
| Comparative Example 1 | III-47 | — | D | C |
| Comparative Example 2 | C.I. Acid Violet-17 | — | D | C |
| Comparative Example 3 | III-47 | CB-34 | D | C |
| Comparative Example 4 | C.I. Acid Violet-17 | Pigment Blue-15:6 | D | C |
| Comparative Example 5 | Pigment Violet-23 | Pigment Blue-15:6 | C | C |

The CB-34 used as Comparative colorant B described in Table 1 is a phthalocyanine dye having the following structure.

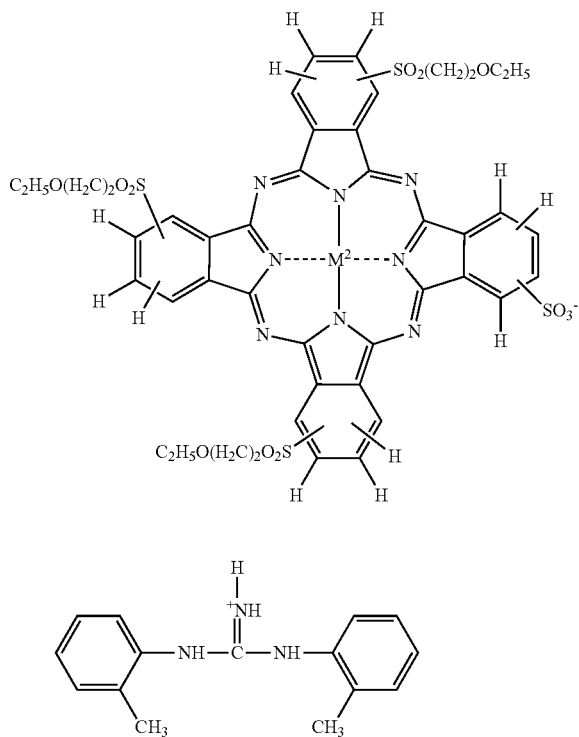

As is apparent from Table 1, it is recognized that a colored curable composition using the specific complex and a phthalocyanine pigment in combination has excellent storage stability, and that a monochromatic color filter formed using the colored curable composition has excellent light resistance.

Examples 8.2 to 14.2

Colored curable compositions of Examples 8.2 to 14.2 were prepared in a similar manner to Examples 8 to 14, except that the 20% CyH solution of the copolymer of benzyl methacrylate/methacrylic acid was changed to a 20% CyH solution of a polymerizable compound having a structure shown below.

The light resistance and the storage stability were evaluated in a similar manner to Example 1. The results are shown in Table 2.

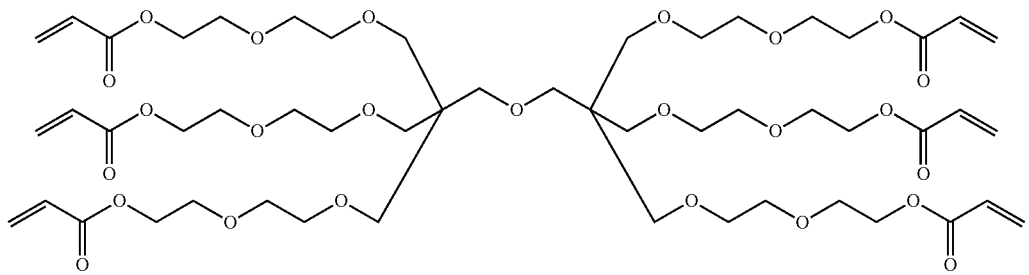 [SMILES: C=CC(=O)OCCOCCOCC(COCCOCCOC(=O)C=C)(COCCOCCOC(=O)C=C)COCC(COCCOCCOC(=O)C=C)(COCCOCCOC(=O)C=C)COCCOCCOC(=O)C=C]

TABLE 2

|  | Specific complex | Phthalocyanine pigment | Light resistance | Storage stability |
|---|---|---|---|---|
| Example 8.2 | II-A | Pigment Blue-15:6 | B | A |
| Example 9.2 | III-1 | Pigment Blue-15:6 | B | A |
| Example 10.2 | III-3 | Pigment Blue-15:6 | B | A |
| Example 11.2 | III-5 | Pigment Blue-15:6 | B | A |
| Example 12.2 | III-A | Pigment Blue-15:6 | B | A |
| Example 13.2 | III-45 | Pigment Blue-15:6 | A | A |
| Example 14.2 | III-47 | Pigment Blue-15:6 | A | A |

From the Table 2, it is understood that even if the copolymer of benzyl methacrylate/methacrylic acid was changed to the above polymerizable compound, the colored curable composition is excellent in light resistance and storage stability.

Example 27

A 6 inch silicon wafer was subjected to heat treatment in an oven at 200° C. for 30 minutes. A resist liquid in which the components shown below had been dissolved by mixing was then applied onto the silicon wafer so that the dry film thickness became 1.0 µm, and further dried in an oven at 220° C. for 1 hour to form a primer layer, whereby a silicon wafer substrate with a primer layer was obtained.

| | |
|---|---|
| PGMEA | 19.20 parts |
| Ethyl lactate (hereinafter referred to as "EL") | 36.67 parts |
| Binder: (benzyl methacrylate/methacrylic acid/2-hydroxyethyl methacrylate) copolymer (molar ratio = 60:20:20) 41% EL solution | 30.51 parts |
| Dipentaerythritol hexaacrylate | 12.20 parts |
| Polymerization inhibitor (p-methoxyphenol) | 0.0061 parts |
| Fluorine-containing surfactant (trade name: MEGAFAC F482, manufactured by DIC Corporation) | 0.83 parts |
| Photopolymerization initiator: 2-(1,3-benzodioxol-5-yl)-4,6,-bis(trichloromethyl)-1,3,5-triazine (trade name: TAZ-107, manufactured by Midori Kagaku Co., Ltd.) | 0.586 parts |

The colored curable composition used in Examples 1 to 26 was applied onto the primer layer of the obtained silicon wafer substrate with a primer layer so that the dried film thickness for each coating film became 0.6 µm an to form a photocurable coating film (colored curable composition layer). Heat treatment (pre-baking) was then performed using a hot plate at 100° C. for 120 seconds. Next, the resulting coating film was irradiated with light at a wavelength of 365 nm through an island pattern mask having a 1.2 µm-square pattern using an i-ray stepper-exposing apparatus (trade name: FPA-3000i5+, manufactured by Canon Inc.) while the exposure amount was changed by 100 mJ/cm$^2$ in the range of 100 mJ/cm$^2$ to 2500 mJ/cm$^2$. Thereafter, the silicon wafer substrate on which the irradiated coating film had been formed was placed on a horizontal rotary table of a spin-shower developing machine (trade name: MODEL DW-30, manufactured by Chemitronics Co., Ltd.) and subjected to paddle development at 23° C. for 60 seconds using CD-2000 (trade name, manufactured by Fujifilm Electronic Materials Co., Ltd.) to form a blue colored pattern on the silicon wafer substrate.

—Formation of Color Filter—

The silicon wafer substrate on which a blue colored pattern had been formed was fixed on the horizontal rotary table in a vacuum chuck mode, subjected to a rinse treatment by feeding pure water from an ejection nozzle in shower state from the upper side of the rotation center while the silicon wafer substrate is rotated by a rotation apparatus at a revolution number of 50 rpm, and then spray dried to give a color filter.

It was found that each of the formed blue colored patterns showed a square good profile having a rectangular cross-section and was a color filter suitable for a solid-state image pickup device.

Examples 28 to 53

1. Preparation of Colored Curable Composition

Colored curable compositions similar to Examples 1 to 26 were prepared. The specific complexes and phthalocyanine pigments included in the colored curable compositions of Examples 28 to 53 are shown in the following Table 3.

Using these colored curable compositions, color filters were prepared according to the following procedures, and color transfer and developing residue were evaluated.

2. Preparation of Monochromatic Color Filter (Preparation of Silicon Wafer with Primer Layer)

A solution of a resist (trade name: CT-2000L, manufactured by Fujifilm Electronic Materials Co., Ltd.; primer transparent agent) was applied onto a silicon wafer using a spin coater so that the film thickness became 2 µm, and dried at 220° C. for 1 hour to form a primer layer, whereby a silicon wafer with a primer layer was obtained.

(Exposure and Development of Colored Curable Composition)

Next, each of the colored curable compositions prepared as above was applied onto the primer layer of the obtained silicon wafer with the primer layer using a spin coater so that the dried film thickness became 1 µm, and pre-baked at 100° C. for 120 seconds to form a colored curable composition layer on the silicon wafer.

The colored curable composition layer was subjected to pattern exposing at an illuminance of 1200 mW/cm$^2$ (integral irradiation illuminance) by an exposure amount [mJ/cm$^2$] as shown in the following Table 2 through a mask pattern having 2.0 µm-square pixels each arrayed in an area of 4 mm×3 mm on the substrate using an i-ray stepper (trade name: FPA-3000i5+, manufactured by Canon Inc.). After exposure, the layer was subjected to paddle development at 23° C. for 60 seconds using a developer (trade name CD-2000, 60%, manufactured by Fujifilm Electronic Materials Co., Ltd.) to form a colored pattern. The colored pattern was then rinsed with flowing water for 20 seconds and subjected to spray drying.

The whole silicon wafer on which the colored pattern had been formed was irradiated with ultraviolet radiation (post-exposure) at an irradiation amount [mJ/cm$^2$] shown in the following Table 2 using a high pressure mercury lamp (trade name: UMA-802-HC552FFAL, manufactured by Ushio Inc.). After the irradiation, the silicon wafer was subjected to post-baking treatment on a hot plate at 220° C. for 300 seconds to accelerate curing of the colored pattern on the silicon wafer. The light at a wavelength of 275 nm or less included in the irradiation light from the high pressure mercury lamp was 10%.

In this way, a monochromatic color filter was prepared.

3. Evaluation of Color Transfer

A solution of a primer transparent agent (trade name: CT-2000L, manufactured by manufactured by Fujifilm Electronic Materials Co., Ltd.) was applied onto the surface, on which the colored pattern had been formed, of the monochromatic color filter prepared as above so that the dried film thickness became 1 μm, and dried to form a transparent film, and the film was subjected to heat treatment at 200° C. for 5 minutes. After the heating was completed, the absorbance of the transparent film adjacent to the colored pattern was measured using MCPD-3000 (trade name: manufactured by Otsuka Electron Co., Ltd.). The ratio [%] of the obtained absorbance value of the transparent film to the absorbance of the colored pattern that was measured in a similar manner prior to the heating was calculated, and was used as an index for evaluating color transfer.

A color transfer of 3% or less may be considered to be in an allowable range in practice.

4. Evaluation of Residue on Pixel

A coating resist liquid for evaluation of residue, which was prepared by the following method, was applied using a spin coater onto the surface, on which the colored pattern had been formed, of the monochromatic color filter prepared as above so that the dried film thickness became 1 μm, and pre-baked at 100° C. for 120 seconds, and the layer was subjected to paddle development at 23° C. for 60 seconds using a developer (trade name: CD-2060, manufactured by Fujifilm Electronic Materials Co., Ltd.). The colored pattern was then rinsed with flowing water for 20 seconds and subjected to spray drying. The developing residue (adhered substance) remained on the pixel was then observed using SEM (trade name: S-4800, manufactured by Hitachi Corporation).

(Preparation of Coating Resist Liquid for Evaluating Residue)

—Kneading and Dispersing Treatment—

The components of the following composition A were kneaded using a kneader for 30 minutes. After kneading, the composition was further subjected to high viscosity disperse treatment using two rolls. The viscosity of the dispersion at that time was 70,000 mPa·s. The weight average molecular weight of the alkali-soluble resin was obtained by measuring the molecular weight in the resin solution by GPC method and converting it into a polystyrene-converted weight average molecular weight.

[Composition A]

| | |
|---|---|
| Pigment Red 254 | 27 parts |
| Pigment Yellow 139 | 4 parts |
| PGMEA solution of benzyl methacrylate (BzMA)/methacrylic acid (MAA) copolymer (molar ratio of BzMA/MAA = 70/30, Mw: 30000, solid content: 50%) | 22 parts |
| Dispersing agent (trade name: BY-161, manufactured by BYK) | 2 parts |

—Microdispersion Treatment—

The components of the following composition B were added to the dispersion obtained as above, and stirred using a homogenizer under a condition of 3000 rpm for 3 hours. The obtained mixed solution was subjected to microdispersion treatment using a beads dispersing machine (trade name: DISPERMAT, manufactured by GETZMANN) using 0.3 mm zirconia beads for 4 hours. The viscosity of the mixed solution at that time was 20 mPa·s.

[Composition B]

| | |
|---|---|
| PGMEA solution of benzyl methacrylate (BzMA)/methacrylic acid (MAA) copolymer (molar ratio of BzMA/MAA = 70/30, Mw: 30000, solid content 50%) | 22 parts |
| PGMEA | 200 parts |

—High Pressure Dispersing Treatment—

The mixed solution obtained as above was subjected to a dispersion treatment under a pressure of 2,000 kg/cm$^3$ at a flow rate of 500 g/min using a vacuum mechanism-equipped high-pressure disperser (trade name: NANO-3000-10, manufactured by Nihon B. E. E. Co., Ltd.). This high-pressure dispersion treatment was repeated 10 times to obtain a dispersion liquid.

The components of the following composition C were added to the dispersion liquid obtained as above, and mixed by stirring to prepare a coating resist liquid for evaluating a residue.

[Composition C]

| | |
|---|---|
| Dipentaerythritol hexaacrylate (photopolymerizable monomer) | 27 parts |
| 4-[o-bromo-p-N,N-di(ethoxycarbonyl)aminophenyl]-2,6-di(trichloromethyl)-S-triazine (photopolymerization initiator) | 4 parts |
| Propylene glycol monomethyl ether acetate | 150 parts |

The evaluation criteria of the developing residue (adhered substance) remained on the pixel evaluated as above is as follows.

A: Residue was not observed at all.

B: Residue was slightly observed (the residues on the pixel were lower than 5, which was at an acceptable level in practice)

C: Residue was observed (the residues on the pixel were 5 or more)

Examples 54 to 79

The monochromatic color filters of Examples 54 to 79 were prepared in manners similar to Examples 28 to 53 except that irradiation of ultraviolet radiation using a high pressure mercury lamp (trade name: UMA-802-HC552FFAL, manufactured by Ushio Inc.) (post-exposure) was not performed in Examples 28 to 53. The specific complexes and phthalocyanine pigments included in the colored curable compositions of Examples 54 to 79 are shown in the following Table 4.

For the obtained monochromatic color filters, color transfer and residues on the pixels were evaluated in similar manners to Examples 28 to 53. The results are shown in Table 4.

Comparative Examples 6 to 10

Colored curable compositions similar to those of Comparative Examples 1 to 5 were prepared. The color materials (pigments and dyes) included in the colored curable compositions of Comparative Examples 6 to 10 are shown in the following Table 5.

Using these colored curable compositions, the monochromatic color filters in Comparative Examples 6 to 10 were prepared in similar manners to Examples 28 to 53.

For the obtained monochromatic color filters, color transfer and residues on the pixels were evaluated in similar manners to Examples 28 to 53. The results were shown in Table 5.

TABLE 3

|  | Specific complex | Phthalocyanine pigment | Irradiation amount in pattern exposure (mJ/cm$^2$) | Irradiation amount in post exposure (mJ/cm$^2$) | Color transfer (%) | Residues on pixel |
|---|---|---|---|---|---|---|
| Example 28 | Ia-5 | Pigment Blue-15:6 | 450 | 10000 | 0 | A |
| Example 29 | Ia-21 | Pigment Blue-15:6 | 450 | 10000 | 0 | A |
| Example 30 | Ia-31 | Pigment Blue-15:6 | 400 | 10000 | 0 | A |
| Example 31 | Ia-A | Pigment Blue-15:6 | 450 | 10000 | 0 | A |
| Example 32 | II-1 | Pigment Blue-15:6 | 400 | 10000 | 0 | A |
| Example 33 | II-2 | Pigment Blue-15:6 | 400 | 10000 | 0 | A |
| Example 34 | II-4 | Pigment Blue-15:6 | 500 | 10000 | 0 | A |
| Example 35 | II-A | Pigment Blue-15:6 | 400 | 10000 | 0 | A |
| Example 36 | III-1 | Pigment Blue-15:6 | 500 | 10000 | 0 | A |
| Example 37 | III-3 | Pigment Blue-15:6 | 500 | 10000 | 0 | A |
| Example 38 | III-5 | Pigment Blue-15:6 | 600 | 10000 | 0 | A |
| Example 39 | III-A | Pigment Blue-15:6 | 450 | 10000 | 0 | A |
| Example 40 | III-45 | Pigment Blue-15:6 | 400 | 10000 | 0 | A |
| Example 41 | III-47 | Pigment Blue-15:6 | 400 | 10000 | 0 | A |
| Example 42 | III-65 | Pigment Blue-15:6 | 400 | 10000 | 0 | A |
| Example 43 | III-68 | Pigment Blue-15:6 | 350 | 10000 | 0 | A |
| Example 44 | III-69 | Pigment Blue-15:6 | 550 | 10000 | 0 | A |
| Example 45 | III-70 | Pigment Blue-15:6 | 400 | 10000 | 0 | A |
| Example 46 | III-B | Pigment Blue-15:6 | 10000 | 10000 | 0 | A |
| Example 47 | III-90 | Pigment Blue-15:6 | 350 | 10000 | 0 | A |
| Example 48 | III-93 | Pigment Blue-15:6 | 350 | 10000 | 0 | A |
| Example 49 | III-C | Pigment Blue-15:6 | 350 | 10000 | 0 | A |
| Example 50 | III-5 | Pigment Blue-15 | 450 | 10000 | 0 | A |
| Example 51 | III-5 | Pigment Blue-15:3 | 450 | 10000 | 0 | A |
| Example 52 | III-47 | Pigment Blue-15 | 450 | 10000 | 0 | A |
| Example 53 | III-47 | Pigment Blue-15:3 | 550 | 10000 | 0 | A |

TABLE 4

|  | Specific complex | Phthalocyanine pigment | Irradiation amount in pattern exposure (mJ/cm$^2$) | Irradiation amount in post exposure (mJ/cm$^2$) | Color transfer (%) | Residues on pixel |
|---|---|---|---|---|---|---|
| Example 54 | Ia-5 | Pigment Blue-15:6 | 450 | None | 3 | B |
| Example 55 | Ia-21 | Pigment Blue-15:6 | 450 | None | 3 | B |
| Example 56 | Ia-31 | Pigment Blue-15:6 | 400 | None | 2 | B |
| Example 57 | Ia-A | Pigment Blue-15:6 | 450 | None | 3 | B |
| Example 58 | II-1 | Pigment Blue-15:6 | 400 | None | 1 | B |
| Example 59 | II-2 | Pigment Blue-15:6 | 400 | None | 3 | B |
| Example 60 | II-4 | Pigment Blue-15:6 | 500 | None | 3 | B |
| Example 61 | II-A | Pigment Blue-15:6 | 400 | None | 2 | B |
| Example 62 | III-1 | Pigment Blue-15:6 | 500 | None | 2 | B |
| Example 63 | III-3 | Pigment Blue-15:6 | 500 | None | 2 | B |
| Example 64 | III-5 | Pigment Blue-15:6 | 600 | None | 2 | B |
| Example 65 | III-A | Pigment Blue-15:6 | 450 | None | 1 | B |
| Example 66 | III-45 | Pigment Blue-15:6 | 400 | None | 1 | B |
| Example 67 | III-47 | Pigment Blue-15:6 | 400 | None | 3 | B |
| Example 68 | III-65 | Pigment Blue-15:6 | 400 | None | 3 | B |
| Example 69 | III-68 | Pigment Blue-15:6 | 350 | None | 3 | B |
| Example 70 | III-69 | Pigment Blue-15:6 | 550 | None | 3 | B |
| Example 71 | III-70 | Pigment Blue-15:6 | 400 | None | 3 | B |
| Example 72 | III-B | Pigment Blue-15:6 | 10000 | None | 3 | B |
| Example 73 | III-90 | Pigment Blue-15:6 | 350 | None | 2 | B |
| Example 74 | III-93 | Pigment Blue-15:6 | 350 | None | 1 | B |
| Example 75 | III-C | Pigment Blue-15:6 | 350 | None | 3 | B |
| Example 76 | III-5 | Pigment Blue-15 | 450 | None | 3 | B |
| Example 77 | III-5 | Pigment Blue-15:3 | 450 | None | 3 | B |
| Example 78 | III-47 | Pigment Blue-15 | 450 | None | 2 | B |
| Example 79 | III-47 | Pigment Blue-15:3 | 550 | None | 3 | B |

TABLE 5

| | Specific complex or Comparative colorant A | Phthalocyanine pigment or Comparative colorant B | Irradiation amount in pattern exposure (mJ/cm$^2$) | Irradiation amount in post exposure (mJ/cm$^2$) | Color transfer (%) | Residues on pixel |
|---|---|---|---|---|---|---|
| Comparative Example 6 | III-47 | — | 400 | None | 9 | C |
| Comparative Example 7 | C.I. Acid Violet-17 | — | 600 | None | 13 | C |
| Comparative Example 8 | III-47 | CB-34 | 350 | None | 7 | C |
| Comparative Example 9 | C.I. Acid Violet-17 | Pigment Blue-15:6 | 500 | None | 11 | B |
| Comparative Example 10 | Pigment Violet-23 | Pigment Blue-15:6 | 250 | None | 0 | C |

According to Examples 28 to 53 described in Table 3, it is recognized that color transfer is decreased and residues are difficult to be generated on the pixels by performing the step of post-exposure by ultraviolet radiation irradiation (step (C)) and the step of heat treatment (step (D)) during the production of the color filter using the colored curable composition of the invention. Therefore, it is recognized that color transfer to adjacent pixels and layers to be laminated is suppressed by applying the above-mentioned production method to the colored curable composition of the invention.

Furthermore, it was also recognized that color transfer to adjacent pixels and/or residues on pixels were generated and practical use was difficult when post-exposure by ultraviolet radiation irradiation was not performed in the cases of the colored curable composition of Comparative Examples 6 to 10.

Example 80

Preparation of Colored Curable Composition

The colored curable composition of Example 80 was prepared with the following composition.

| | |
|---|---|
| Pigment Blue-15:6 dispersion liquid (solid content concentration: 17.7%, pigment concentration: 11.8%) | 33.90 parts |
| Specific complex (Exemplified compound IV-A) | 1.60 parts |
| Polymerizable compound: pentaerythritol tetraacrylate | 6.26 parts |
| Photopolymerization initiator: 2-(o-chlorophenyl)-4,5-diphenylimidazolyl dimer | 0.271 parts |
| Photopolymerization initiator: 1,2-octanedione, 1-[4-(phenylthio)-, 2-(O-benzoyloxime)] (trade name: IRGACURE OXE01, manufactured by Ciba Specialty Chemicals) | 0.622 parts |
| Sensitizing dye: 4,4'-bis(diethylamino)benzophenone | 0.277 parts |
| Hydrogen donating compound: 2-mercaptobenzothiazole | 0.380 parts |
| Alkali soluble resin: Benzyl methacrylate/methacrylic acid copolymer, molar ratio = 70:30, Mw: 10000, 30% solid content solution (solvent: PGMEA) | 13.22 parts |
| Epoxy compound: EPICLON 695 (trade name, manufactured by DIC Corporation) | 0.60 parts |
| Polymerization inhibitor (p-methoxyphenol) | 0.003 parts |
| Surfactant (trade name: MEGAFAC F482, manufactured by DIC Corporation) | 0.02 parts |
| Solvent: PGMEA | 42.85 parts |

<Preparation of Color Filter Using Colored Curable Composition>

The above obtained colored curable composition (color resist liquid) was applied onto a glass substrate having a size of 100 mm×100 mm (trade name: 1737, manufactured by Corning Inc.) using a spin coater so that the dry film thickness became 2.2 μm, and pre-baked (dried in an oven at 100° C. for 80 seconds). Thereafter, the whole surface of the coating film was exposed at 100 mJ/cm$^2$ (illuminance 20 mW/cm$^2$), and the coating film after exposure was covered with 1% aqueous solution of alkali developing liquid CDK-1 (trade name, manufactured by Fujifilm Electronic Materials Co., Ltd.) and allowed to stand still for 60 seconds. After the standing still, the developing liquid on the coating film was washed away by a shower of pure water. Then, the coating film to which exposure and development had been carried out as above was subjected to a heating treatment in an oven at 200° C. for 0.5 hours (post-baking) to prepare a color filter substrate (color filter).

The color filter substrate was irradiate with a xenon lamp at 100,000 lux for 20 hours (corresponding to 2,000,000 lux·h). The color difference (ΔE*ab value) of the monochromatic color filter before and after irradiation with the xenon lamp was measured with MCPD-3000 (trade name: manufactured by Otsuka Electron Co., Ltd.), and used as an index of light resistance. The smaller the ΔE*ab value is, the better the light resistance is, and the evaluation criteria is as follows.

—Evaluation Criteria—
A: ΔE*ab value<1
B: 1≦ΔE*ab value<3
C: 3≦ΔE*ab value≦10
D: 10<ΔE*ab value The storage stability was evaluated in a similar manner to Example 1. These results are shown in Table 6.

Example 81

Preparation of Colored Curable Composition

The colored curable composition of Example 81 was prepared with the following composition, and evaluated in a similar manner to Example 80.

| | |
|---|---:|
| Pigment Blue-15:6 dispersion liquid (solid content concentration: 17.7%, pigment concentration: 11.8%) | 33.90 parts |
| Specific complex (Exemplified compound IV-A) | 1.60 parts |
| Polymerizable compound: pentaerythritol tetraacrylate | 3.13 parts |
| Polymerizable compound: Ethoxylated bisphenol A diacrylate (trade name: A-BPE-20, manufacture by Shin-Nakamura Chemical Co., Ltd.) | 3.13 parts |
| Photopolymerization initiator: 2-(o-chlorophenyl)-4,5-diphenylimidazolyl dimer | 0.271 parts |
| Photopolymerization initiator: IRGACURE OXE01 (trade name, manufactured by Ciba Specialty Chemicals) | 0.622 parts |
| Sensitizing dye: 4,4'-bis(diethylamino)benzophenone | 0.277 parts |
| Hydrogen donating compound: 2-mercaptobenzothiazole | 0.380 parts |
| Alkali soluble resin: Benzyl methacrylate/methacrylic acid copolymer, molar ratio = 70:30, Mw: 10000, 30% solid content solution (solvent: PGMEA) | 13.22 parts |
| Epoxy compound: EPICLON 695 (trade name, manufactured by DIC Corporation) | 0.60 parts |
| Polymerization inhibitor (p-methoxyphenol) | 0.003 parts |
| Surfactant (trade name: MEGAFAC F482, manufactured by DIC Corporation) | 0.02 parts |
| Solvent: PGMEA | 42.85 parts |

Example 82

Preparation of Colored Curable Composition

The colored curable composition of Example 82 was prepared with the following composition, and evaluated in a similar manner to Example 80.

| | |
|---|---:|
| Pigment Blue-15:6 dispersion liquid (solid content concentration: 17.7%, pigment concentration: 11.8%) | 33.90 parts |
| Specific complex (Exemplified compound IV-A) | 1.60 parts |
| Polymerizable compound: pentaerythritol tetraacrylate | 4.25 parts |
| Photopolymerization initiator: Oxime photopolymerization initiator used in Example 1 | 3.47 parts |
| Alkali soluble resin: Benzyl methacrylate/methacrylic acid copolymer, molar ratio = 70:30, Mw: 10000, 30% solid content solution (solvent: PGMEA) | 12.21 parts |
| Epoxy compound: EPICLON 695 (trade name, manufactured by DIC Corporation) | 1.00 parts |
| Polymerization inhibitor (p-methoxyphenol) | 0.002 parts |
| Surfactant (trade name: MEGAFAC F482, manufactured by DIC Corporation) | 0.02 parts |
| Solvent: PGMEA | 43.56 parts |

Example 83

The photocurable composition obtained in Example 82 (color resist liquid) was applied onto a glass substrate having a size of 100 mm×100 mm (trade name: 1737, manufactured by Corning Inc.) using a spin coater so that the film thickness became 2.2 µm, and pre-baked (dried in an oven at 100° C. for 80 seconds).

Thereafter, the surface of the photosensitive resin composition layer was subjected to pulse irradiation at about 1 mJ/cm$^2$ twenty times using a laser exposre apparatus EGIS (trade name, manufactured by V Technology Co., Ltd., third harmonic of YAG laser, wavelength: 355 nm, pulse width: 6 nsec) through a photo mask having a line width of 20 µm.

The coating film after exposure was covered with 1% aqueous solution of alkali developing liquid CDK-1 (trade name, manufactured by Fujifilm Electronic Materials Co., Ltd.) and allowed to stand still for 60 seconds. After the standing still, the developing liquid on the coating film was washed away by a shower of pure water. Then, the coating film to which exposure and development had been carried out as above was subjected to a heating treatment in an oven at 200° C. for 0.5 hours (post-baking) to prepare a color filter substrate (color filter).

The color filter substrate was irradiate with a xenon lamp at 100,000 lux for 20 hours (corresponding to 2,000,000 lux·h). The color difference (ΔE*ab value) of the monochromatic color filter before and after irradiation with the xenon lamp was measured with a microspectrophotometer (trade name: OSP100, manufactured by Olympus Corporation) at a pinhole diameter of 5 µm, and used as an index of light resistance.

The smaller the ΔE*ab value is, the better the light resistance is, and the evaluation criteria is as follows. The results are shown in Table 6.

—Evaluation Criteria—

A: ΔE*ab value<1

B: 1≦ΔE*ab value<3

C: 3≦ΔE*ab value≦10

D: 10<ΔE*ab value

The storage stability was evaluated in a similar manner to Example 1. These results are shown in Table 6.

Example 84

Preparation of Colored Curable Composition

The colored curable composition of Example 84 was prepared with the following composition and evaluated in a similar manner to Example 80 except that the film thickness of the colored curable composition layer after drying was 3.3 µm.

| | Specific complex | Phthalocyanine pigment | Light resistance | Storage stability |
|---|---|---|---|---|
| Pigment Blue-15:6 dispersion liquid | | | | 22.64 parts |
| (solid content concentration: 17.7%, pigment concentration: 11.8%) | | | | |
| Specific complex (Exemplified compound IV-A) | | | | 1.07 parts |
| Polymerizable compound: pentaerythritol tetraacrylate | | | | 5.15 parts |
| Photopolymerization initiator: Oxime photopolymerization initiator used in Example 1 | | | | 3.22 parts |
| Alkali soluble resin: Benzyl methacrylate/methacrylic acid copolymer, molar ratio = 70:30, Mw: 10000, 30% solid content solution (solvent: PGMEA) | | | | 18.45 parts |
| Epoxy compound: EPICLON 695 (trade name, manufactured by DIC Corporation) | | | | 1.00 parts |
| Polymerization inhibitor (p-methoxyphenol) | | | | 0.003 parts |
| Surfactant (trade name: MEGAFAC F482, manufactured by DIC Corporation) | | | | 0.02 parts |
| Solvent: PGMEA | | | | 48.46 parts |

TABLE 6

| | Specific complex | Phthalocyanine pigment | Light resistance | Storage stability |
|---|---|---|---|---|
| Example 80 | IV-A | Pigment Blue-15:6 | A | A |
| Example 81 | IV-A | Pigment Blue-15:6 | A | A |
| Example 82 | IV-A | Pigment Blue-15:6 | A | A |
| Example 83 | IV-A | Pigment Blue-15:6 | A | A |
| Example 84 | IV-A | Pigment Blue-15:6 | A | A |

From the results shown in Tables 1, 2 and 6, it is understood that the colored curable composition of the invention is excellent in storage stability and may form a color filter having good light resistance.

All publications, patent applications, and technical standards mentioned in this specification are herein incorporated by reference to the same extent as if each individual publication, patent application, or technical standard was specifically and individually indicated to be incorporated by reference.

What is claimed is:

1. A colored curable composition comprising at least (A-1) a complex comprising a compound represented by the following formula (I) and a metal atom or a metal compound, (A-2) a phthalocyanine pigment, (B) a dispersing agent, (C) a polymerizable compound, (D) a photopolymerization initiator, and (E) an organic solvent:

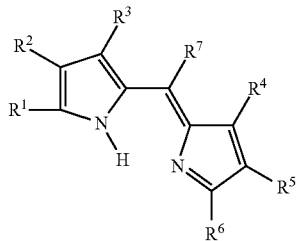

(I)

wherein $R^1$ to $R^6$ each independently represent a hydrogen atom or a substituent, but $R^1$ and $R^6$ do not bond to each other to form a ring structure; and $R^7$ represents a hydrogen atom, a halogen atom, an alkyl group, an aryl group or a heterocyclic group.

2. The colored curable composition of claim 1, wherein the (D) photopolymerization initiator is an oxime compound.

3. The colored curable composition of claim 1, wherein the (A-1) complex comprising the compound represented by the formula (I) and the metal atom or the metal compound is a compound represented by the following formula (II-1):

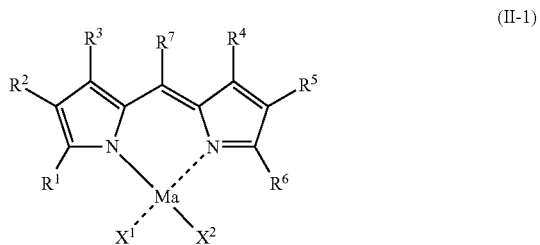

(II-1)

wherein $R^1$ to $R^6$ each independently represent a hydrogen atom or a substituent; $R^7$ represents a hydrogen atom, a halogen atom, an alkyl group, an aryl group or a heterocyclic group; Ma represents a metal atom or a metal compound; $X^2$ represents a group that is necessary for neutralizing the charge of Ma; and $X^1$ represents a group capable of bonding to Ma, wherein $X^1$ and $X^2$ may bond to each other to form a 5-, 6- or 7-membered ring.

4. The colored curable composition of claim 1, wherein the (A-1) complex comprising the compound represented by the formula (I) and the metal atom or the metal compound is a compound represented by the following formula (II-2):

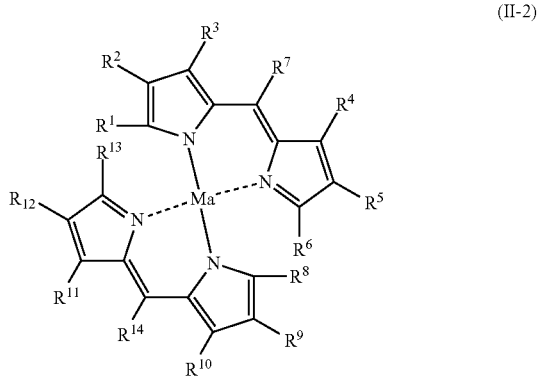

(II-2)

wherein $R^1$ to $R^6$ and $R^8$ to $R^{13}$ each independently represent a hydrogen atom or a substituent; $R^7$ and $R^{14}$ each independently represent a hydrogen atom, a halogen atom, an alkyl group, an aryl group or a heterocyclic group; and Ma represents a metal atom or a metal compound.

5. The colored curable composition of claim 1, wherein the metal atom or the metal compound is any one of Fe, Zn, Co, V=O or Cu.

6. The colored curable composition of claim 1, wherein each of $R^3$ and $R^4$ in the formula (I) is a phenyl group.

7. A method for producing a color filter, comprising: (A) applying the colored curable composition of claim 1 onto a support to form a colored curable composition layer, and (B) exposing the colored curable composition layer formed in (A) via a mask, and developing the layer to form a colored pattern.

8. The method for producing a color filter of claim 7, further comprising: (C) irradiating the colored pattern formed in (B) with ultraviolet radiation, and (D) subjecting the colored pattern on which ultraviolet radiation has been irradiated in (C) to heat treatment.

9. A color filter produced by the method for producing a color filter of claim 7.

10. A solid-state image pickup device comprising the color filter of claim 9.

11. A liquid crystal display device comprising the color filter of claim 9.

* * * * *